United States Patent
Hardy et al.

(10) Patent No.: US 6,288,075 B1
(45) Date of Patent: Sep. 11, 2001

(54) THIAZOLO[5,4,3-IJ]QUINOLINES, PREPARATION AND MEDICINES CONTAINING THE SAME

(75) Inventors: Jean-Claude Hardy, Cergy Saint Christophe; Jean Bouquerel, Drancy; Patrick Nemecek, Thiais; Jean-Claude Aloup, Villeneuve le Roi; Serge Mignani, Chatenay-Malabry; Jean-François Peyronel, Palaiseau, all of (FR)

(73) Assignee: Rhone-Poulenc Rorer S.A., Antony (FR)

( * ) Notice: Subject to any disclaimer, the term of this patent is extended or adjusted under 35 U.S.C. 154(b) by 0 days.

(21) Appl. No.: 09/384,237

(22) Filed: Aug. 27, 1999

Related U.S. Application Data

(63) Continuation of application No. PCT/FR98/00376, filed on Feb. 26, 1998.

(51) Int. Cl.[7] .................. C07D 513/06; A61K 31/4743; A61P 9/10; A61P 25/07
(52) U.S. Cl. ............................. 514/291; 546/80
(58) Field of Search ............................. 514/291; 546/80

(56) References Cited

U.S. PATENT DOCUMENTS 3,992,378   11/1976   St. Clair et al. .................... 260/250

FOREIGN PATENT DOCUMENTS

| 0 348 872 A1 | 1/1990 | (EP) . |
| 0 509 398 A1 | 10/1992 | (EP) . |
| 0 705 835 A1 | 4/1996 | (EP) . |
| WO 90 15058 A1 | 12/1990 | (WO) . |

OTHER PUBLICATIONS

Pellicciari, Roberto and Costantino, Gabriele, Curr. Opin. Chem. Biol., 4(3), 1999, 433–440.*
Ziff, E.B., Annals, NY Acad. Sci., 868, 1999, 465–473.*
Derwent Abstract of EP 0 705 835 (No. 96–171910) 1996.
Derwent Abstract of EP 0 509 398 (No. 92–351073) 1992.
Derwent Abstract 80–72381 1980.
Chemical Abstracts, vol. 59, No. 10, Nov. 11, 1963, abs. No. 11471b.
Chemical Abstracts, vol. 79, No. 3, Jul. 23, 1973, abs. No. 18669r.
Patent Abstracts of Japan, vol. 004, No. 173 (C–032), Nov. 29, 1980, No. JP 55111406.
A. Richardson, Jr.: The Synthesis and Chemistry of Certain 2–Substituted 5,6–Dihydroimidazo–, –oxazolo–, and –thiazolo[ij]quinolines. Journal of Organic Chemistry, vol. 28, No. 10, pp. 2581–2587 (1963).
M. Hönel et al.: Selectivity in the Hydrogenation of 6– and 8–Substituted–quinolines. Journal of the Chemical Society, Perkin Transactions I, vol. 9, pp. 1933–1939 (1980).
K. V. Rao (I) et al.: Reaction of Sodium Borohydride with Heteroaromatic Nitro Compounds. J. Heterocycl. Chem., vol. 10, No. 2, pp. 213–215 (1973).
The Condensed Chemical Dictionary, 9th Ed., Gessner G. Hawley Ed., Van Nostrand, New York, p 480, 1965.*

* cited by examiner

*Primary Examiner*—Mukund J. Shah
*Assistant Examiner*—Thomas McKenzie
(74) *Attorney, Agent, or Firm*—Finnegan, Henderson, Farabow, Garrett & Dunner L.L.P.

(57) ABSTRACT

Compounds of formula (I):

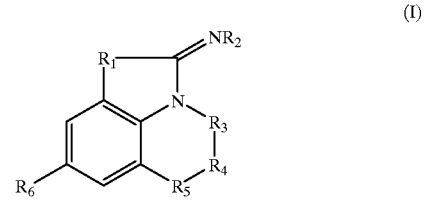

their racemates, enantiomers, diastereoisomers and inorganic acid salts and organic acid salts thereof, processes for preparing them and the medicaments containing them are discussed.

24 Claims, No Drawings

THIAZOLO[5,4,3-IJ]QUINOLINES, PREPARATION AND MEDICINES CONTAINING THE SAME

This application is a continuation of International Application No. PCT/FR98/00376, filed Feb. 26, 1997, the content of which is incorporated herein by reference.

Thiazolobenzoheterocycle derivatives are described by A. RICHARDSON, J. Org. Chem., 28, 2581–87 (1963) but no pharmacological activity is mentioned for these products.

The present invention relates to compounds of formula:

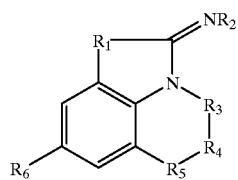

their salts, processes for preparing them and the medicaments containing them.

In formula (I),
$R_1$ represents a sulphur or selenium atom,
$R_2$ represents a hydrogen atom or an alkyl radical,
—$R_3$—$R_4$—$R_5$— represents a chain of formula —$CH_2$—$CH_2$—$CH_2$—, —$CH(R_7)$—$CH_2$—$CH_2$—, —$CH_2$—$CH_2$—$CH(R_8)$—, —$CH_2$—$CH(R_9)$—$CH_2$—, —$CH_2$—$CH_2$—S—, —$CH_2$—$CH_2$—SO—, —$CH_2$—$CH_2$—$SO_2$—, —$CH_2$—$CH_2$—Se—, —$CH_2$—$CH_2$—O—, —$CH_2$—$CH_2$—CO—, —$CH_2$—$CH_2$—N($R_{10}$)—, —$CH_2$—CO—N($R_{11}$)—, —$CH_2$—$CF_2$—$CH_2$—, —$CH_2$—$CF_2$—CH(OH)—, —$CH_2$—CH($R_{13}$)—S—, —$CH_2$—CH($R_{13}$)—SO— or —$CH_2$—CH($R_{13}$)—$SO_2$—,
$R_6$ represents a polyfluoroalkyl, polyfluoroalkoxy or polyfluoroalkylthio radical,
$R_7$ represents an alkyl, —$CH_2OH$, —$CH_2$—$SO_2$-alk or —$CH_2$—$NR_{11}R_{12}$ radical,
$R_8$ represents a radical alkyl, hydroxyl, —$CH_2OH$, —$NR_{11}R_{12}$, —$CH_2$—$NR_{11}R_{12}$, —S-alk, —SO-alk, —$SO_2$-alk, thienyl, furyl, phenyl or phenyl substituted with a substituent chosen from halogen atoms and alkyl and alkoxy radicals,
$R_9$ represents an alkyl or —$CH_2OH$ radical,
$R_{10}$ represents a hydrogen atom or an alkyl radical,
$R_{11}$ represents a hydrogen atom or an alkyl, —CO-alk or —CO—$CF_3$ radical,
$R_{12}$ represents a hydrogen atom or an alkyl radical, or alternatively $R_{11}$ and $R_{12}$ form with the nitrogen atom to which they are attached a saturated or unsaturated 5- or 6-membered heterocycle optionally containing another heteroatom chosen from nitrogen, oxygen and sulphur, this heterocycle being unsubstituted or substituted with one or more substituents chosen from alkyl, phenyl, halophenyl and phenylalkyl radicals,
$R_{13}$ represents an alkyl or —$CH_2OH$ radical, alk represents an alkyl radical.

In the preceding definitions and in those which will be given hereinafter, unless otherwise indicated, the alkyl and alkoxy radicals and portions contain 1 to 6 straight- or branched-chain carbon atoms and the halogen atoms are bromine, chlorine, fluorine and iodine atoms.

Among the polyfluoroalkyl radicals, there may be mentioned the trifluoromethyl, 2,2,2-trifluoroethyl, 1,1,2,2-tetrafluoroethyl, perfluoroethyl, perfluoropropyl and perfluorobutyl radicals.

Among the polyfluoroalkoxy radicals, there may be mentioned the trifluoromethoxy, perfluoroethoxy, 2,2,2-trifluoroethoxy, 1,1,2,2-tetrafluoroethoxy, 2,2,3,3,3-pentafluoropropoxy, perfluoropropoxy and perfluorobutoxy radicals.

Among the polyfluoroalkylthio radicals, there may be mentioned the trifluoromethylthio, perfluoroethylthio and perfluoropropylthio radicals.

The preferred polyfluoroalkyl, polyfluoroalkoxy and polyfluoroalkylthio radicals are trifluoromethyl, trifluoromethoxy, pentafluoroethoxy and trifluoromethylthio radicals.

As saturated or unsaturated 5- or 6-membered heterocycle optionally containing another heteroatom chosen from nitrogen, oxygen and sulphur, there may be mentioned pyrrolidine, piperidine, piperazine, morpholine and thiomorpholine, these heterocycles being unsubstituted or substituted with an alkyl, phenyl, halophenyl or phenylalkyl radical.

The invention also relates to the addition salts of the compounds of formula (I) with inorganic or organic acids.

The compounds of formula (I) which contain one or more asymmetric centres have isomeric forms; these isomers and mixtures form part of the invention. The racemates and the enantiomers of these compounds also form part of the invention.

The compounds of formula (I) for which $R_1$ represents a sulphur or selenium atom, $R_2$ represents a hydrogen atom, —$R_3$—$R_4$—$R_5$— represents a chain of formula —$CH_2$—$CH_2$—$CH_2$—, —$CH(R_7)$—$CH_2$—$CH_2$, —$CH_2$—$CH_2$—$CH(R_{11})$—, —$CH_2$—$CH(R_9)$—$CH_2$—, —$CH_2$—$CH_2$—S—, —$CH_2$—$CH_2$—Se—, —$CH_2$—$CH_2$—O—, —$CH_2$—$CH_2$—CO—, —$CH_2$—$CH_2$—N($R_{11}$)—, —$CH_2$—CO—N($R_{11}$)—, —$CH_2$—$CF_2$—$CH_2$—, —$CH_2$—$CF_2$—CH(OH)—, —$CH_2$—CH($R_{13}$)—S—, with the proviso that $R_8$ does not represent a hydroxyl radical, may be prepared by reacting an alkali metal thiocyanate or an alkali metal selenocyanate with a derivative of formula:

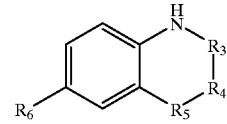

in which $R_6$ has the same meanings as in formula (I) —$R_3$—$R_4$—$R_5$— represents a chain of formula —$CH_2$—$CH_2$—$CH_2$—, —$CH(R_7)$—$CH_2$—$CH_2$—, —$CH_2$—$CH_2$—$CH(R_8)$—, —$CH_2$—$CH(R_9)$—$CH_2$—, —$CH_2$—$CH_2$—S—, —$CH_2$—$CH_2$—Se—, —$CH_2$—$CH_2$—O—, —$CH_2$—$CH_2$—CO—, —$CH_2$—$CH_2$—N($R_{10}$)—, —$CH_2$—$CF_2$—$CH_2$—, —$CH_2$—$CF_2$—CH(OH)—, —$CH_2$—CH($R_{13}$)—S—, —$CH_2$—CO—N($R_{10}$)— in which $R_7$, $R_8$, $R_9$, $R_{10}$ and $R_{13}$ have the same meanings as in formula (I) with the proviso that $R_8$ does not represent a hydroxyl radical.

This reaction is generally carried out in the presence of bromine, chlorine, chloramide and copper(II) chloride, in an organic solvent such as acetic acid, at a temperature between 15° C. and the boiling point of the reaction medium. As alkali metal thiocyanate, it is preferable to use potassium thiocyanate. As alkali metal selenocyanate, it is preferable to use potassium selenocyanate.

The derivatives of formula (II), with the exception of 6-trifluoromethyl-1,2,3,4-tetrahydroquinoline, 2-methyl-6-trifluoromethoxy-1,2,3,4-tetrahydroquinoline, 6-trifluoromethyl-1,2,3,4-tetrahydroquinoxaline and 2-oxo- 7-trifluoromethyl-3,4-dihydroquinoxaline, are new and, as such, form part of the invention.

The compounds of formula (I) for which $R_2$ represents an alkyl radical may be prepared by alkylation of a corresponding compound of formula (I) for which $R_2$ represents a hydrogen atom.

This alkylation is carried out by any method which makes it possible to alkylate an imine functional group. Preferably, the procedure is carried out by means of a derivative Ra-X in which Ra represents an alkyl radical and X represents a reactive group such as a halogen atom (preferably chlorine, bromine or iodine) or a tosyloxy radical, in an inert organic solvent such as a lower aliphatic alcohol (ethanol, propanol or butanol for example), a ketone (acetone or methyl ethyl ketone for example) or dimethylformamide, in the presence of a base such as an alkali metal carbonate (potassium carbonate for example), at a temperature between 20° C. and the boiling point of the reaction medium.

The compounds of formula (I) for which —$R_3$—$R_4$—$R_5$— represents a chain of formula —$CH_2$—$CH_2$—$CH(R_8)$— and $R_8$ represents a hydroxyl radical may be obtained by reducing a corresponding compound of formula (I) for which —$R_3$—$R_4$—$R_5$— represents a chain of formula —$CH_2$—$CH_2$—CO—.

This reaction is carried out by any method which makes it possible to pass from a ketone to an alcohol. The procedure is generally carried out by means of sodium borohydride, in an alcohol such as methanol or ethanol, at a temperature of between 0 and 25° C.

The compounds of formula (I) for which —$R_3$—$R_4$—$R_5$— represents a chain of formula —$CH_2$—$CH_2$—SO—, —$CH_2$—$CH_2$—$SO_2$—, —$CH_2$—$CH(R_{13})$—SO— or —$CH_2$—$CH(R_{13})$—$SO_2$— may be prepared by oxidizing a corresponding compound of formula (I) for which —$R_3$—$R_4$—$R_5$— represents a chain of formula —$CH_2$—$CH_2$—S—, —$CH_2$—$CH_2$—Se— or —$CH_2$—$CH(R_{13})$—S—.

This oxidation is carried out according to known methods of oxidizing sulphur-containing derivatives as described by M. HUDLICKY, Oxidations in Organic Chemistry, ACS Monograph, 186, 252–263 (1990). For example, the procedure is carried out by the action of an organic peracid or a salt of such an acid (percarboxylic or persulphonic acid, in particular perbenzoic acid, 3-chloroperbenzoic acid, 4-nitroperbenzoic acid, peracetic acid, pertrifluoroacetic acid, performic acid or monoperphthalic acid) or inorganic peracids or a salt of such an acid (for example periodic or persulphuric acid), in an inert solvent such as a chlorinated solvent (chloroform or dichloromethane for example), at a temperature of between 0 and 25° C. It is also possible to use hydrogen peroxide and a periodate (sodium periodate for example), in an inert solvent such as a lower aliphatic alcohol, water or a mixture of these solvents, at a temperature of between 0 and 20° C. It is also possible to carry out the procedure by means of tert-butyl hydroperoxide in the presence of titanium tetraisopropoxide or oxoneo (potassium peroxymonosulphate) in a lower aliphatic alcohol or a water-alcohol mixture, at a temperature close to 25° C.

The compounds of formula (I) for which —$R_3$—$R_4$—$R_5$— represents a chain of formula —$CH(R_7)$—$CH_2$—$CH_2$- in which $R_7$ represents a radical —$CH_2$—$NR_{11}R_{12}$ and $R_2$ represents a hydrogen atom may be prepared by reacting an amine $HNR_{11}R_{12}$ for which $R_{11}$ and $R_{12}$ have the same meanings as in formula (I) with a derivative of formula:

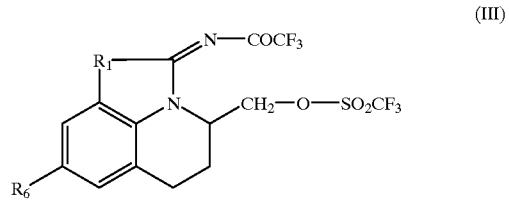

(III)

in which $R_1$ and $R_6$ have the same meanings as in formula (I) followed by hydrolysis to release the imine.

This reaction is generally carried out in an inert solvent such as a chlorinated solvent (chloroform or dichloromethane for example), at a temperature of between 0 and 50° C. The hydrolysis is preferably carried out by means of an alkali metal carbonate (potassium carbonate for example), in an aqueous-alcoholic medium, at a temperature close to 20° C.

The derivatives of formula (III) may be obtained from the corresponding compounds of formula (I) for which —$R_3$—$R_4$—$R_5$— represents a chain of formula —$CH(R_7)$—$CH_2$—$CH_2$— in which $R_7$ represents a radical —$CH_2OH$ and $R_2$ represents a hydrogen atom according to the following reaction scheme:

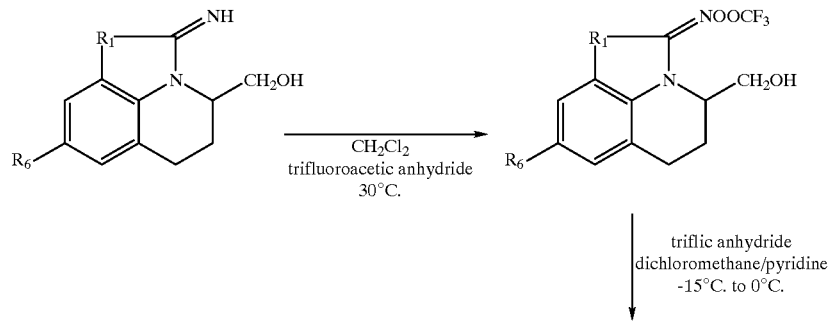

-continued

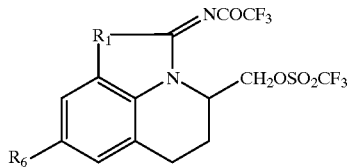

In these formulae, $R_1$ and $R_6$ have the same meanings as in formula (I).

The derivatives of formula (II) for which $R_6$ has the same meanings as in formula (I) and —$R_3$—$R_4$—$R_5$-represents a chain of formula —$CH_2$—$CH_2$—$CH_2$—, —$CH(R_7)$—$CH_2$—$CH_2$—, —$CH_2$—$CH_2$—$CH(R_8)$—, —$CH_2$—$CH(R_9)$—$CH_2$—, $R_7$ represents an alkyl, —$CH_2OH$, —$CH_2$—$NR_{11}R_{12}$ or —$CH_2$—$SO_2$-alk radical, $R_8$ represents an alkyl or —$CH_2$—$NR_{11}R_{12}$ radical and $R_9$ represents an alkyl radical may be obtained by hydrogenation of a derivative of formula:

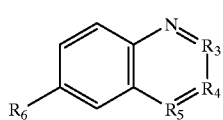

(IV)

in which $R_6$ has the same meanings as in formula (I) and =$R_3$—$R_4$=$R_5$— represents a chain of formula =$CH$—$CH$=$CH$—, —$C(R_7)$—$CH$=$CH$—, =$CH$—$CH$=$C$ ($R_8$)—, =$CH$—$C(R_9)$=$CH$—, $R_7$ represents an alkyl, —$CH_2OH$, —$CH_2$—$NR_{11}R_{12}$ or —$CH_2$—$SO_2$-alk radical, $R_8$ represents an alkyl or —$CH_2$—$NR_{11}R_{12}$ radical, $R_9$ represents an alkyl radical, $R_{11}$ and $R_{12}$ have the same meanings as in formula (I).

This hydrogenation is generally carried out either by means of hydrogen, at a pressure of 2 to 12 bar, in an inert organic solvent such as a lower aliphatic alcohol (methanol or ethanol for example) or tetrahydrofuran or a mixture of these solvents, in the presence of a hydrogenation catalyst such as platinum oxide, at a temperature close to 20° C., or by means of reducing agents such as sodium borohydride in the presence of nickel chloride or sodium cyanoborohydride, in an alcohol (methanol or ethanol for example), at a temperature close to 20° C.

The derivatives of formula (IV) for which =$R_3$—$R_4$=$R_5$— represents a chain of formula =$CH$—$CH$=$CH$—, =$C(R_7)$—$CH$=$CH$—, =$CH$—$C(R_9)$=$CH$—, $R_7$ represents an alkyl radical and $R_9$ represents an alkyl radical may be obtained from a 4-polyfluoroalkylaniline, 4-polyfluoroalkoxyaniline or 4-polyfluoroalkylthioaniline by application or adaptation of the methods described in the examples and of the methods described by G. JONES, Heterocyclic compounds, Quinolines, 32, part 1, Interscience, 93–318 (1977); J. Pharm. Sci., 68 (3), 336–8 (1979).

4-Polyfluoroalkylaniline, 4-polyfluoroalkoxyaniline and 4-polyfluoroalkylthioaniline are commercially available or may be obtained by application or adaptation of the methods described in J. Org.Chem., 29, 1 (1964), and in patents US 3,920,444, US 2,436,100, DE 2,606,982, EP 205821 and EP 546391.

The derivatives of formula (IV) for which =$R_3$—$R_4$=$R_5$— represents a chain of formula =$C(R_7)$—$CH$=$CH$— in which $R_7$ represents a radical —$CH_2$—$NR_{11}R_{12}$ may be obtained from a corresponding 2-methyl-6-polyfluoroalkylquinoline or 2-methyl-6-polyfluoroalkoxyquinoline or 2-methyl-6-polyfluoroalkylthioquinoline according to the following reaction scheme:

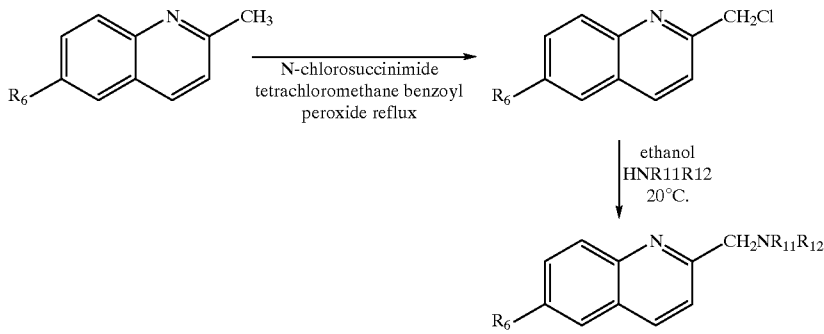

In these formulae, $R_6$, $R_{11}$ and $R_{12}$ have the same meanings as in formula (I).

The derivatives of formula (IV) for which $R_6$ has the same meanings as in formula (I) and =$R_3$—$R_4$=$R_5$— represents a chain of formula =$C(R_7)$—$CH$=$CH$—, $R_7$ represents a radical —$CH_2OH$ may be obtained by reacting acetic anhydride with 2-methyl-6-polyfluoroalkylquinoline 1-oxide or 2-methyl-6-polyfluoroalkoxyquinoline 1-oxide or 2-methyl-6-polyfluoroalkylthioquinoline 1-oxide at the boiling point of the reaction medium, followed by hydrolysis, for example, by the action of a dilute solution of an alkali metal hydroxide, in a solvent such as a water-dioxane mixture, at the boiling point of the reaction medium.

The derivatives of formula (IV) for which =$R_3$—$R_4$=$R_5$— represents a chain of formula =$C(R_7)$—$CH$=$CH$— and $R_7$ represents a radical —$CH_2$—$SO_2$-alk may be obtained by reacting a 6-polyfluoroalkylquinoline 1-oxide, 6-polyfluoroalkoxyquinoline 1-oxide or 6-polyfluoroalkylthioquinoline 1-oxide and acetic anhydride with a derivative alk-$SO_2$—$CH_2$—$COCH_3$ in which alk represents an alkyl radical, in ethylene glycol dimethyl ether, at a temperature varying from 0 to 80° C.

2-Methyl-6-polyfluoroalkylquinoline 1-oxide, 2-methyl-6-polyfluoroalkoxyquinoline 1-oxide or 2-methyl-6-polyfluoroalkylthioquinoline 1-oxide and 6-polyfluoroalkylquinoline 1-oxide, 6-polyfluoroalkoxyquinoline 1-oxide or 6-polyfluoroalkylthioquinoline 1-oxide may be obtained by oxidizing the corresponding quinolines, by means of an oxidizing agent such as 3-chloroperbenzoic acid, in an inert organic solvent such as a chlorinated solvent (chloroform or dichloromethane for example), at a temperature close to 20° C.

The derivatives of formula (IV) for which =$R_3$—$R_4$=$R_5$— represents a chain of formula =C($R_7$)—CH=CH— or =CH—CH=C($R_8$)— and $R_7$ and $R_8$ represent —$CH_2$—$NR_{11}R_{12}$ radicals may be obtained by reacting an amine $HNR_{11}R_{12}$ in which $R_{11}$ and $R_{12}$ have the same meanings as in formula (I) with a corresponding derivative of formula (IV) for which =$R_3$—$R_4$=$R_5$— represents a chain of formula =C($R_7$)—CH=CH— or =CH—CH=C($R_8$)— and $R_7$ and $R_8$ represent —$CH_2OH$ radicals in the form of a reactive derivative.

This reaction is generally carried out in an inert organic solvent such as an ether (tetrahydrofuran or dioxane for example), a chlorinated solvent (chloroform for example), in the presence of a base, at a temperature between 20° C. and the boiling point of the reaction medium. As a reactive derivative, chloride, tosylate or mesylate may be mentioned.

The derivatives of formula (IV) for which =$R_3$—$R_4$=$R_5$— represents a chain of formula =CH—CH=C($R_8$)— and $R_8$ represents an alkyl radical may be obtained by application or adaptation of the method described by KRAINER et al., Chem. Heterocycl. Compd. 9, 217–219 (1973) or Khim. Geterotsikl. Soedin., 9 (2), 235–238 (1973).

The derivatives of formula (II) for which —$R_3$—$R_4$—$R_5$— represents a chain of formula —$CH_2$—$CH_2$—CH($R_8$)— and $R_8$ represents a radical —$CH_2$—OH, thienyl, furyl, phenyl or phenyl substituted with a substituent chosen from halogen atoms and alkyl or alkoxy radicals or -$NR_{11}R_{12}$ in which $R_{11}$ and $R_{12}$ represent hydrogen atoms or $R_{11}$ represents a radical —CO-alk and $R_{12}$ represents an alkyl radical or $R_{11}$ represents a hydrogen atom and $R_{12}$ represents an alkyl radical or $R_{11}$ and $R_{12}$ form with the nitrogen atom to which they are attached a saturated or unsaturated 5- or 6-membered heterocycle optionally containing another heteroatom chosen from nitrogen, oxygen and sulphur and optionally substituted with an alkyl, phenyl, halophenyl or phenylalkyl radical may be obtained by reacting a derivative of formula:

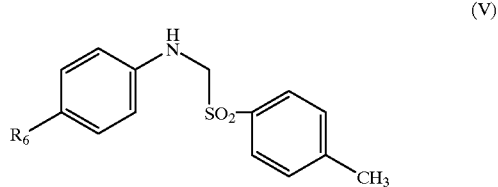

(V)

in which $R_6$ has the same meanings as in formula (I) with a derivative Rb—CH=$CH_2$ for which Rb represents a radical —$CH_2$—OH, thienyl, furyl, phenyl or phenyl substituted with a substituent chosen from halogen atoms and alkyl and alkoxy radicals or —$NR_{11}R_{12}$ in which either $R_{11}$ and $R_{12}$ form with the nitrogen atom to which they are attached a phthalimido radical followed by hydrolysis in order to obtain the derivative for which $R_{11}$ and $R_{12}$ are hydrogen atoms, or $R_{11}$ represents a radical —CO-alk and $R_{12}$ represents an alkyl radical optionally followed by hydrolysis in order to obtain the derivatives for which $R_{11}$ represents a hydrogen atom and $R_{12}$ represents an alkyl radical, or $R_{11}$ and $R_{12}$ form with the nitrogen atom to which they are attached a saturated or unsaturated 5- or 6-membered heterocycle optionally containing another heteroatom chosen from nitrogen, oxygen and sulphur and optionally substituted with an alkyl, phenyl, halophenyl or phenylalkyl radical.

This reaction is generally carried out in an inert organic solvent such as a chlorinated solvent (chloroform or dichloromethane for example), in the presence of a Lewis acid such as tin tetrachloride, titanium tetrachloride, boron trifluoride etherate, at a temperature varying from –80° C. to a temperature close to 20° C. The hydrolysis of the phthalimido and of the acylated derivative is generally carried out by means of an acid such as hydrochloric acid, in an aqueous medium, at a temperature between 20° C. and the boiling point of the reaction medium.

The derivatives of formula (V) may be obtained by the action of formaldehyde and sodium p-toluenesulphinate and then of a 4-polyfluoroalkylaniline, 4-polyfluoroalkoxyaniline or 4-polyfluoroalkylthioaniline, in an aqueous medium, in the presence of hydrochloric acid, at a temperature close to 25° C.

The Rb—CH=$CH_2$ derivatives are commercially available or may be obtained by application or adaptation of the methods described by ABARCA et al., Tetrahedron, 43 (1), 269–274 (1987); NEGISHI et al., Heterocycles, 18 spec. Issue, 117–22 (1982); REIJENDAM et al., Tetrahedron, 26, 1291 (1970); HACHIHAMA et al., Chem. Abstr., 44, 9720f (1950); TAGAKI et al., Tetrahedron Lett., 2587 (1974); Chem. Abstr., 65, 18503e (1966); Chem. Abstr., 71, 49326r (1969); Chem. Abstr., 63, 18119f (1965) and Chem. Abstr., 58, 8083b.

The derivatives of formula (II) for which —$R_3$—$R_4$—$R_5$— represents a chain of formula —$CH_2$—$CH_2$—CH($R_8$)— and $R_8$ represents a radical —$NR_{11}R_{12}$ in which $R_{11}$ represents a hydrogen atom and $R_{12}$ represents a radical —CO-alk may be obtained by acylation of a corresponding derivative of formula (II) for which $R_{11}$ and $R_{12}$ represent hydrogen atoms.

This reaction is generally carried out by means of an acyl halide and, in particular, of an acyl chloride or bromide, in an inert solvent such as tetrahydrofuran, at a temperature between 20° C. and the boiling point of the reaction medium.

The derivatives of formula (II) for which —$R_3$—$R_4$—$R_5$— represents a chain of formula —$CH_2$—$CH_2$—CH($R_8$)— and $R_{11}$ represents a radical —$NR_{11}R_{12}$ in which $R_{11}$ represents an alkyl radical (2-6C) and $R_{12}$ represents an alkyl radical may be obtained by reducing a corresponding derivative of formula (II) for which $R_{12}$ represents an alkyl radical and $R_{11}$ represents a radical —CO-alk.

This reduction is generally carried out by means of the borane-methyl sulphide complex, in tetrahydrofuran, at a temperature close to 20° C.

The derivatives of formula (II) for which —$R_3$—$R_4$—$R_5$— represents a chain of formula —$CH_2$—$CH_2$—CH($R_8$)— in which $R_8$ represents a radical —$NR_{11}R_{12}$ for which $R_{11}$ and $R_{12}$ form with the nitrogen atom to which they are attached pyrrolidine, morpholine, piperidine or piperazine may also be obtained by reducing a derivative of formula:

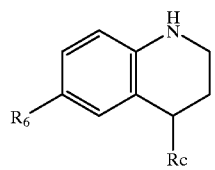

in which Rc represents a 2-oxopyrrolidin-1-yl, 3-oxomorpholin-4-yl, 2-oxopiperidin-1-yl or 2-oxopiperazin-1-yl and $R_6$ has the same meanings as in formula (I).

This reduction is generally carried out by means of the borane-methyl sulphide complex, in tetrahydrofuran, at a temperature close to 20° C.

The derivatives of formula (VI) are themselves obtained according to the process mentioned above from a derivative of formula (V) and from a derivative Rb—CH=CH$_2$ for which Rb represents a 2-oxopyrrolidin-1-yl, 3-oxomorpholin-4-yl, 2-oxopiperidin-1-yl or 2-oxopiperazin-1-yl radical.

The derivatives of formula (II) for which —$R_3$—$R_4$—$R_5$— represents a chain of formula —$CH_2$—$CH_2$—CH($R_8$)— in which $R_8$ represents a radical —$NR_{11}R_{12}$, $R_{12}$ represents a hydrogen atom or an alkyl radical and $R_{11}$ represents a radical —CO—$CF_3$ may be obtained by reacting trifluoroacetic anhydride with a corresponding derivative of formula (II) for which —$R_3$—$R_4$—$R_5$-represents a chain of formula —$CH_2$—$CH_2$—CH($R_8$)— in which $R_8$ represents a radical —$NR_{11}R_{12}$, $R_{12}$ represents a hydrogen atom or an alkyl radical and $R_{11}$ represents a hydrogen atom.

This reaction is generally carried out in pyridine, at a temperature close to −30° C.

The derivatives of formula (II) for which —$R_3$—$R_4$—$R_5$— represents a chain of formula —$CH_2$—$CH_2$—CH($R_8$)— in which $R_8$ represents a radical —$NR_{11}R_{12}$ or —S-alk may be obtained by reacting a derivative $HR_8$ for which $R_8$ represents a radical —$NR_{11}R_{12}$ or —S-alk, $R_{11}$, $R_{12}$ and alk having the same meanings as in formula (I) with a derivative of formula:

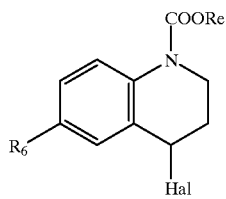

in which $R_6$ has the same meanings as in formula (I), Hal represents a halogen atom and preferably a chlorine or bromine atom and Re represents a tert-butyl radical followed by deprotection of the cyclic nitrogen.

When $R_8$ represents a radical —$NR_{11}R_{12}$, this reaction is generally carried out in an alcohol (ethanol, methanol for example), at a temperature close to 20° C. When $R_8$ represents a radical —S-alk, this -reaction is generally carried out in dimethylformamide, in the presence of an alkali metal hydride (preferably sodium hydride), at a temperature of between 0 and 25° C. The deprotection is preferably carried out by means of trifluoroacetic acid, in dichloromethane, at a temperature close to 20° C.

The derivatives of formula (VII) may be obtained by halogenation of a corresponding tert-butyl 6-polyfluoroalkyl-1,2,3,4-tetrahydroquinoline-1-carboxylate or tert-butyl 6-polyfluoroalkoxy-1,2,3,4-tetrahydroquinoline-1-carboxylate or tert-butyl 6-polyfluoroalkylthio-1,2,3,4-tetrahydroquinoline-1-carboxylate.

This halogenation is carried out by any method known to persons skilled in the art which does not modify the remainder of the molecule. For example, it is possible to brominate by means of N-bromosuccinimide, in an inert solvent such as a chlorinated solvent such as carbon tetrachloride, in the presence of benzoyl peroxide, at a temperature close to 20° C.

The derivatives of formula (II) for which —$R_3$—$R_4$—$R_5$— represents a chain of formula —$CH_2$—$CH_2$—CH($R_8$)— in which $R_8$ represents a radical —SO-alk or —$SO_2$-alk may be obtained by oxidizing a corresponding derivative of formula (II) for which —$R_3$—$R_4$—$R_5$— represents a chain of formula —$CH_2$—$CH_2$—CH($R_8$)— in which $R_8$ represents a radical —S-alk.

This oxidation is carried out as mentioned above for the preparation of the compounds of formula (I) for which —$R_3$—$R_4$—$R_5$— represents a chain of formula —$CH_2$—$CH_2$—SO—, —$CH_2$—$CH_2$—$SO_2$, —$CH_2$—CH($R_{13}$)—SO— or —$CH_2$—CH ($R_{13}$)—$SO_2$—.

The derivatives of formula (II) for which —$R_3$—$R_4$—$R_5$— represents a chain of formula —$CH_2$—$CH_2$—S-l —$CH_2$—$CH_2$—O—, —$CH_2$—$CH_2$—Se or —$CH_2$—$CH_2$—N($R_{10}$)— may be obtained by reducing a derivative of formula:

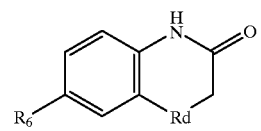

in which Rd RR represents an oxygen, sulphur or selenium atom or N($R_{11}$) and $R_6$ and $R_{10}$ have the same meanings as in formula (I).

This reaction is carried out by means of a reducing agent such as lithium tetrahydroaluminate, in an inert organic solvent such as tetrahydrofuran, at a temperature close to 20° C.

The derivatives of formula (VIII) may be obtained from a derivative of formula:

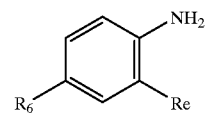

in which Re represents an OH, SH, SeH or NH($R_{10}$) radical, $R_6$ and $R_{10}$ have the same meanings as in formula (I), by application or adaptation of the methods described in the examples and by X. HUANG, Synthesis, 851–852 (1984), W. C. LUMMA et al., J. Med. Chem., 24, 93–101 (1981) and E. J. JACOBSEN et al., J. Med. Chem., 39, 158–175 (1996).

The derivatives of formula (IX) may be obtained by application or adaptation of the methods described by R. BELCHER et al., J. Chem. Soc., 3846 (1954); B. L. MYLARY, J. Med. Chem., 34, 108–122 (1991); D. W. COMBS et al., J. Med. Chem., 35, 172–176 (1992), W. C. LUMMA et al., J. Med. Chem., 24, 93–101 (1981) and A. V. ZEIGER et al., J. Org. Chem., 42 (3), 542 (1977).

The derivatives of formula (II) for which —R$_3$—R$_4$—R$_5$— represents a chain of formula —CH$_2$—CH$_2$—CO— may be obtained by oxidizing a corresponding derivative of formula (II) for which —R$_3$—R$_4$—R$_5$— represents a chain of formula —CH$_2$—CH$_2$—CH$_2$—.

This reaction is generally carried out by means of tert-butyl hydroperoxide and chromic anhydride in aqueous solution, in an inert solvent such as a chlorinated solvent (dichloromethane or chloroform for example), at a temperature close to 20° C. Preferably, the nitrogen of the corresponding derivative of formula (II) for which —R$_3$—R$_4$—R$_5$— represents a chain of formula —CH$_2$—CH$_2$—CH$_2$ is protected beforehand.

The derivatives of formula (II) for which —R$_3$—R$_4$—R$_5$— represents a chain of formula —CH$_2$—CO—N(R$_{10}$)— may be obtained by reacting ethyl glycinate with a derivative of formula:

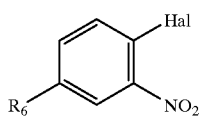

(X)

in which R$_6$ has the same meanings as in formula (I) and Hal represents a halogen atom and in particular fluorine followed by a reduction-cyclization. When R$_{10}$ represents an alkyl radical, the alkylation is carried out before the reduction-cyclization.

This reaction is carried out at a temperature between 20° C. and the boiling point of the reaction medium. The reduction-cyclization is carried out in a single step by treatment with tin in the presence of hydrochloric acid, in aqueous ethanol, at the boiling point of the reaction medium or with Raney nickel. The alkylation is carried out by the methods described above for the preparation of the compounds of formula (I) for which R$_2$ represents an alkyl radical.

The derivatives of formula (X) may be obtained by application or adaptation of the method described in Chem. Abstr. 113, 233655.

The derivatives of formula (II) for which —R$_3$—R$_4$—R$_5$— represents a chain of formula —CH$_2$—CO—N(R$_{11}$)— may also be obtained according to the following reaction scheme:

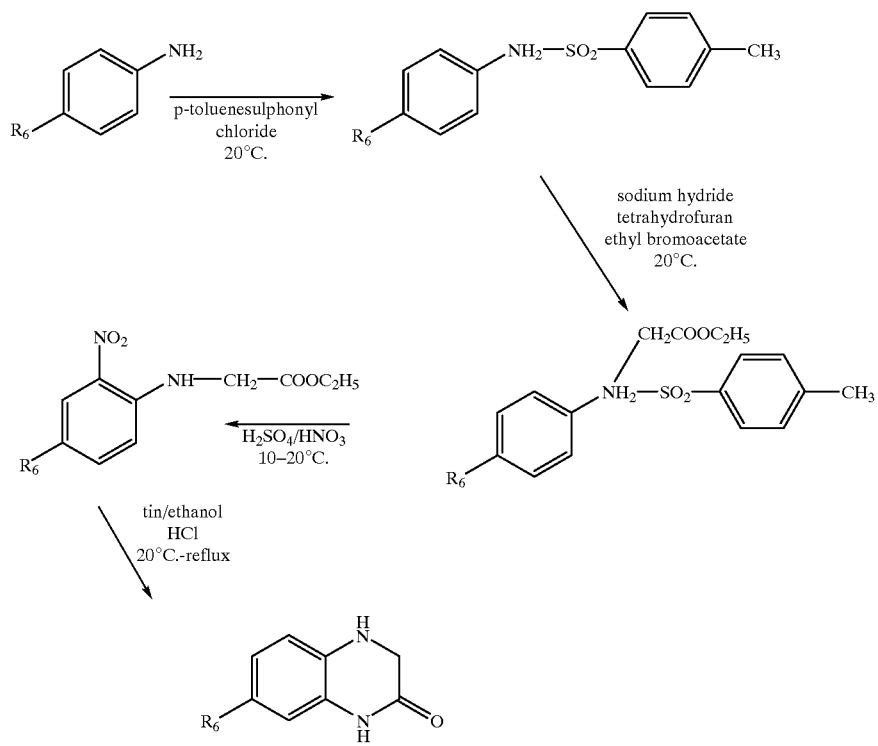

In these formulae, R$_6$ has the same meanings as in formula (I).

The derivatives of formula (II) for which —R$_3$—R$_4$—R$_5$— represents a chain of formula —CH$_2$—CF$_2$—CH$_2$— may be obtained by reducing a corresponding derivative of formula (II) for which —R$_3$—R$_4$—R$_5$— represents a chain of formula —CH$_2$—CF$_2$—CH (OH)—.

This reaction is generally carried out by means of triethylsilane and trifluoroacetic acid, at a temperature close to 20° C.

The derivatives of formula (II) for which —R$_3$—R$_4$—R$_5$— represents a chain of formula —CH$_2$—CF$_2$—CH (OH)— or —CH$_2$—CH(R$_{13}$)—S in which R$_{13}$ represents an alkyl radical may be obtained by reducing a derivative of formula:

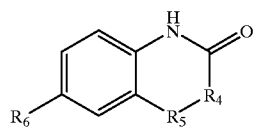

in which $R_6$ has the same meanings as in formula (I), $-R_4-R_5-$ represents a radical $-CF_2-CH(OH)-$ or $-CH(alk)-S$ and alk represents an alkyl radical.

This reaction is generally carried out by means of the borane-methyl sulphide complex, in toluene, at the boiling point of the reaction medium.

The derivatives of formula (XI) may be obtained according to the following reaction schemes:

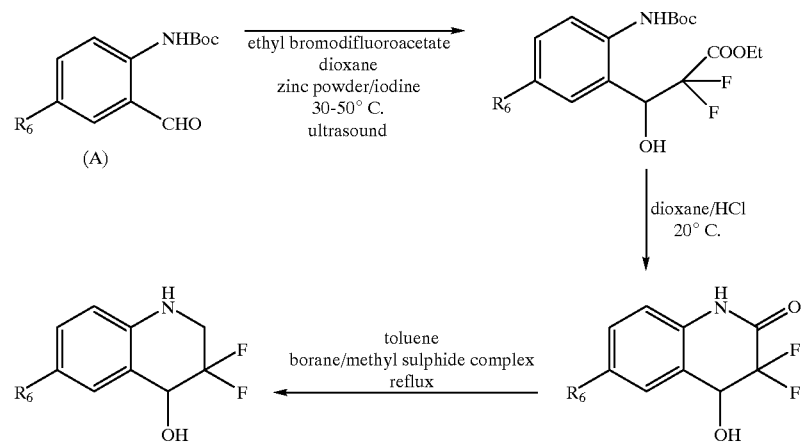

in these formulae, $R_6$ has the same meanings as in formula (I), Et represents ethyl and Boc represents a tert-butoxycarbonyl radical,

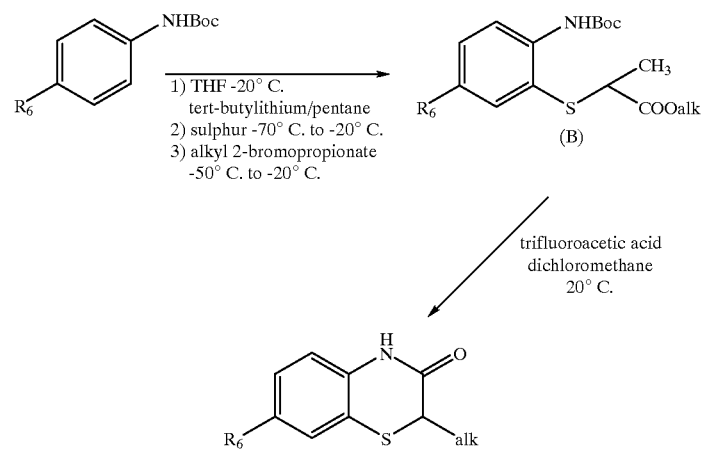

in these formulae, $R_6$ has the same meanings as in formula (I), alk represents an alkyl radical and Boc represents a tert-butoxycarbonyl radical.

The aldehydes (A) may be obtained by application or adaptation of the method described in Chem. Abstr., 107, 39815x.

The derivatives of formula (II) for which $-R_3-R_4-R_5-$ represents a chain $-CH_2-CH(R_{13})-S-$ or $-CH_2-CH(R_9)-CH_2-$ for which $R_{13}$ and $R_9$ represent a radical $-CH_2OH$ may be obtained by reducing a derivative of formula:

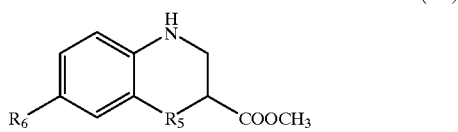

in which $R_6$ has the same meanings as in formula (I) and $R_5$ represents a sulphur atom or a $-CH_2-$ radical.

This reaction is preferably carried out by means of the borane-dimethyl sulphide complex, in an inert solvent such as toluene or tetrahydrofuran, at the boiling point of the reaction medium.

The derivatives of formula (XII) may be obtained according to the following reaction schemes:

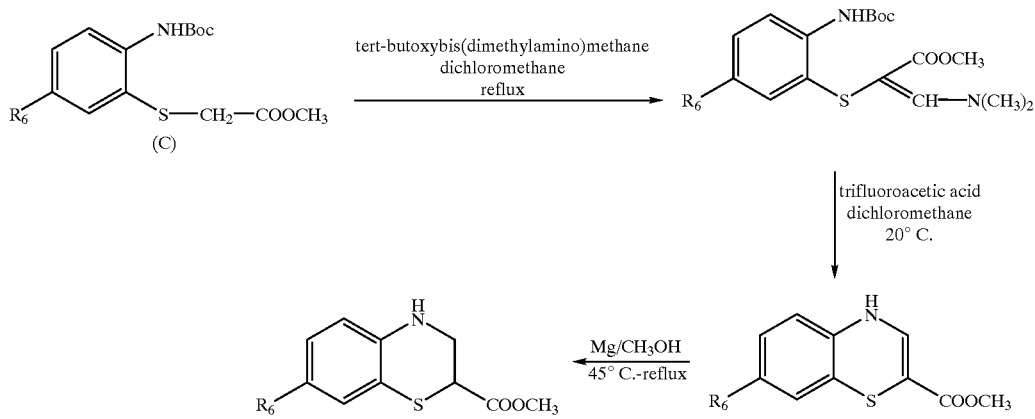

in these formulae, $R_6$ has the same meanings as in formula (I) and Boc represents a tert-butoxycarbonyl radical.

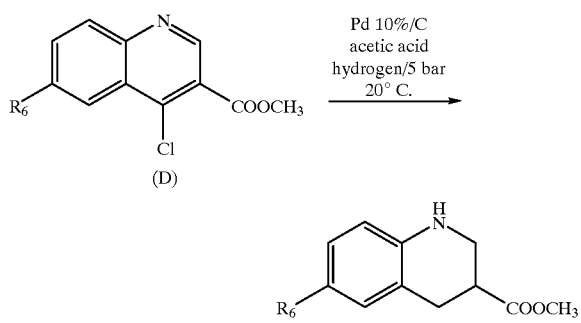

in these formulae, $R_6$ has the same meanings as in formula (I).

The derivatives of formula (c) may be obtained as mentioned above for the derivatives of formula (B) using an alkyl bromoacetate instead of alkyl 2-bromopropionate.

The derivatives of formula (D) may be prepared by application or adaptation of the method described in J. Med. Chem., 22 (7), 816–823 (1979).

It is understood for persons skilled in the art that, to carry out the processes according to the invention described above, it may be necessary to introduce groups for protecting amino functional groups so as to avoid side reactions. In particular, the procedure is carried out according to the methods described by T. W. Greene, Protective Groups in Organic Synthesis, A. Wiley Interscience Publication (1981), or by Mc Omie, Protective Groups in Organic Chemistry, Plenum Press (1973). The amino functional groups may, for example, be protected by phthalimido, methoxycarbonyl, ethoxycarbonyl, t-butoxycarbonyl, allyloxycarbonyl, vinyloxycarbonyl, trichloroethoxycarbonyl, trichloroacetyl, trifluoroacetyl, chloroacetyl, trityl, benzhydryl, benzyl, allyl, formyl, acetyl or benzyloxycarbonyl radicals or their substituted derivatives or in the form of tert-butyl or methyl carbamates and then regenerated by means of trifluoroacetic acid or hydrochloric acid in tetrahydrofuran or of benzyl carbamates and then regenerated by hydrogenation after having used the process according to the invention.

The reaction mixtures obtained by the various procedures described above are treated according to conventional physical methods (evaporation, extraction, distillation, chromatography and crystallization for example) or conventional chemical methods (formation of salts for example).

The enantiomers of the compounds of formula (I) containing at least one asymmetric site may be obtained by synthesis from chiral precursors or by resolution of the racemates, for example, by chromatography on a chiral column according to W. H. PIRKLE et al., asymmetric synthesis, vol 1, Academic Press (1983).

The compounds of formula (I) in the form of a free base may optionally be converted to addition salts with an inorganic or organic acid, by the action of such an acid in an organic solvent such as an alcohol, a ketone, an ether or a chlorinated solvent.

As examples of pharmaceutically acceptable salts, there may be mentioned the addition salts with inorganic or organic acids such as acetate, propionate, succinate, benzoate, fumarate, maleate, oxalate, methanesulphonate, isethionate, theophyllineacetate, salicylate, methylene-bis-g-oxynaphthoate, hydrochloride, sulphate, nitrate and phosphate.

The compounds of formula (I) exhibit advantageous pharmacological properties. These compounds are anticonvulsants and interfere with glutamatergic transmission and are therefore useful for the treatment or prevention of all ischaemias (such as focal or global ischaemia) following cerebrovascular accidents such as thromboembolic and haemorrhagic stroke, cardiac arrest, arterial hypotension, cardiac, vascular or pulmonary surgery or severe hypoglycaemia. They are also useful in the treatment of the effects caused by anoxia, whether it is perinatal or subsequent to drowning, a high pressure or cerebrospinal lesions. These compounds may also be used to treat or prevent the development of neurodegenerative diseases, of HUNTINGDON's chorea, of ALZHEIMER's disease and other dementias, of amyotrophic lateral sclerosis or of other motor neuron diseases, of olivopontocerebellar atrophy and of PARKINSON's disease. These compounds may also be used against epileptogenic and/or convulsive manifestations, for the treatment of cerebral or spinal traumas, of traumas linked to degeneration of the inner ear (R. PUJOL et al., Neuroreport, 3, 299–302 (1992)) or of the retina (J. L. MONSINGER et al., Exp. Neurol., 113, 10–17 (1991)), of tinnitus, of anxiety (KEHNE et al., Eur. J. Pharmacol., 193, 283 (1991)), of depression (TRULLAS et al., Eur. J. Pharmacol., 185, 1, (1990)), of schizophrenia (REYNOLDS, TIPS, 13, 116 (1992)), of TOURETTE's syndrome, of hepatic encephalopathies, of sleep disorders, of attention deficit disorders, of disorders of hormonal conditions (excess secretion of GH or LH, secretion of corticosterone), as analgesics (DICKENSON et al., Neurosc. Letters, 121, 263 (1991)), anti-inflammatory agents (SLUTA et al., Neurosc. Letters, 149, 99–102 (1993)), antianorectics (SORRELS et al., Brain Res., 572, 265 (1992)), antimigraine drugs, antiemetics and to treat poisoning by neurotoxins or other substances which are NMDA or AMPA receptor agonists, as well as neurological disorders associated with viral diseases such as viral meningitis and encephalitis, AIDS (LIPTON et al., Neuron 7, 111 (1991)), rabies, measles and tetanus (BAGETTA et al., Br. J. Pharmacol., 101, 776 (1990)). These compounds are also useful for the prevention of, tolerance to and dependency on the symptoms of withdrawal from drugs and alcohol, and of inhibition of addiction to and of dependency on opiates, barbiturates, amphetamine and benzodiazepines. They may also be used in the treatment of deficiencies linked to mitochondrial abnormalities such as mitochrondrial myopathy, LEBER's syndrome, WERNICKE's encephalopathy, RETT's syndrome, homocysteinaemia, hyperprolinaemia, hydroxybutyric-aminoaciduria, saturnine encephalopathy (chronic lead poisoning) and sulphite oxidase deficiency.

The activity of these products as anticonvulsant was determined in mice according to the maximum electroshock method. White CD1 mice are treated intravenously with the test compounds in saline medium 10 minutes before being subjected to an electric shock (75 mA; duration 0.04 second) by means of ocular electrodes. Normally, this shock produces a tonic convulsion in untreated mice, characterized by extension of the limbs. If tonic convulsion does not occur, the animal is considered to be protected. In this test, the compounds of formula (I) have an ED50 of less than or equal to 6 mg/kg.

The activity of these products as antiglutamate was determined on the convulsions induced by glutamate according to a technique inspired by that of I. P. LAPIN, J. Neural. Transmission, 54, 229–238 (1982); the glutamate being injected by the intracerebroventricular route according to a technique inspired by that of R. CHERMAT and P. SIMON, J. Pharmacol. (Paris), 6, 489–492 (1975). Their $ED_{50}$ is less than 10 mg/kg.

The compounds of formula (I) have a low toxicity. Their $LD_{50}$ is greater than 15 mg/kg by the IV route in mice.

For medicinal use, the compounds of formula (I) may be used as such or in the form of pharmaceutically acceptable salts, that is to say which are nontoxic at the applicable doses.

Particularly advantageous are the compounds for which
$R_1$ represents a sulphur or selenium atom,
$R_2$ represents a hydrogen atom or an alkyl radical,
—$R_3$—$R_4$—$R_5$— represents a chain of formula —$CH_2$—$CH_2$—$CH_2$—, —$CH(R_7)$—$CH_2$—$CH_2$—, —$CH_2$—$CF_2$—$CH(OH)$—, —$CH_2$—$CH_2$—$CH(R_8)$—, —$CH_2$—$CH_2$—$CO$—, —$CH_2$—$CH_2$—$S$—, —$CH_2$—$CH_2$—$SO$—, —$CH_2$—$CH_2$—$SO_2$—,
$R_6$ represents a polyfluoroalkyl, polyfluoroalkoxy or polyfluoroalkylthio radical,
$R_7$ represents an alkyl, —$CH_2OH$ or —$CH_2NR_{11}R_{12}$ radical,
$R_8$ represents an —$NR_{11}R_{121}$—$SO_2$-alk-, —$SO$-alk- or phenyl radical,
$R_{11}$ represents a hydrogen atom or an alkyl or acyl radical,
$R_{12}$ represents a hydrogen atom or an alkyl radical, or alternatively $R_{11}$ and $R_{12}$ form with the nitrogen atom to which they are attached a saturated or unsaturated 5- or 6-membered heterocycle optionally containing another heteroatom chosen from nitrogen, oxygen or sulphur.

The following compounds may be mentioned among the particularly advantageous compounds:

2-Imino-8-trifluoromethoxy-5,6-dihydro-2H,4H-thiazolo[5,4,3-ij]quinoline,
2-Imino-8-trifluoromethyl-5,6-dihydro-2H,4H-thiazolo[5,4,3-ij]quinoline,
(R,S)-2-Imino-4-methyl-8-trifluoromethyl-5,6-dihydro-2H,4H-thiazolo[5,4,3-ij]quinoline and its enantiomers,
2-Imino-8-trifluoromethoxy-2H,4H-thiazolo[5,4,3-ij]quinolin-6-one,
2-Imino-8-trifluoromethoxy-4,5-dihydro-2H-thiazolo[3,4,5-de][1,4]benzothiazine 6,6-dioxide,
(R,S)-2-Imino-8-trifluoromethoxy-4,5-dihydro-2H-thiazolo[3,4,5-de][1,4]benzothiazine 6-oxide and its enantiomers,
(R,S)-2-Imino-8-trifluoromethyl-4,5-dihydro-2H-thiazolo[3,4,5-de][1,4]benzothiazine 6-oxide and its enantiomers,
2-Imino-8-trifluoromethyl-4,5-dihydro-2H-thiazolo[3,4,5-de][1,4]benzothiazine,
(R,S)-2-Imino-6-phenyl-8-trifluoromethyl-5,6-dihydro-2H,4H-thiazolo[5,4,3-ij]quinoline and its enantiomers,
2-Imino-8-trifluoromethoxy-4,5-dihydro-2H-thiazolo[3,4,5-de][1,4]-benzoxazine,
(R,S)-2-Imino-8-trifluoromethyl-5,6-dihydro-2H,4H-thiazolo[5,4,3-ij]quinoline-4-methanol and its enantiomers,
(R,S)-5,5-Difluoro-6-hydroxy-2-imino-8-trifluoromethyl-5,6-dihydro-2H,4H-thiazolo[5,4,3-ij]quinoline and its enantiomers,
(R,S)-Ethylmethyl(2-imino-8-trifluoromethyl-5,6-dihydro-2H,4H-thiazolo[5,4,3-ij]quinol-4-ylmethyl)amine and its enantiomers,
2-Imino-8-trifluoromethyl-5,6-dihydro-2H,4H-selenazolo[5,4,3-ij]quinoline
(R,S)-2-Imino-6-ethylsulphinyl-8-trifluoromethyl-5,6-dihydro-2H,4H-thiazolo[5,4,3-ij]quinoline and its enantiomers,
(R,S)-2-Imino-6-ethylsulphonyl-8-trifluoromethyl-5,6-dihydro-2H,4H-thiazolo[5,4,3-ij]quinoline and its enantiomers and their salts.

The following examples illustrate the invention without limiting it.

EXAMPLE 1

1.6 g of bromine diluted in 5 ml of acetic acid are added dropwise over 10 minutes, at a temperature close to 20° C., to a solution of 3.9 g of potassium thiocyanate and 2.1 g of 6-trifluoromethoxy-1,2,3,4-tetrahydroquinoline in 20 ml of acetic acid. The reaction mixture is stirred for 20 hours at the same temperature, poured over ice, alkalinized with a solution of aqueous ammonia at 20% and extracted with three times 100 ml of ethyl acetate. The organic phases are combined, washed with 100 ml of distilled water, dried over magnesium sulphate and concentrated to dryness under reduced pressure (2 kPa) at 40° C. The crude product is chromatographed on a silica gel column, eluting with ethyl acetate, and gives 0.6 g of a white solid. The latter is redissolved in the minimum amount of ethanol and then supplemented with an excess of hydrochloric isopropanol (about 5 N). After recrystallization from ethanol, 0.52 g of 2-imino-8-trifluoromethoxy-5,6-dihydro-2H,4H-thiazolo[5,4,3-ij]quinoline hydrochloride is thus obtained in the form a white solid melting above 260° C. with decomposition [$^1$H NMR spectrum in DMSO-$d_6$, T=300K, δ in ppm (250 MHz): 2.15 (2H, m, $CH_2$), 2.95 (2H, t, J=6 Hz, $CH_2$-aryl), 4.15 (2H, t, J=6 Hz, $NCH_2$), 7.45 (1H, s, arom. CH), 8.00 (1H, s, arom. CH), 10.50 (2H, broad s, NH.HCl)].

6-Trifluoromethoxy-1,2,3,4-tetrahydroquinoline may be prepared in the following manner: 2.13 g of 6-trifluoromethoxyquinoline with 0.4 g of platinum oxide in 25 ml of methanol are hydrogenated at a temperature close to 20° C. at a pressure of 5 to 3 bar for 1.5 hours. After filtration of the reaction medium, the organic phase is concentrated under reduced pressure (2 kPa) at 40° C., to give a slightly brown oil. The latter is dissolved in an excess of hydrochloric isopropanol (about 5 N) and then concentrated again under vacuum to provide 1 g of 6-trifluoromethoxy-1,2,3,4-tetrahydroquinoline hydrochloride in the form of a white solid melting at 145° C. with decomposition. By treating the hydrochloride with a dilute solution of sodium hydroxide and extracting with ethyl acetate, the base is obtained in the form of an oil.

6-Trifluoromethoxyquinoline may be prepared in the following manner: a mixture of 17.7 g of 4-trifluoromethoxyaniline, 33.7 g of sodium 3-nitrobenzenesulphonate, 6 g of iron sulphate heptahydrate, 10 g of boric acid, 250 ml of glycerol and 60 ml of concentrated sulphuric acid is heated at a temperature close to 150° C. for 1 hour 20 minutes. The reaction mixture is then poured over ice, alkalinized with a concentrated sodium hydroxide solution and then extracted with three times 300 ml of dichloromethane. The organic phase is washed with 100 ml of water, dried over magnesium sulphate and then concentrated under reduced pressure (2 kPa). The evaporation residue is chromatographed on a silica gel column, eluting with a mixture of cyclohexane and ethyl acetate (70-30 by volume) to provide 15 g of 6-trifluoromethoxyquinoline in the form of a light-coloured oil [$^1$H NMR spectrum in CDCl$_3$, T=300K, δ in ppm (20 MHz): 7.40 (1H, dd, J=3 and 7 Hz, arom. CH), 7.55 (1H, d, J=8 Hz, arom. CH), 7.60 (1H, s, arom. CH), 8.10 (1H, dd, J=7 and 1 Hz, arom. CH), 8.12 (1H, d, J=8 Hz, arom. CH), 8.90 (1H, dd, J=3 and 1 Hz, arom. CH)].

EXAMPLE 2

The procedure is carried out as in Example 1, but starting with 3.5 g of bromine diluted in 10 ml of acetic acid, 5 g of potassium thiocyanate and 4.4 g of 6-trifluoromethyl-1,2,3,4-tetrahydroquinoline in 40 ml of acetic acid. 2.8 g of 2-imino-8-trifluoromethyl-5,6-dihydro-2H,4H-thiazolo[5,4,3-ij]quinoline hydrochloride are thus obtained in the form of a white solid melting above 260° C. with decomposition [$^1$H NMR spectrum in DMSO-d$_6$, T=300K, δ in ppm (300 MHz): 2.20 (2H, m, CH$_2$), 3.00 (2H, t, J=6 Hz, CH$_2$-aryl), 4.15 (2H, t, J=6 Hz, NCH$_2$), 7.75 (1H, s, arom. CH), 8.30 (1H, s, arom. CH), 10.80 (2H, broad s, NH.HCl)].

6-Trifluoromethyl-1,2,3,4-tetrahydroquinoline may be prepared as described in J. Chem. Soc. Perkin Trans., 1, (9), 1933–9 (1980).

EXAMPLE 3

The procedure is carried out as in Example 1, but starting with 1.6 g of bromine in 10 ml of acetic acid, 2.3 g of potassium thiocyanate and 2.1 g of (R,S)-2-methyl-6-trifluoromethyl-1,2,3,4-tetrahydroquinoline in 25 ml of acetic acid. The residue obtained is chromatographed on a silica gel column, eluting with a mixture of cyclohexane and ethyl acetate (50-50 by volume) and gives an oil which is dissolved in ethanol and to which a solution of hydrochloric isopropanol (about 5 N) is added in a slight excess. The solution is concentrated under reduced pressure and the hydrochloride crystals obtained are recrystallized from ethanol containing traces of ethyl acetate. 0.9 g of (R,S)-2-imino-4-methyl-8-trifluoromethyl-5,6-dihydro-2H,4H-thiazolo[5,4,3-ij]quinoline hydrochloride is thus obtained which melts at around 180° C. with decomposition [$^1$H NMR spectrum in DMSO-d$_6$, T=300K, δ in ppm (300 MHz) 1.35 (3H, d, J=6 Hz, CH$_3$), 2.20 (2H, m, CH$_2$), 3.05 (2H, m, CH$_2$-aryl), 4.95 (1H, m, NCH), 7.80 (1H, s, arom. CH), 8.30 (1H, s, arom. CH), 10.90 (2H, broad s, NH.HCl)].

(R,S)-2-Methyl-6-trifluoromethyl-1,2,3,4-tetrahydroquinoline may be prepared by carrying out the procedure as in Example 1, but starting with 2.1 g of 2-methyl-6-trifluoromethylquinoline and 0.2 g of platinum oxide in 15 ml of tetrahydrofuran. The hydrogenation is carried out at a pressure of 10 to 5 bar for 30 minutes. 2.1 g of (R,S)-2-methyl-6-trifluoromethyl-1,2,3,4-tetrahydroquinoline are obtained in the form of a light-coloured oil [$^1$H NMR spectrum in DMSO-d$_6$, T=300K, δ in ppm (300 MHz): 1.20 (3H, d, J=6 Hz), CH$_3$), 1.35 and 1.90 (1H each, m, CH$_2$), 2.75 (2H, m, CH$_2$-aryl), 3.35 (1H, m, NCH), 6.35 (1H, s, NH), 6.55 (1H, d, J=8 Hz, arom. CH), 7.15 (2H, m, 2 arom. CH)].

2-Methyl-6-trifluoromethylquinoline may be prepared as described in J. Pharm. Sci., 68 (3), 336–8 (1979).

EXAMPLE 4

The procedure is carried out as in Example 1, but starting with 0.67 g of bromine in 2 ml of acetic acid, 0.94 g of potassium thiocyanate and 0.9 g of the laevorotatory isomer of (R,S)-2-methyl-6-trifluoromethyl-1,2,3,4-tetrahydroquinoline in 10 ml of acetic acid. 0.8 g of the dextrorotatory isomer of (R,S)-2-imino-4-methyl-8-trifluoromethyl-5,6-dihydro-2H,4H-thiazolo[5,4,3-ij]quinoline hydrochloride is thus obtained which decomposes above 200° C.; $[α]_D^{20}$=+39.0±0.7° (c=0.5; ethanol); [Analysis C$_{12}$H$_{12}$ClF$_3$N$_2$S, % calculated C: 46.68,H: 3.92, Cl: 11.48, F: 18.46, N: 9.07, S: 10.39,% found C: 46.3,H: 4.3, Cl: 11.4, F: 18.1, N: 9.1, S: 10.2].

The laevorotatory isomer of (R,S)-2-methyl-6-trifluoromethyl-1,2,3,4-tetrahydroquinoline may be prepared in the following manner: 11 g of (R,S)-2-methyl-6-trifluoromethyl-1,2,3,4-tetrahydroquinoline are treated with 17.5 g of 2,3-di-O-benzoyl-L-tartaric acid in a minimum amount of ethyl acetate at around 50° C., and then the solution left at a temperature close to 20° C. yields a solid. The latter is recrystallized once from ethyl acetate and then twice from 60% aqueous methanol to give 2.9 g of white crystals melting around 142° C.; $[α]_D^{20}$=−104.1±1.5° (c=0.5; ethanol). The salt thus obtained is triturated in 30 ml of 1 N sodium hydroxide solution and the base released is extracted with twice 50 ml of ethyl ether. The organic phase is washed with 10 ml of distilled water, and then dried over magnesium sulphate and concentrated under reduced pressure to yield 0.9 g of the laevorotatory isomer of (R,S)-2-methyl-6-trifluoromethyl-1,2,3,4-tetrahydroquinoline in the form of a light-coloured oil; $[α]_D^{20}$=−62.2±1.0° (c=0.5; ethanol).

EXAMPLE 5

The procedure is carried out as in Example 1, but starting with 0.81 g of bromine in 2 ml of acetic acid, 1.14 g of potassium thiocyanate and 1.1 g of the dextrorotatory isomer of 2-methyl-6-trifluoromethyl-1,2,3,4-tetrahydroquinoline in 10 ml of acetic acid. 1.0 g of the laevorotatory isomer of (R,S)-2-imino-4-methyl-8-trifluoromethyl-5,6-dihydro-2H,4H-thiazolo[5,4,3-ij]quinoline hydrochloride is thus obtained which decomposes above 200° C.; $[α]_D^{20}$=−39.4±0.7° (c=0.5; ethanol) [Analysis C$_{12}$H$_{12}$ClF$_3$N$_2$S, % calculated C: 46.68,H: 3.92, Cl: 11.48, F: 18.46, N: 9.07, S: 10.39, % found C: 46.5,H: 3.9, Cl: 11.7, F: 18.2, N: 9.0, S: 10.5].

The dextrorotatory isomer of (R,S)-2-methyl-6-trifluoromethyl-1,2,3,4-tetrahydroquinoline may be prepared in the following manner: the crystallization filtrates of the 2,3-di-O-benzoyl-L-tartrate of the laevorotatory isomer of (R,S)-2-methyl-6-trifluoromethyl-1,2,3,4-tetrahydroquinoline of Example 4 are concentrated under reduced pressure. By treating the evaporation residue obtained with a dilute sodium hydroxide solution and extracting with ethyl ether, 5.7 g of base are obtained in the form of an oil. They are treated with 10.5 g of 2,3-di-O-benzoyl-D-tartaric acid in the minimum amount of ethyl acetate at around 50° C., and then the solution left at a temperature close to 20° C. yields a solid. The latter is recrystallized once from ethyl acetate and then twice from 600 aqueous methanol to give 3.3 g of white crystals melting at around 145° C.; $[\alpha]_D^{20}$=+94.6±1.4° (c=0.5; ethanol). The salt thus obtained is triturated in 30 ml of 1 N sodium hydroxide solution and the base released is extracted with twice 50 ml of ethyl ether. The organic phase is washed with 10 ml of distilled water, and then dried over magnesium sulphate and concentrated under reduced pressure to give 1.1 g of the dextrorotatory isomer of (R,S)-2-methyl-6-trifluoromethyl-1,2,3,4-tetrahydroquinoline in the form of a light-coloured oil; $[\alpha]_D^{20}$=+62.9±1.2° (c=0.5; ethanol).

EXAMPLE 6

1.2 g of bromine diluted in 5 ml of acetic acid are added dropwise over 10 minutes, at a temperature close to 20° C., to a solution of 1.7 g of potassium thiocyanate and 2.2 g of (R,S)-2-methylsulphonylmethyl-6-trifluoromethoxy-1,2,3, 4-tetrahydroquinoline in 20 ml of acetic acid. The reaction mixture is stirred for 20 hours at the same temperature, poured over ice, alkalinized with a solution of aqueous ammonia at 20% and extracted with twice 150 ml of ethyl acetate. The organic phases are combined, washed with 100 ml of distilled water, dried over magnesium sulphate and concentrated to dryness under reduced pressure (2 kPa) at 40° C. The solid obtained is purified by trituration in ethyl ether and then recrystallized from ethyl acetate. 1.2 g of (R,S)-2-imino-4-methylsulphonylmethyl-8-trifluoromethoxy-5,6-dihydro-2H,4H-thiazolo[5,4,3-ij] quinoline are thus obtained in the form of yellow crystals melting at 195° C. [$^1$H NMR spectrum in DMSO-$d_6$, T=300K, % in ppm (300 MHz): 1.95 and 2.50 (1H each, m, CH$_2$), 2.80 and 3.00 (H each, m, CH$_2$-aryl), 3.15 (3H, , CH$_3$), 3.50 (2H, m, SCH$_2$), 4.90 (H, m, NH), 7.10 (1H, s, arom. CH), 7.45 (1H, s, arom. CH), 8.60 (1H, s, NH)].

(R,S)-2-Methylsulphonylmethyl-6-trifluoromethoxy-1,2, 3,4-tetrahydroquinoline may be prepared by carrying out the procedure as in Example 1, but starting with 2.3 g of 2-methylsulphonylmethyl-6-trifluoromethoxyquinoline, 0.4 g of platinum oxide in 25 ml of a methanol-tetrahydrofuran mixture (50-50 by volume). 2.2 g of (R,S)-2-methylsulphonylmethyl-6-trifluoromethoxy-1,2,3,4-tetrahydroquinoline are thus obtained in the form of a white solid melting at 103° C.

2-Methylsulphonylmethyl-6-trifluoromethoxyquinoline may be prepared in the following manner: the solution of 2.7 g of 1-(methylsulphonyl)propan-2-one in 10 ml of dimethyl ether of ethylene glycol is added to a solution of 4.6 g of 6-trifluoromethoxyquinoline 1-oxide in 3.8 ml of acetic anhydride, stirred at a temperature close to 20° C. for 20 hours, and then at around 60° C. for 20 hours. The reaction medium is then supplemented with 5 ml of methanol and heated under reflux for 1 hour. It is then poured over ice and then alkalinized with a concentrated sodium hydroxide solution. The brown precipitate which appears is extracted with twice 150 ml of ethyl acetate. The organic phase is dried over magnesium sulphate and concentrated under reduced pressure (2 kPa) at 40° C., yielding a brown oil which rapidly crystallizes. The crystals are triturated in 10 ml of ethanol and 2.3 g of 2-methylsulphonylmethyl-6-trifluoromethoxyquinoline are thus obtained in the form of a white solid melting at 143° C.

6-Trifluoromethoxyquinoline 1-oxide may be prepared in the following manner: 3-chloroperbenzoic acid is added in two portions (7.2 g at the beginning and 3 g after 20 hours) to a solution of 8.9 g of 6-trifluoromethoxyquinoline in 200 ml of dichloromethane, kept at a temperature close to 20° C. The reaction medium is stirred for a further 4 hours after the second addition and then concentrated under reduced pressure (2 kPa) at 20° C. The residue obtained is purified by chromatography on a silica gel column, eluting with ethyl acetate and then with a mixture of ethyl acetate and methanol (80-20 by volume). 8.8 g of 6-trifluoromethoxyquinoline 1-oxide are thus obtained in the form of a light-brown oil which crystallizes into a solid melting at 72° C.

EXAMPLE 7

The procedure is carried out as in Example 1, but starting with 0.37 g of bromine diluted in 2 ml of acetic acid, 0.52 g of potassium thiocyanate and 0.6 g of (R,S)-6-trifluoromethoxy-1,2,3,4-tetrahydroquinoline-2-methanol in 7 ml of acetic acid. After recrystallization from ethanol containing traces of petroleum ether, 0.27 g of (R,S)-2-imino-8-trifluoromethoxy-5,6-dihydro-2H,4H-thiazolo[5,4, 3-ij]quinoline- 4-methanol hydrochloride is obtained, melting at 132° C. with decomposition [$^1$H NMR spectrum in DMSO-$d_6$, T=300K, δ in ppm (300 MHz): 2.00 and 2.35 (1H each, m, CH$_2$), 2.90 and 3.05 (1H each, m, CH$_2$-aryl), 3.65 and 3.75 (1H each, m, OCH$_2$), 4.78 (1H, m, NCH), 5.30 (1H, broad s, OH), 7.40 (1H, s, arom. CH), 7.95 (1H, s, arom. CH)].

(R,S)-6-Trifluoromethoxy-1,2,3,4-tetrahydroquinoline-2-methanol may be prepared as in Example 1, but starting with 1.5 g of 2-hydroxymethyl-6-trifluoromethoxyquinoline and 0.3 g of platinum oxide in 15 ml of methanol. 1.4 g of (R,S)-G-trifluoromethoxy-1,2,3,4-tetrahydroquinoline-2-methanol are obtained in the form of a light-coloured oil which crystallizes into a solid melting at 77° C.

6-Trifluoromethoxyquinoline-2-methanol may be prepared in the following manner: a solution of 9.2 g of 2-methyl-6-trifluoromethoxyquinoline 1-oxide in 35 ml of acetic anhydride is heated at boiling temperature for 3 hours and then concentrated under reduced pressure. The oil obtained is dissolved in 50 ml of dioxane and then 30 ml of distilled water and a concentrated sodium hydroxide solution (3 ml in addition to the quantity necessary for the neutralization) are added. The reaction medium is heated for 1 hour under reflux and then concentrated to dryness. The residue obtained is extracted with 400 ml of ethyl acetate, the organic phase is washed with 50 ml of distilled water and then dried over magnesium sulphate and concentrated under reduced pressure (2 kPa) at 40° C. The residue obtained is chromatographed on a silica gel column, eluting with a mixture of cyclohexane and ethyl acetate (50-50 by volume). 5.7 g of 6-trifluoromethoxyquinoline-2-methanol are thus obtained in the form of a whitish solid melting at 75° C.

2-Methyl-6-trifluoromethoxyquinoline 1-oxide may be prepared in the following manner: 3-chloroperbenzoic acid is added in two portions (2.8 g at the beginning and 0.3 g after 1 hour) to the solution, kept at a temperature close to 20° C., of 2.8 g of 2-methyl-6-trifluoromethoxyquinoline in 50 ml of dichloromethane. The reaction medium is stirred for a further 19 hours after the second addition and is then washed with a dilute solution of sodium hydrogen carbonate. The organic phase is then dried over magnesium sulphate and concentrated under reduced pressure (2 kPa) at 20° C. After trituration of the residue obtained in petroleum ether, 2.5 g of 2-methyl-6-trifluoromethoxyquinoline 1-oxide are obtained in the form of whitish crystals melting at 105° C.

2-Methyl-6-trifluoromethoxyquinoline may be prepared in the following manner: a suspension of 70.8 g of 4-trifluoromethoxyaniline, 100 ml of concentrated hydrochloric acid, 99 g of 2,3,5,6-tetrachloro-1,4-benzoquinone in 100 ml of n-butanol is heated to reflux temperature and a solution of 34 g of crotonaldehyde in 40 ml of n-butanol is added dropwise over 3 hours, and then the boiling is continued for 20 minutes and the temperature is allowed to return to close to 20° C. The neutral products are extracted with four times 400 ml of ethyl ether and removed, and then the aqueous phase is alkalinized with 120 ml of concentrated sodium hydroxide solution. The oil which appears is extracted with three times 500 ml of ethyl ether, the organic phase is then washed with 100 ml of distilled water and then dried over magnesium sulphate and concentrated under reduced pressure (2 kPa) at 40° C. The residue obtained is chromatographed on a silica gel column, eluting with a mixture of cyclohexane and ethyl acetate (50-50 by volume), and is then distilled at 100° C. at 0.7 kPa to give 52.5 g of 2-methyl-6-trifluoromethoxyquinoline in the form of a greenish yellow solid melting at around 43° C. [$^1$H NMR spectrum in DMSO-$d_6$, T=300K, δ in ppm (250 MHz): 2.70 (3H, s, $CH_3$), 7.55 (1H, d, J=8 Hz, CH at position 3) 7.72 (1H, dd, J=8 and 2 Hz, CH at position 7), 8.01 (1H, s, CH at position 5), 8.08 (1H, d, J=8 Hz, CH at position 8), 8.40 (1H, d, J=8 Hz, CH at position 4)].

EXAMPLE 8

The procedure is carried out as in Example 1, but starting with 2.2 g of bromine in 10 ml of acetic acid, 3.09 g of potassium thiocyanate and 3.2 g of 6-trifluoromethoxy-2,3-dihydro-(1H)-quinolin-4-one in 35 ml of acetic acid. The organic phase is extracted with 170 ml of an approximately 0.1 N aqueous hydrochloric acid solution. The aqueous hydrochloric phase is alkalinized with 4 ml of a 10 N sodium hydroxide solution and extracted with three times 100 ml of ethyl acetate. The organic extracts are combined, washed with 100 ml of distilled water, dried over magnesium sulphate and concentrated to dryness under reduced pressure (2 kPa) at 40° C. The crude product obtained is chromatographed on silica gel, eluting with a mixture of ethyl acetate and petroleum ether (80-20 by volume). The yellow solid isolated (0.3 g) is washed with a cold solution of petroleum ether and of isopropyl ether (60-40 by volume), and is then dried under reduced pressure (70 Pa) at 40° C. 0.25 g of 2-imino-8-trifluoromethoxy-2H,4H-thiazolo[5,4,3-ij] quinolin-6-one is thus obtained in the form of a yellow powder melting at 192° C. [Analysis $C_{11}H_7F_3N_2O_2S$, % calculated C: 45.84,H: 2.45, F: 19.77, N: 9.72, O: 11.1, S: 11.12, % found C: 45.5,H: 2.1, F: 19.4, N: 9.3, S: 11.1].

6-Trifluoromethoxy-2,3-dihydro-(1H)-quinolin-4-one may be prepared in the following manner: 10 ml of trifluoroacetic acid are added to a solution of 3.4 g of tert-butyl 4-oxo-6-trifluoromethoxy-3,4-dihydro-(2H)-quinoline-1-carboxylate in 60 ml of dichloromethane. After 3 hours at a temperature close to 20° C., the reaction medium is concentrated to dryness under reduced pressure. The residue is treated with a dilute sodium hydrogen carbonate solution and extracted with ethyl ether. The organic phase is washed with distilled water, dried over magnesium sulphate and concentrated to dryness under reduced pressure (2,2 kPa) at 50° C. 2.1 g of an ochre-coloured solid are obtained, which solid is chromatographed on silica gel, eluting with a mixture of dichloromethane and petroleum ether (70-30 by volume). 1.75 g of 6-trifluoromethoxy-2,3-dihydro-(1H)-quinolin-4-one are thus obtained in the form of a bright yellow solid melting at 118° C.

tert-Butyl 4-oxo-6-trifluoromethoxy-3,4-dihydro-(2H)-quinoline-1-carboxylate may be prepared in the following manner: 18.5 ml of a 70% aqueous solution of tert-butyl hydroperoxide and 0.095 g of chromic anhydride are first added to a stirred solution of 11.6 g of tert-butyl 6-trifluoromethoxy-3,4-dihydro-(2H)-quinoline-1-carboxylate in 120 ml of dichloromethane. After 4 hours at a temperature close to 20° C., 18.5 ml of a 70% aqueous solution of tert-butyl hydroperoxide and 0.095 g of chromic anhydride are again added. To complete the reaction, 10 ml of a 70% aqueous solution of tert-butyl hydroperoxide and 60 mg of chromic anhydride are added after 18 hours and then the reaction mixture is left for 24 hours. A solution of sodium dithionite is then added, at cold temperature, until the evolution of gas ceases. The organic phase is washed with distilled water and with a saturated aqueous solution of sodium chloride, dried over magnesium sulphate and then concentrated to dryness under reduced pressure (2 kPa) at 40° C. The red oil obtained is filtered on silica gel, eluting with petroleum ether. 8.45 g of tert-butyl 4-oxo-6-trifluoromethoxy-3,4-dihydro-(2H)-quinoline-1-carboxylate are thus obtained in the form of a yellow powder melting at 66° C.

tert-Butyl 6-trifluoromethoxy-3,4-dihydro-2H-quinoline-1-carboxylate may be prepared in the following manner: a solution of 11 g of 6-trifluoromethoxy-1,2,3,4-tetrahydroquinoline and 11.8 g of di-tert-butyl dicarbonate in 110 ml of tetrahydrofuran is heated to and kept at boiling temperature for 16 hours. To complete the reaction, 1.9 g of di-tert-butyl dicarbonate are added and the boiling is continued for 4 hours and then the mixture is concentrated under reduced pressure. The residue obtained is extracted with 300 ml of ethyl ether, the organic phase is washed with 50 ml of distilled water, dried over magnesium sulphate and concentrated under reduced pressure (2 kPa) at 20° C. After trituration of the residue in petroleum ether, 9.2 g of tert-butyl 6-trifluoromethoxy-3,4-dihydro-2H-quinoline-1-carboxylate are obtained in the form of white crystals melting at 68° C.

EXAMPLE 9

3.35 g of 2-imino-8-trifluoromethoxy-4,5-dihydro-2H-thiazolo[3,4,5-de] [1,4]benzothiazine are added to a solution, under argon and cooled to 5° C., of 5.3 g of 3-chloroperbenzoic acid (80% purity) in 100 ml of dichloromethane and the stirring is maintained for 16 hours at a temperature close to 20° C. 100 ml of a 1 M aqueous solution of sodium hydrogen carbonate are then added and the mixture is stirred for 1 hour at the same temperature. After separation of the two phases, the aqueous phase is extracted twice with 50 ml of dichloromethane and the combined organic extracts are dried over magnesium sulphate and concentrated to dryness under reduced pressure (2 kPa). The yellow oil obtained is chromatographed under nitrogen pressure (150 kPa) on 20 g of 20–45 μm silica gel contained in a column 2 cm in diameter, eluting with ethyl acetate. The product obtained (730 mg) is dissolved in 50 ml of absolute ethanol, and then 100 µl of methanesulphonic acid are added. After stirring for 1 hour 45 minutes, the precipitate is separated by filtration, washed with ethanol and then with ethyl ether and dried under reduced pressure (2 kPa) at 20° C. 750 mg of 2-imino-8-trifluoromethoxy-4,5-dihydro-2H-thiazolo[3,4,5-de]-[1,4]benzothiazine 6,6-dioxide methanesulphonate are thus obtained in the form of a white solid melting at a temperature greater than 260° C. [Analysis $C_{11}H_{11}F_3N_2O_6S_3$, % calculated C: 31.43,H: 2.64, F: 13.56, N: 6.66, S: 22.88,% found C: 31.39H: 2.29, F: 13.28, N: 6.59, S: 22.60].

EXAMPLE 10

5 g of 2-imino-8-trifluoromethoxy-4,5-dihydro-2H-thiazolo[3,4,5-de] [1,4]benzothiazine are added to a solution, under argon and cooled to −10° C., of 4.5 g of 3-chloroperbenzoic acid (80% purity) in 150 ml of dichloromethane and the mixture is stirred for 1 hour at a temperature close to 20° C. The mixture is filtered and concentrated to dryness under reduced pressure (2 kPa). The yellow solid obtained is chromatographed under nitrogen pressure (150 kPa) on 60 g of 20–45 µm silica gel contained in a column 2.5 cm in diameter, eluting with a mixture of ethyl acetate and methanol (80-20 by volume). The product obtained (3.3 g) is dissolved in 200 ml of absolute ethanol and then 0.8 ml of methanesulphonic acid is added. After stirring for 5 hours at 20° C., the solution is concentrated to dryness under reduced pressure (2 kPa). The product obtained is suspended in ethyl ether, separated by filtration, washed with ethyl ether and dried under reduced pressure (2 kPa) at 20° C. 3.9 g of (R,S)-2-imino-8-trifluoromethoxy-4,5-dihydro-2H-thiazolo[3,4,5-de] [1,4]benzothiazine 6-oxide methanesulphonate are thus obtained in the form of a pale yellow solid melting at 268° C. [Analysis $C_{11}H_{11}F_3N_2O_5S_3$, % calculated C: 32.67,H: 2.74, F: 14.09, N: 6.93, O: 19.78, S: 23.79,% found C: 32.87H: 2.39, F: 14.46, N: 6.91, S: 23.49].

EXAMPLE 11

The procedure is carried out as in Example 1, but using 0.33 ml of bromine diluted in 5 ml of acetic acid, 1.5 g of 7-trifluoromethoxy-3,4-dihydro-2H-[1,4]benzothiazine and 1.3 g of potassium thiocyanate in 20 ml of acetic acid. 1 g of 2-imino-8-trifluoromethoxy-4,5-dihydro-2H-thiazolo[3,4,5-de] [1,4]benzothiazine hydrochloride is thus obtained in the form of a yellow powder melting at 245SC [Analysis $C_{10}H_8ClF_3N_2OS_2$, % calculated C: 36.53,H: 2.45, Cl: 10.78, F: 17.34, N: 8.52, O: 4.87, S: 19.51, % found C: 36.59 H: 2.18, Cl: 10.48, F: 16.94, N: 8.63, S: 19.15].

7-Trifluoromethoxy-3,4-dihydro-2H-[1,4]benzothiazine may be prepared in the following manner: a solution of 2 g of 7-trifluoromethoxy-1H-[1,4]-benzothiazin-3-one in 15 ml of anhydrous tetrahydrofuran is added dropwise over 15 minutes to 19 ml of an approximately 0.5 M solution of lithium tetrahydroaluminate in tetrahydrofuran, kept under argon at 5° C. The reaction mixture is then stirred for 2 hours at 20° C. The insoluble matter is separated by filtrations and washed with tetrahydrofuran. The filtrate diluted with ethyl acetate is washed with distilled water, dried over magnesium sulphate and concentrated to dryness under reduced pressure (2 kPa). 1.7 g of 7-trifluoromethoxy-3,4-dihydro-2H-[1,4] benzothiazine are thus obtained in the form of an amber-coloured oil [$^1$H NMR spectrum (CDCl$_3$), T=300K, δ in ppm (300 MHz) 3.05 (2H, m, SCH$_2$), 3.65 (2H, m, NCH$_2$), 4.05 (1H, broad s, NH), 6.40 (1H, d, J=8 Hz, arom. CH), 6.75 (1H, d, J=8 Hz, arom. CH), 6.90 (1H, s, arom. CH)].

7-Trifluoromethoxy-1H-[1,4]benzothiazin-3-one may be prepared in the following manner: 140 g of potassium hydroxide pellets are added in portions of about 10 g to a suspension of 23 g of 2-amino-6-trifluoromethoxybenzothiazole in 230 ml of distilled water. The mixture is then stirred for 16 hours at a temperature close to 20° C., and then for 5 hours under reflux. After cooling to around 20° C., 30 g of methyl bromoacetate are added and then 30 ml of distilled water and the medium is stirred for 16 hours at the same temperature, and then filtered. The filtrate is then acidified with concentrated hydrochloric acid at a temperature close to 5° C. The precipitate which appears is separated by filtration, washed with distilled water and dried under an airstream at around 20° C. 20 g of 7-trifluoromethoxy-1H-[1,4]benzothiazin-3-one are thus obtained in the form of a whitish solid melting at 185° C.

2-Amino-6-trifluoromethoxybenzothiazole may be prepared by the method described by L. M. YAGUPOL'SKII et al., Zh. Obshch. Khim., 33 (7), 2301 (1963).

EXAMPLE 12

A total of 475 mg of 3-chloroperbenzoic acid (80% purity) are added in three portions over a period of 5 hours to a solution, kept at −10° C., of 500 mg of 2-imino-8-trifluoromethyl-4,5-dihydro-2H-thiazolo[3,4,5-de] [1,4] benzothiazine in 15 ml of dichloromethane. The mixture is then stirred for 1 hour at a temperature close to 20° C. and concentrated to dryness under reduced pressure (2 kPa). The product obtained is chromatographed under nitrogen pressure (150 kPa) on 25 g of 20–45 µm silica gel contained in a column 2 cm in diameter, eluting first with ethyl acetate and then with a mixture of ethyl acetate and methanol (80-20 by volume). The product obtained (350 mg) is dissolved in 5 ml of absolute ethanol to which there are added 95 µl of methanesulphonic acid. After stirring for 16 hours at 20° C., the precipitate which appears is recrystallized from ethanol. 366 mg of (R,S)-2-imino-8-trifluoromethyl-4,5-dihydro-2H-thiazolo-[3,4,5-de] [1,4]benzothiazine 6-oxide methanesulphonate are thus obtained in the form of an off-white solid melting at 236° C. [Analysis $C_{11}H_{11}F_3N_2O_4S_3$. % calculated C: 34.02,H: 2.85, F: 14.67, N: 7.21, O: 16.48, S: 24.77, % found C: 33.7,H: 2.7, F: 14.3, N: 7.00, S: 24.9].

EXAMPLE 13

The procedure is carried out as in Example 1, but starting with 2.2 g of bromine in 10 ml of acetic acid, 3 g of 7-trifluoromethyl-3,4-dihydro-2H-[1,4]benzo-thiazine and 2.9 g of potassium thiocyanate in 30 ml of acetic acid. The product obtained (3.74 g) is chromatographed under nitrogen pressure (150 kPa) on 50 g of 20–45 µm silica gel contained in a column 3 cm in diameter, eluting with a mixture of ethyl acetate and cyclohexane (50-50 by volume). The product obtained is suspended in petroleum ether, separated by filtration, washed with petroleum ether and dried under reduced pressure. 0.3 g of the product obtained (out of 1.8 g obtained in total) is dissolved in 5 ml of ethanol, to which 0.07 ml of methanesulphonic acid is added. After stirring for 1 hour at 20° C., the product is recrystallized from absolute ethanol. 0.29 g of 2-imino-8-trifluoromethyl-4,5-dihydro-2H-thiazolo[3,4,5-de] [1,4] benzothiazine methanesulphonate is thus obtained in the form of a white solid melting at 262° C. [Analysis $C_{11}H_{11}F_3N_2O_3S_3$, % calculated C: 35.48,H: 2.98, F: 15.30, N: 7.52, O: 12.89, S: 25.83,% found C: 35.4 H: 2.9, F: 15.1, N: 7.5, S: 26.1].

7-Trifluoromethyl-3,4-dihydro-2H-[1,4]benzothiazine may be prepared in the following manner: the procedure is carried out as in Example 14, but using 16 ml of a solution of lithium tetrahydroaluminate (about 0.3 M) in tetrahydrofuran, 930 mg of 7-trifluoromethyl-1H-[1,4] benzothiazin-3-one in 10 ml of anhydrous tetrahydrofuran. The reaction mixture is then stirred for 16 hours at 20° C., supplemented slowly with 2 ml of distilled water, and stirred for 1 hour at a temperature close to 20° C. The insoluble matter is separated by filtration, washed with ethyl acetate and removed. The filtrate and the washing are combined, washed with distilled water, dried over magnesium sulphate and concentrated to dryness under reduced pressure (2 kPa). 410 mg of 7-trifluoromethyl-3,4-dihydro-2H-[1,4] benzothiazine are thus obtained in the form of a yellow oil [$^1$H NMR spectrum in DMSO-$d_6$, T=300K, δ in ppm (300 MHz): 3.00 (2H, m, SCH$_2$), 3.60 (2H, m, NCH$_2$), 6.65 (1H, d, J=8 Hz, arom. CH), 6.85 (1H, s, NH), 7.05 (1H, d, J=8 Hz, arom. CH), 7.08 (1H, s, arom. CH)].

7-Trifluoromethyl-1H-[1,4]benzothiazin-3-one may be prepared in the following manner: a mixture of 7.9 g of methyl (5-trifluoromethyl-2-tert-butoxycarbonylaminophenylsulphanyl)acetate and 12 ml of trifluoroacetic acid in 15 ml of dichloromethane is stirred for 2 hours at a temperature close to 20° C. The mixture is then concentrated to dryness under reduced pressure (2 kPa). The product obtained is suspended in isopropyl ether, filtered, rinsed with the same solvent, drained, and dried under reduced pressure (2 kPa) at 20° C. 3.5 g of 7-trifluoromethyl-1H-[1,4]-benzothiazin-3-one are thus obtained in the form of a light-beige solid melting at 168° C.

Methyl (5-trifluoromethyl-2-tert-butoxycarbonylaminophenyl)sulphanyl acetate may be prepared in the following manner: 102 ml of a solution (about 1.5 M) of tert-butyllithium in pentane are added dropwise, over 30 minutes, to a solution of 20 g of tert-butyl 4-trifluoromethylphenylcarbamate in 300 ml of anhydrous tetrahydrofuran, kept under an argon atmosphere at a temperature of less than −20° C. The mixture is stirred for 3 hours 15 minutes at the same temperature, and then 2.5 g of sulphur are added at −30° C. The mixture is stirred for 1.5 hours, while allowing the temperature to rise gradually to 20° C., supplemented with 10.8 g of methyl bromoacetate, and stirred for 16 hours at a temperature close to 20° C. After addition of distilled water, the mixture is extracted twice with ethyl acetate. The organic extracts are combined, dried over magnesium sulphate and concentrated to dryness under reduced pressure (2 kPa). The product obtained (29.5 g) is chromatographed under nitrogen pressure (150 kPa) on 400 g of 20–45 μm silica gel contained in a column 6 cm in diameter, eluting with a mixture of cyclohexane and ethyl acetate (90-10 by volume). 6.2 g of methyl (5-trifluoromethyl-2-tert-butoxycarbonylaminophenyl) sulphanyl acetate are thus obtained in the form of an amber-coloured oil [$^1$H NMR spectrum in DMSO-$d_6$, T=300K, δ in ppm (200 MHz): 1.50 (9H, s, C(CH$_3$)$_3$), 3.60 (3H, s, OCH$_3$), 3.90 (2H, s, SCH$_2$CO), 7.65 (1H, dd, J=2 and 8 Hz, arom. CH), 7.84 (1H, d, J=2 Hz, arom. CH), 7.87 (1H, d, J=8 Hz, arom. CH), 8.70 (1H, s, NH)].

tert-Butyl 4-trifluoromethylphenylcarbamate may be prepared in the following manner: a solution of 163 g of di-tert-butyldicarbonate in 100 ml of anhydrous tetrahydrofuran are poured, over 10 minutes at 0° C., over a solution of 96 g of 4-trifluoromethylaniline in 750 ml of anhydrous tetrahydrofuran. The reaction medium is stirred at 80° C. for 3 hours, and then concentrated to dryness. A product is obtained which is redissolved in 300 ml of ethyl acetate. The solution is washed three times with distilled water, dried over magnesium sulphate and concentrated to dryness. 136 g of tert-butyl 4-trifluoromethylphenylcarbamate are thus obtained in the form of a white solid melting at 121° C.

EXAMPLE 14

A solution of 0.96 g of bromine in 10 ml of acetic acid is added dropwise, over 10 minutes at a temperature of less than 30° C., to a solution of 1.7 g of (R,S)-4-phenyl-6-trifluoromethyl-1,2,3,4-tetrahydroquinoline and 1.3 g of potassium thiocyanate in 40 ml of acetic acid. The mixture is stirred for 2 hours at a temperature close to 20° C., poured over 16 g of ice, supplemented with 18 ml of aqueous ammonia at about 28% and 25 ml of ethyl acetate and then filtered. After decantation, the aqueous phase is extracted twice with a total of 50 ml of ethyl acetate and the organic extracts are combined, dried over magnesium sulphate and concentrated to dryness under reduced pressure (2.2 kPa) at 60° C. The product obtained (4.3 g) is chromatographed under nitrogen pressure (150 kPa) on 835 g of 20–45 μm neutral silica gel contained in a column 6.8 cm in diameter, eluting with a mixture of dichloromethane and methanol (98-2 by volume). The product obtained (1.1 g) is dissolved in 3 ml of ethanol and, after addition of 5 ml of 3.8 N hydrochloric ether and storing for 1 hour at a temperature close to 5° C., the insoluble matter is separated by filtration, washed twice with a total of 20 ml of ethyl ether and dried under reduced pressure (0.13 kPa) at 60° C. 0.8 g of (R,S)-2-imino-6-phenyl-8-trifluoromethyl-5,6-dihydro-2H, 4H-thiazolo[5,4,3-ij]-quinoline hydrochloride is thus obtained in the form of a yellow solid melting above 260° C. with decomposition [$^1$H NMR spectrum in DMSO-$d_6$, T=300K, δ in ppm (300 MHz) 22.40 (2H, m, CH$_2$), 4.05 and 4.20 (1H each, m, NCH$_2$) 4.45 (1H, t, J=6 Hz, NCH), 7.20 (3H, m, 3 arom. CH), 7.40 (3H, m, 3 arom. CH), 8.30 (1H, s, arom. CH), 10.50 (2H, broad s, NH.HCl)].

(R,S)-4-Phenyl-6-trifluoromethyl-1,2,3,4-tetrahydroquinoline may be prepared in the following manner: 4.7 g of tin tetrachloride are added dropwise over 5 minutes at −78° C. to a suspension of 6.6 g of N-para-toluenesulphonylmethyl-4-trifluoromethylaniline in 100 ml of dichloromethane. The mixture is stirred for 10 minutes and a solution of 2.1 g of styrene in 50 ml of dichloromethane is added dropwise over 30 minutes at the same temperature. The mixture is stirred for 1 hour at −78° C. and for 15 hours at a temperature close to 20° C. and then it is neutralized with 100 ml of a saturated aqueous sodium hydrogen carbonate solution. After addition of 50 ml of distilled water and 250 ml of dichloromethane, the aqueous phase is extracted twice with a total of 100 ml of dichloromethane. The organic extracts are combined, washed twice with 100 ml of distilled water, dried over magnesium sulphate and concentrated to dryness under reduced pressure (2.2 kPa) at 60° C. The product obtained (5.6 g) is chromatographed under nitrogen pressure (150 kPa) on 1390 g of 20–45 μm neutral silica gel contained in a column 6.8 cm in diameter, eluting with a mixture of cyclohexane and ethyl acetate (85-15 by volume). 3.3 g of (R,S)-4-phenyl-6-trifluoromethyl-1,2,3,4-tetrahydroquinoline are thus obtained in the form of a yellow oil [$^1$H NMR spectrum in DMSO-$d_6$, T=300K, δ in ppm (300 MHz): -2.00 (2H, m, H$_2$), 3.05 and 3.25 (1H each, m, NCH$_2$) 4.15 (1H, t, J=6 Hz, CH-Ph), 6.65 (2H, m, arom. CH and NH), 6.85 (1H, s, arom. CH), 7.10 (2H, d, J=7 Hz, 2 arom. CH), 7.25 (2H, t, J=7 Hz, 2 arom. CH), 7.30 (2H, t, J=7 Hz, 2 arom. CH)].

N-Para-toluenesulphonylmethyl-4-trifluoromethylaniline may be prepared in the following manner: 26.75 g of a 37% aqueous solution of formaldehyde are added to a solution of 53.4 g of sodium para-toluenesulphinate in 600 ml of distilled water. The mixture is stirred and a solution of 48.3 g of trifluoromethylaniline in 900 ml of a 0.033 N aqueous hydrochloric acid solution is added dropwise over 20 minutes at a temperature of less than 30° C. The mixture is stirred for 15 hours at a temperature close to 20° C. and the insoluble matter which appears is separated by filtration, washed twice with a total of 500 ml of distilled water. The wet product obtained (161.2 g) is dissolved in 900 ml of boiling methanol and, after cooling and storing for one hour at a temperature close to 5° C., the crystals which appear are separated by filtration, washed twice with a total of 600 ml of methanol cooled to 5° C. and dried under reduced pressure (0.13 kPa) at 50° C. 75.9 g of N-para-toluenesulphonylmethyl-4-trifluoromethylaniline are thus obtained, melting at 135° C.

EXAMPLE 15

A solution of 0.62 g of bromine in 3 ml of acetic acid is added dropwise, over 10 minutes at a temperature of less than 30° C., to a solution of 1.06 g of (R,S)-4-(N-methylacetamido)-6-trifluoromethyl-1,2,3,4-tetrahydroquinoline and 0.83 g of potassium thiocyanate in 15 ml of acetic acid. The mixture is stirred for 16 hours at a temperature close to 20° C., poured over 20 g of ice and 20 ml of distilled water and extracted twice with a total of 60 ml of ethyl acetate. The organic extracts are removed and the aqueous phase is alkalinized with 20 ml of aqueous ammonia at 28% and then extracted 3 times with a total of 45 ml of ethyl acetate. The organic extracts are combined, dried over magnesium sulphate and concentrated to dryness under reduced pressure (2.2 kPa) at 60° C. The product obtained (0.44 g) is dissolved in 1 ml of ethanol and, after addition of 5 ml of 1.5 N hydrochloric ether, the mixture is stored for 1 hour at a temperature close to 5° C. The insoluble matter which appears is separated by filtration, washed twice with a total of 10 ml of ethyl ether and dried under reduced pressure (0.13 kPa) at 60° C. 0.4 g of (R,S)-N-(2-imino-8-trifluoromethyl-5,6-dihydro-2H,4H-thiazolo[5,4,3-ij]quinol-6-yl-N-methylacetamide hydrochloride is thus obtained in the form of a cream-coloured solid melting at 200° C. with decomposition.

(R,S)-4-(N-Methylacetamido)-6-trifluoromethyl-1,2,3,4-tetrahydroquinoline may be prepared in the following manner: 3.25 g of tin tetrachloride are added dropwise over 5 minutes at −78° C. to a suspension of 1.65 g of N-para-toluenesulphonylmethyl-4-trifluoromethylaniline in 25 ml of dichloromethane. The mixture is stirred for 10 minutes and a solution of 0.5 g of M-methyl-N-vinylacetamide in 15 ml of dichloromethane is added dropwise over 10 minutes at the same temperature. The mixture is stirred for 1 hour at −78° C. and for 15 hours at a temperature close to 20° C. The insoluble matter which appears is separated by filtration, washed twice with a total of 20 ml of dichloromethane, suspended in 20 ml of distilled water and the stirred mixture is neutralized with 60 ml of a saturated aqueous sodium hydrogen carbonate solution and extracted 3 times with a total of 70 ml of dichloromethane. The organic extracts are combined, washed twice with a total of 20 ml of distilled water, dried over magnesium sulphate and concentrated to dryness under reduced pressure (2.2 kPa) at 60° C. 1.06 g of (R,S)-4-(N-methylacetamido)-6-trifluoromethyl-1,2,3,4-tetrahydroquinoline are thus obtained in the form of a yellow lacquer [$^1$H NMR spectrum in DMSO-d$_6$, T=393K, δ in ppm (400 MHz): 2.00 (2H, m, CH$_2$); 2.15 (3H, s, COCH$_3$), 2.70 (3H, s, NCH$_3$), 3.40 (2H, m, NCH$_2$) 5.50 (1H, broad s, NCH), 6.70 (1H, d, J=8 Hz, arom. CH), 7.00 (1H, d, J=2 Hz, arom. CH), 7.25 (1H, dd, J=8 and 2 Hz, arom. CH)].

EXAMPLE 16

A solution of 0.86 g of bromine in 3.5 ml of acetic acid is added dropwise, over 10 minutes at a temperature of less than 30° C., to a solution of 1.25 g of (R,S)-6-trifluoromethyl-1,2,3,4-tetrahydroquinoline-4-methanol and 1.15 g of potassium thiocyanate in 20 ml of acetic acid. The mixture is stirred for 16 hours at a temperature close to 20° C., poured over 30 g of ice and 30 ml of distilled water and extracted with 40 ml of dichloromethane. The organic extract is removed and the aqueous phase is alkalinized with 30 ml of aqueous ammonia at 28% and then extracted 3 times with a total of 60 ml of dichloromethane. The organic extracts are combined, dried over magnesium sulphate and concentrated to dryness under reduced pressure (2.2 kPa) at 60° C. The product obtained (1.09 g) is dissolved in 10 ml of methanol and, after addition of 15 ml of 1.2 N hydrochloric ether, the mixture is stored for 1 hour at a temperature close to 5° C. The insoluble matter which appears is separated by filtration, washed twice with a total of 10 ml of ethyl ether and dried under reduced pressure (0.13 kPa) at 60° C. 0.56 g of the product obtained (out of the 0.9 g obtained in total) is suspended in 56 ml of distilled water at 50° C. and, after addition of decolorizing charcoal and filtration, the filtrate is concentrated to dryness under reduced pressure (0.13 kPa) at 60° C. The product obtained (0.46 g) is suspended in 5 ml of acetone, filtered, washed twice with a total of 6 ml of acetone and dried under reduced pressure (0.13 kPa) at 60° C. 0.41 g of (R,S)-2-imino-8-trifluoromethyl-5,6-dihydro-2H,4H-thiazolo[5,4,3-ij]quinol-6-yl)methanol hydrochloride is thus obtained in the form of an ecru-coloured solid melting above 260° C. with decomposition [$^1$H NMR spectrum in DMSO-d$_6$, T=300K, δ in ppm (250 MHz) 2.20 (2H, m, CH$_2$); 3.20 (1H, t, J=6 Hz, CH), 3.70 (2H, m, OCH$_2$), 4.10 and 4.30 (1H each, m, NCH$_2$), 5.20 (1H, t, J=6 Hz, OH), 7.85 (1H, s, arom. CH), 8.30 (1H, s, arom. CH), 10.80 (2H, s, NH,HCl)].

(R,S)-6-Trifluoromethyl-1,2,3,4-tetrahydroquinoline-4-methanol may be prepared in the following manner: 16.25 g of tin tetrachloride are added dropwise over 5 minutes at −78° C. to a suspension of 8.2 g of N-para-toluenesulphonylmethyl-4-trifluoromethylaniline in 125 ml of dichloromethane. The mixture is stirred for 10 minutes and a solution of 3.6 g of allyl alcohol in 75 ml of dichloromethane is added dropwise over 15 minutes at the same temperature. The mixture is stirred for 2 hours at −78° C. and for 80 hours at a temperature close to 20° C. and then neutralized with 500 ml of a saturated aqueous sodium hydrogen carbonate solution. After addition of 125 ml of distilled water, 125 ml of dichloromethane, filtration and decantation, the aqueous phase is extracted twice with a total of 250 ml of dichloromethane. The organic extracts are combined, washed twice with a total of 250 ml of distilled water, dried over magnesium sulphate and concentrated to dryness under reduced pressure (2 kPa) at 60° C. The product obtained (5.6 g) is chromatographed under nitrogen pressure (150 kPa) on 380 g of 20–45 μm neutral silica gel contained in a column 6.4 cm in diameter, eluting with a mixture of cyclohexane and ethyl acetate (50-50 by volume). 1.25 g of (R,S)-6-trifluoromethyl-1,2,3,4-tetrahydroquinoline-4-methanol are thus obtained in the form of a yellow oil [$^1$H NMR spectrum in DMSO-d$_6$, T=300K, δ in ppm (300 MHz) 1.65 and 1.95 (1H each, m, CH$_2$), 2.80 (1H, m, CH), 3.20 (2H, m, NCH$_2$), 3.50 (2H, m, OCH$_2$), 4.80 (1H, t, J=6 Hz, OH), 6.50 (1H, s, NH), 6.55

(1H, d, J=8 Hz, arom. CH), 7.15 (1H, dd, J=8 and 2 Hz, arom. CH), 7.25 (1H, s, arom. CH)].

EXAMPLE 17

A solution of 3.38 g of (R,S)-N-(2-imino-8-trifluoromethyl)-5,6-dihydro-2H,4H-thiazolo[5,4,3-ij]-quinol-6-yl)-N-methylacetamide in 340 ml of a 2 N aqueous hydrochloric acid solution is heated at boiling temperature for 5 hours, stored for 75 hours at a temperature close to 20° C. and concentrated to dryness under reduced pressure (2.2 kPa) at 100° C. A suspension of 1 g of product obtained (out of the 3.56 g obtained in total) in 60 ml of acetic acid is heated at boiling temperature for 15 minutes, cooled and stored for 1 hour at a temperature close to 20° C. The insoluble matter is separated by filtration, washed twice with a total of 6 ml of acetic acid, twice with a total of 10 ml of ethyl ether and dried under reduced pressure (0.13 kPa) at 60° C. 0.74 g of (R,S)-N-methyl(2-imino-8-trifluoromethyl-5,6-dihydro-2H,4H-thiazolo[5,4,3-ij]-quinol-6-yl)amine dihydrochloride is thus obtained in the form of a white solid melting above 260° C. with decomposition [$^1$H NMR spectrum in DMSO-d$_6$, T=300K, δ in ppm (250 MHz): 2.45 and 2.80 (1H each, m, CH$_2$), 2.65 (3H, s, NCH$_3$), 4.40 (2H, m, NCH$_2$), 4.80 (1H, m, NCH), 8.20 (1H, s, arom. CH), 8.55 (1H, s, arom. CH), 10.10 (2H, s, NH.HCl), 11.20 (2H, broad s, NH.HCl)].

EXAMPLE 18

A solution of 0.4 g of bromine in 5 ml of acetic acid is added dropwise, over 5 minutes at a temperature close to 25° C., to a solution of 0.68 g of (R,S)-4-(1-pyrrolidinyl)-6-trifluoromethyl-1,2,3,4-tetrahydroquinoline and 0.53 g of potassium thiocyanate in 15 ml of acetic acid. The mixture is stirred for 4 hours at a temperature close to 20° C., poured over a mixture of 40 g of ice and 40 ml of distilled water, alkalinized with 35 ml of aqueous ammonia at 28% and extracted 3 times with a total of 150 ml of dichloromethane. The organic extracts are combined, washed with 50 ml of distilled water, dried over magnesium sulphate and concentrated to dryness under reduced pressure (2 kPa) at 30° C. The product obtained (0.68 g) is dissolved in 10 ml of ethanol and the solution, supplemented with decolorizing charcoal, is stirred for 5 minutes and filtered. The filtrate, supplemented with 5 ml of anhydrous hydrochloric ether, is stored for 1 hour at a temperature close to 5° C. and then the solid which appears is separated by filtration, washed twice with a total of 10 ml of anhydrous ether and dried under reduced pressure (0.13 kPa) at 60° C. 0.29 g of (R,S)-2-imino-6-(1-pyrrolidinyl)-8-trifluoromethyl-5,6-dihydro-2H,4H-thiazolo[5,4,3-ij]quinoline is thus obtained in the form of a pale yellow powder melting at 223° C. with decomposition.

(R,S)-4-(1-Pyrrolidinyl)-6-trifluoromethyl-1,2,3,4-tetrahydroquinoline may be prepared in the following manner: 11 ml of a solution at 2 mol per liter in tetrahydrofuran of the borane-methyl sulphide complex is added dropwise over 5 minutes at a temperature close to 20° C. to a solution, kept under an argon atmosphere, of 1.42 g of (R,S)-4-(2-oxo-pyrrolidin-1-yl)-6-trifluoromethyl-1,2,3,4-tetrahydroquinoline in 10 ml of anhydrous tetrahydrofuran. The mixture is stirred for 20 hours at the same temperature, supplemented slowly with 20 ml of distilled water, stirred for 15 minutes and extracted 4 times with a total of 50 ml of dichloromethane. The organic extracts are combined, washed twice with a total of 20 ml of distilled water, dried over magnesium sulphate and concentrated to dryness under reduced pressure (2 kPa) at 30° C. The product obtained (1.25 g) is dissolved in 25 ml of dichloromethane and the solution is extracted 3 times with a total of 30 ml of a 1 N aqueous hydrochloric acid solution. The aqueous extracts are combined, alkalinized with 40 ml of a saturated aqueous sodium hydrogen carbonate solution and extracted 3 times with a total of 60 ml of dichloromethane. The organic extracts are combined, washed with 20 ml of distilled water, dried over magnesium sulphate and concentrated to dryness under reduced pressure (2 kPa) at 30° C. 0.56 g of (R,S)-4-(1-pyrrolidinyl)-6-trifluoromethyl-1,2,3,4-tetrahydroquinoline is thus obtained in the form of a white solid melting at 99° C.

(R,S)-2-Imino-6-(2-oxopyrrolidin-1-yl)-8-trifluoromethyl-5,6-dihydro-2H,4H-thiazolo[5,4,3-ij]-quinoline may be prepared in the following manner: a solution of 0.64 g of bromine in 5 ml of acetic acid is added dropwise, over 10 minutes at a temperature close to 25° C., to a solution of 1 g of (R,S)-4-(2-oxopyrrolidin-1-yl)-6-trifluoromethyl-1,2,3,4-tetrahydroquinoline and 0.85 g of potassium thiocyanate in 25 ml of acetic acid. The mixture is stirred for 3 hours at a temperature close to 20° C., poured over a mixture of 60 g of ice and 60 g of distilled water and extracted with 50 ml of dichloromethane. After decantation, the organic phase is removed and the aqueous phase is alkalinized with 75 ml of aqueous ammonia at 28% and extracted 4 times with a total of 200 ml of dichloromethane. The organic extracts are combined, washed with 50 ml of distilled water, dried over magnesium sulphate and concentrated to dryness under reduced pressure (2 kPa) at 30° C. The product obtained (0.9 g) is dissolved in 20 ml of anhydrous ethyl ether and the mixture is stored for 15 minutes at a temperature close to 20° C. The solid which appears is separated by filtration, washed with 5 ml of anhydrous ether and dried under reduced pressure (0.13 kPa) at 60° C. 0.7 g of (R,S)-2-imino-6-(2-oxopyrrolidin-1-yl)-8-trifluoromethyl-5,6-dihydro-2H,4H-thiazolo[5,4,3-ij]-quinoline is thus obtained melting at 171° C.

(R,S)-4-(2—Oxopyrrolidin-1-yl)-6-trifluoromethyl-1,2,3,4-tetrahydroquinoline may be prepared in the following manner: 13 g of tin tetrachloride are added dropwise over 5 minutes at −78° C. to a suspension of 6.6 g of N-para-toluenesulphonylmethyl-4-trifluoromethylaniline in 100 ml of dichloromethane. The mixture is stirred for 10 minutes and a solution of 2.2 g of 1-vinyl-2-pyrrolidinone in 60 ml of dichloromethane is added dropwise over 10 minutes at the same temperature. The mixture is stirred for 2 hours at −78° C. and for 1 hour at a temperature close to 20° C. The insoluble matter which appears is separated by filtration, washed twice with a total of 100 ml of dichloromethane, suspended in 400 ml of distilled water and 400 ml of dichloromethane and the stirred mixture is neutralized with 400 ml of a saturated aqueous sodium hydrogen carbonate solution and filtered. After decantation, the aqueous phase is extracted 3 times with a total of 600 ml of dichloromethane and the organic extracts are combined, washed with 200 ml of distilled water, dried over magnesium sulphate and concentrated to dryness under reduced pressure (2 kPa) at 60° C. 4.9 g of (R,S)-4-(2-oxopyrrolidin-1-yl)-6-trifluoromethyl-1,2,3,4-tetrahydroquinoline are thus obtained in the form of a white powder melting at 139° C.

EXAMPLE 19

A solution of 2.1 g of bromine in 10 ml of acetic acid is added dropwise, over 15 minutes at a temperature close to 25° C., to a solution of 2.93 g of 7-trifluoromethoxy-2,3-dihydro-4H-[1,4]benzoxazine and 2.83 g of potassium thiocyanate in 40 ml of acetic acid. The mixture is stirred for 2 hours at a temperature close to 20° C., poured over 40 g of ice, alkalinized with 40 ml of aqueous ammonia at 28% and extracted 3 times with a total of 150 ml of ethyl acetate. The organic extracts are combined, dried over magnesium sulphate and concentrated to dryness under reduced pressure (2 kPa) at 60° C. The product obtained (3.1 g) is chromatographed under nitrogen pressure (150 kPa) on 30 g of 20–45 μm neutral silica gel contained in a column 2.5 cm in diameter, eluting with a mixture of ethyl acetate and methanol (95-5 by volume). The product obtained (0.8 g) is dissolved in 5 ml of ethanol and, after addition of 2 ml of 6.5 N hydrochloric ethanol and storing for 1 hour at a temperature close to 5° C., the solid which appears is separated by filtration, washed with 2 ml of ethanol and dried under reduced pressure (0.13 kPa) at 60° C. 0.7 g of 2-imino-8-trifluoromethoxy-4,5-dihydro-2H-thiazolo[3,4,5-de]-[1,4] benzoxazine hydrochloride is thus obtained in the form of a yellow solid melting above 260° C. with decomposition [$^1$H NMR spectrum in DMSO-d$_6$, T=300K, δ in ppm (400 MHz): 4.40 (2H, t, J=6 Hz, NCH$_2$), 4.60 (2H, t, J=6 Hz, OCH$_2$), 7.20 (1H, s, arom. CH), 7.70 (1H, s, arom.CH), 10.80 (2H, broad s, NH,HCl)].

7-Trifluoromethoxy-2,3-dihydro-4H[1,4]-benzoxazine may be prepared in the following manner: a solution of 3.49 g of 7-trifluoromethoxy-4H-[1,4]-benzoxazin-3-one in 20 ml of anhydrous tetrahydrofuran is added dropwise over 35 minutes at a temperature close to 5° C. to 18 ml of a 0.5 M solution of lithium tetrahydroaluminate in tetrahydrofuran kept under an inert atmosphere. The mixture is stirred for 1 hour at a temperature close to 20° C. and then 15 ml of distilled water are added slowly while the temperature is kept below 15° C. The mixture is filtered and the filtrate is extracted 3 times with a total of 150 ml of ethyl acetate. The organic extracts are combined, washed 3 times with a total of 150 ml of distilled water, dried over magnesium sulphate and concentrated to dryness under reduced pressure (2.2 kPa) at 60° C. 2.98 g of 7-trifluoromethoxy-2,3-dihydro-4H-[1,4]benzoxazine are thus obtained in the form of a yellow solid [$^1$H NMR spectrum in CDCl$_3$, T=300K, δ in ppm (300 MHz): 3.30 (2H, t, J=6 Hz, NCH$_2$), 3.70 (1H, broad s, NH), 4.20 (2H, t, J=6 Hz, OCH$_2$), 6.45 (1H, d, J=8 Hz, arom. CH), 6.55 (1H, dd, J=8 and 2 Hz, arom. CH), 6.60 (1H, d, J=2 Hz, arom. CH)].

7-Trifluoromethoxy-4H-[1,4]benzoxazin-3-one may be prepared in the following manner: a solution of 5.6 g of chloroacetyl chloride in 85 ml of chloroform is added dropwise over 30 minutes at a temperature close to 5° C. to a solution of 9.85 g of 2-amino-5-trifluoro-methoxyphenol and 9.8 g of triethylbenzylammonium chloride in 170 ml of chloroform containing, in suspension, 17.3 g of sodium hydrogen carbonate. The mixture is stirred for 1 hour at the same temperature, for 5 hours at the boiling temperature, cooled to a temperature close to 20° C. and concentrated to dryness under reduced pressure (2.2 kPa) at 60° C. The product obtained is suspended in 170 ml of distilled water and then the insoluble matter is separated by filtration, washed 3 times with a total of 255 ml of distilled water and air-dried. The product obtained (8.78 g) is chromatographed under nitrogen pressure (150 kPa) on 200 g of 20–45 μm neutral silica gel contained in a column 5.5 cm in diameter, eluting with dichloromethane. 3.49 g of 7-trifluoromethoxy-4H-[1,4]-benzoxazin-3-one are thus obtained in the form of a yellow solid melting at around 150° C.

2-Amino-5-trifluoromethoxyphenol may be prepared in the following manner: 12 g of tert-butyl N-(2-hydroxy-4-trifluoromethoxyphenyl)carbamate are added over 15 minutes at a temperature close to 25° C. to 225 ml of a 6.5 N hydrochloric dioxane solution. The mixture is stirred for 3 hours at the same temperature and concentrated to dryness under reduced pressure (2.2 kPa) at 600° C. 9.85 g of 2-amino-5-trifluoromethoxyphenol hydrochloride are thus obtained in the form of a beige solid subliming at 170° C. [$^1$H NMR spectrum in DMSO-d$_6$, T=300K, δ in ppm (300 MHz): 6.90 (1H, dd, J=8 and 2 Hz, arom. CH), 7.05 (1H, s, arom. CH), 7.45 (1H, d, J=8 Hz, arom. CH), 9.50 (3H, broad s, NH$_2$-HCl), 11.20 (1H, s, OH)].

tert-Butyl N-(2-hydroxy-4-trifluoromethoxyphenyl) carbamate may be prepared in the following manner: 69 ml of a 1.5 M solution of tert-butyllithium in pentane are added dropwise over 1 hour at −70° C. to a solution, kept under an inert atmosphere, of 12 g of tert-butyl N-(4-trifluoromethoxyphenyl)carbamate in 130 ml of anhydrous tetrahydrofuran. The mixture is stirred for 2 hours at −20° C., cooled to −70° C. and 13.9 g of trimethyl borate are added dropwise over 15 minutes. The mixture is stirred for 1 hour and 30 minutes at −20° C. and 7.8 ml of acetic acid are added dropwise over 15 minutes at −5° C. The mixture is stirred for 5 minutes and 28.6 ml of hydrogen peroxide at 16% are added dropwise over 15 minutes at 0° C. The mixture is stirred, while the temperature is allowed to rise to 20° C., and then 65 ml of distilled water and 170 ml of ethyl ether are added. After decantation, the ethereal phase is washed with an aqueous sodium bisulphite solution, with distilled water and with a saturated sodium chloride solution, dried over magnesium sulphate and concentrated to dryness under reduced pressure (2.2 kPa) at 60° C. 12 g of tert-butyl N-(2-hydroxy-4-trifluoromethoxyphenyl) carbamate are thus obtained in the form of a yellow solid melting at 102° C.

EXAMPLE 20

The procedure is carried out as in Example 1, but starting with 3.8 g of bromine diluted in 21 ml of acetic acid, 5.3 g of potassium thiocyanate and 5.5 g of (R,S)-6-trifluoromethyl-1,2,3,4-tetrahydroquinoline-2-methanol in 71 ml of acetic acid. 0.6 g of (R,S)-2-imino-8-trifluoromethyl-5,6-dihydro-2H,4H-thiazolo[5,4,3-ij] quinoline-4-methanol hydrochloride is thus obtained, melting at 265° C. with decomposition [Analysis C$_{12}$H$_{12}$ClF$_3$N$_2$OS, % calculated C: 44.38, H: 3.72, Cl: 10.92, F: 17.55, N: 8.63, O: 4.93, S: 9.87,% found C: 44.6, H: 4.1, Cl: 11.0, F: 17.1, N: 8.5, S: 9.5].

(R,S)-6-Trifluoromethyl-1,2,3,4-tetrahydroquinoline-2-methanol may be prepared as in Example 1, but starting with 6.4 g of 6-trifluoromethylquinoline-2-methanol and 0.5 g of platinum oxide in 60 ml of methanol. 5.5 g of (R,S)-6-trifluoromethyl-1,2,3,4-tetrahydroquinoline-2-methanol are obtained in the form of a light-coloured oil [$^1$H NMR spectrum in DMSO-d$_6$, T=300K, δ in ppm (300 MHz): 1.55 and 1.85 (1H each, m, CH$_2$), 2.75 (2H, t, J=6 Hz, CH$_2$), 3.40 (1H, m, NCH), 3.48 (2H, broad t, CH$_2$O), 4.90 (1H, t, J=5 Hz, OH), 6.40 (1H, s, NH), 6.70 (1H, d, J=8 Hz, arom. CH), 7.20 (2H, m, arom. CH)].

6-Trifluoromethylquinoline-2-methanol may be prepared as in Example 7, but starting with 45.5 g of 2-methyl-6-trifluoromethylquinoline 1-oxide in 200 ml of acetic anhydride. 6.4 g of 6-trifluoromethylquinoline-2-methanol are thus obtained in the form of a brownish solid melting at 85° C.

2-Methyl-6-trifluoromethylquinoline 1-oxide may be prepared as in Example 6, but starting with 10.5 g of 2-methyl-6-trifluoromethylquinoline and 41 g of 3-chloroperbenzoic acid in 200 ml of dichloromethane. 11.6 g of 2-methyl-6-trifluoromethylquinoline 1-oxide are thus obtained in the form of a pasty solid [$^1$H NMR spectrum in CDCl$_3$, T=300K, δ in ppm (300 MHz): 2.75 (3H, s, CH$_3$), 7.45 (1H, d, J=8 Hz, arom. CH), 7.75 (1H, d, J=8 Hz, arom. CH), 7.90 (1H, dd, J=8 and 2 Hz, arom. CH), 8.15 (1H, s, arom. CH), 8.90 (1H, d, J=8 Hz, arom. CH)].

EXAMPLE 21

The procedure is carried out as in Example 9, but starting with 1 g of 2-imino-8-trifluoromethyl-4,5-dihydro-2H-thiazolo[3,4,5-de] [1,4]benzothiazine and 4.2 g of 3-chloroperbenzoic acid (80% purity) in 20 ml of dichloromethane. 720 mg of 2-imino-8-trifluoromethyl-4,5-dihydro-2H-thiazolo[3,4,5-de] [1,4]benzothiazine-6,6-dioxide methane sulphonate are thus obtained in the form of a white powder melting at a temperature greater than 260° C. [Analysis C$_{11}$H$_{11}$F$_3$N$_2$O$_5$S$_3$, % calculated C: 32.67,H: 2.74, F: 14.09, N: 6.93, S: 23.79,% found C: 46.6,H: 4.1, Cl: 11.0, F: 17.1, N: 8.5, S: 9.51].

EXAMPLE 22

2.07 g of bromine diluted in 6.75 ml of acetic acid are added dropwise over 10 minutes, at a temperature close to 20° C. and under argon, to a solution of 3.6 g of potassium thiocyanate and 3.43 g of 7-trifluoromethyl-3,4-dihydro-2H-benzo[b] [1,4]-selenazine in 52 ml of acetic acid. The reaction mixture is stirred for 3 hours at the same temperature, poured over ice, alkalinized with a solution of aqueous ammonia at 20% and extracted with 100 ml of ethyl acetate. The organic phase is washed with 50 ml of distilled water, dried over magnesium sulphate and concentrated to dryness under reduced pressure (4 kPa) at 40° C. The crude product is chromatographed on a silica gel column, eluting with a mixture of cyclohexane and ethyl acetate (50-50 by volume) to give 2.2 g of a pale yellow solid. The latter, after decolorizing by means of vegetable charcoal in ethyl ether under reflux, yields 2.7 g of 2-imino-8-trifluoromethyl-4,5-dihydro-2H-thiazolo[5,4,3-de]-1,4-benzoselenazine in the form of white crystals melting at 130° C. [$^1$H NMR spectrum in DMSO-d$_6$, T=300K, δ in ppm (300 MHz): 3.30 (2H, t, J=6 Hz, SeCH$_2$), 4.30 (2H, t, J=6 Hz, NCH$_2$), 7.60 (1H, s, arom. CH), 7.75 (1H, s, arom. CH), 8.80 (1H, s, NH)]

7-Trifluoromethyl-3,4-dihydro-2H-benzo[b]-[1,4] selenazine may be prepared in the following manner: 35.5 ml of a 2 N solution, in tetrahydrofuran, of the borane-methyl sulphide complex are added dropwise, under argon and at a temperature close to 20° C., to a suspension of 10.5 g of 7-trifluoromethyl-3,4-dihydro-2H-benzo[b] [1,4] selenazin-3-one in 255 ml of toluene. The reaction medium is then heated to and kept at the boiling temperature for 1 hour 45 minutes. After cooling to around 20° C., it is hydrolysed with 600 ml of a saturated sodium hydrogen carbonate solution, and then extracted with 3 times 100 ml of ethyl acetate. The combined organic phases are washed with 100 ml of distilled water, dried over magnesium sulphate and concentrated to dryness under reduced pressure (4 kPa) at 40° C. After trituration of the residue in petroleum ether, 9.65 g of 7-trifluoromethyl-3,4-dihydro-2H-benzo[b] [1,4]selenazine are obtained in the form of whitish crystals melting at 55° C.

7-Trifluoromethyl-3,4-dihydro-2H-benzo[b]-[1,4] selenazin-3-one may be prepared in the following manner: 15 ml of trifluoroacetic acid are added to a solution of 17 g of ethyl 2-(2-tert-butoxycarbonylamino-5-trifluoromethylphenylselanyl)acetate in 150 ml of dichloromethane. After 29 hours at a temperature close to 20° C., the reaction medium is treated with 250 ml of a saturated sodium hydrogen carbonate solution and extracted with 250 ml of ethyl acetate. The organic phase is washed with distilled water, dried over magnesium sulphate and concentrated to dryness under reduced pressure (4 kPa) at 40° C. After trituration of the residue in a mixture of ethyl ether and petroleum ether, 10.5 g of 7-trifluoromethyl-3,4-dihydro-2H-benzo[b] [1,4]selenazin-3-one are obtained in the form of white crystals melting at 207° C.

Ethyl 2-(2-tert-butoxycarbonylamino-5-trifluoromethylphenylselanyl)acetate may be prepared in the following manner: 1 g of sodium tetrahydroborate is added in small portions, at a temperature close to 20° C. and under argon, to a solution of 14.47 g of tert-butyl N-[2-(2-tert-butoxycarbonylamino-5-trifluoromethylphenyldiselanyl)-4-trifluoromethylphenyl]carbamate in a mixture of 100 ml of ethanol and 150 ml of tetrahydrofuran. After 10 minutes, the solution of 7.5 g of ethyl bromoacetate in 5 ml of tetrahydrofuran is poured in dropwise. 0.6 g of sodium tetrahydroborate is again added in several portions over 1 hour. The reaction medium is then poured over 150 ml of an approximately 4 N ammonium chloride solution and extracted with 250 ml of ethyl ether. The organic phase is concentrated until 2 phases appear, and the residue is again extracted with 200 ml of ethyl ether. The organic phase is washed with distilled water, dried over magnesium sulphate and concentrated to dryness under reduced pressure (4 kPa) at 40° C. The crude product is redissolved, at a temperature close to 20° C. and under argon, in 100 ml of dimethylformamide. 0.5 g of sodium tetrahydroborate is added in small portions, followed by 3 g of ethyl bromoacetate. After about 20 minutes, the mixture is treated with 200 ml of an approximately 4 N ammonium chloride solution and extracted with twice 100 ml of ethyl acetate. The combined organic phases are washed with 100 ml of distilled water, dried over magnesium sulphate and concentrated to dryness under reduced pressure (4 kPa) at 40° C. After trituration of the residue in petroleum ether, 10.85 g of ethyl 2-(2-tert-butoxycarbonylamino-5-trifluoromethylphenylselanyl) acetate are obtained in the form of white crystals melting at 69° C.

tert-Butyl N-[2-(2-tert-butoxycarbonylamino-5-trifluoromethylphenyldiselanyl)-4-trifluoromethylphenyl] carbamate may be prepared in the following manner: 200 ml of a solution (about 1.7 M) of tert-butyllithium in pentane are added dropwise over 30 minutes to a solution of 42 g of tert-butyl 4-trifluoromethylphenylcarbamate in 300 ml of anhydrous tetrahydrofuran, kept under an argon atmosphere at a temperature of less than −20° C. The mixture is stirred for 2 hours at the same temperature and then 13.5 g of selenium powder are added at −30° C. The mixture is stirred for 35 minutes at around −15° C. and is then supplemented with 100 ml of a saturated ammonium chloride solution and the temperature allowed to rise to around 20° C. It is then stirred at this temperature, in contact with air, for 18 hours, and then extracted with 600 ml of ethyl ether. The organic phase is dried over magnesium sulphate and concentrated to dryness under reduced pressure (4 kPa) at 40° C. The product obtained is filtered on silica gel, eluting with a mixture of cyclohexane and ethyl acetate (65-35 by volume). After trituration in petroleum ether, 39.1 g of tert-butyl N-[2-(2-tert-butoxycarbonylamino-5-trifluoromethylphenyldiselanyl)-4-trifluoromethylphenyl]-carbamate are obtained in the form of yellow crystals melting at 150° C.

EXAMPLE 23

5.05 g of bromine diluted in 10 ml of acetic acid are added dropwise over 10 minutes, at a temperature close to 20° C.

and under argon, to a solution of 9.3 g of potassium thiocyanate and 4 g of 3,3-difluoro-6-trifluoromethyl-1,2,3,4-tetrahydro-4-quinolinol in 180 ml of acetic acid. The reaction mixture is stirred for 18 hours at the same temperature, poured over ice, alkalinized with a solution of aqueous ammonia at 20% and extracted with 200 ml of ethyl acetate. The organic phase is dried over magnesium sulphate and concentrated to dryness under reduced pressure (4 kPa) at 40° C. The crude product is chromatographed on a silica gel column, eluting with a mixture of cyclohexane and ethyl acetate (65-35 and then 35-65 by volume) to give a yellow oil. The latter is redissolved in ethyl ether and supplemented with a solution of hydrochloric ether. The solid obtained is dissolved in isopropanol and then reprecipitated by addition of isopropyl acetate. 0.32 g of (R,S)-5,5-difluoro-6-hydroxy-2-imino-8-trifluoromethyl-5,6-dihydro-2H,4H-thiazolo[5,4,3-ij]quinoline hydrochloride is obtained in the form of a white solid melting above 200° C. with decomposition [$^1$H NMR spectrum in DMSO-$d_6$, T=300K, δ in ppm (300 MHz): 4.75 (2H, m, NCH$_2$), 5.30 (1H, dd, J=9 and 3 Hz, OCH), 7.15 (1H, s, OH), 8.00 (1H, s, arom. CH), 8.50 (1H, s, arom. CH), 11.20 (2H, s, NH.HCl)]

3,3-Difluoro-6-trifluoromethyl-1,2,3,4-tetrahydro-4-quinolinol may be prepared in the following manner: 30 ml of borane-methyl sulphide complex are added dropwise, under argon and at a temperature close to 20° C., to a suspension of 10.76 g of 3,3-difluoro-4-hydroxy-6-trifluoromethyl-1,2,3,4-tetrahydro-2-quinolinone in 250 ml of toluene. The reaction medium is then heated to and kept at the boiling temperature for 1 hour and 10 minutes. After cooling to around 20° C., it is hydrolysed with 100 ml of a saturated sodium hydrogen carbonate solution and then the organic phase is dried over magnesium sulphate and concentrated to dryness under reduced pressure (4 kPa) at 40° C. The residue is treated with a dilute solution of hydrochloric acid and extracted with ethyl ether. The organic phase is dried over magnesium sulphate and concentrated to dryness under reduced pressure (4 kPa) at 40° C. After trituration of the residue in petroleum ether, 7.1 g of 3,3-difluoro-6-trifluoromethyl-1,2,3,4-tetrahydro-4-quinolinol are obtained in the form of pink crystals melting at 110° C.

3,3-Difluoro-4-hydroxy-6-trifluoromethyl-1,2,3,4-tetrahydro-2-quinolinone may be prepared in the following manner: 35 ml of about 6 N hydrochloric dioxane are added to a solution of 11.85 g of ethyl 3-(2-tert-butoxycarbonylamino-5-trifluoromethylphenyl)-2,2-difluoro-3-hydroxypropanoate in 65 ml of dioxane. After 18 hours at a temperature close to 20° C., the reaction medium is concentrated under vacuum, and then the residue is treated with 50 ml of a saturated sodium hydrogen carbonate solution and extracted with 200 ml of ethyl acetate. The organic phase is dried over magnesium sulphate and concentrated to dryness under reduced pressure (4 kPa) at 40° C. After trituration of the residue in petroleum ether, 6.8 g of 3,3-difluoro-4-hydroxy-6-trifluoromethyl-1,2,3,4-tetrahydro-2-quinolinone are obtained in the form of a cream-coloured solid melting at 171° C.

Ethyl 3-(2-tert-butoxycarbonylamino-5-trifluoromethylphenyl)-2,2-difluoro-3-hydroxypropanoate may be prepared in the following manner: 1.22 g of ethyl bromodifluoroacetate, 0.75 g of zinc powder and 0.3 g of iodine are added to a solution of 1.45 g of tert-butyl 2-formyl-4-trifluoromethylphenylaminocarboxylate in 10 ml of dioxane. The reaction medium is then sonicated for 3 hours at a temperature passing from 30 to 50° C. After cooling to around 0° C. and adding 100 ml of ethyl acetate, the mixture is filtered and then a saturated sodium chloride solution is added. The organic phase is dried over magnesium sulphate and concentrated to dryness under reduced pressure (4 kPa) at 40° C. The crude product is chromatographed on a silica gel column, eluting with a mixture of cyclohexane and ethyl acetate (70-30 by volume) to give 0.85 g of ethyl 3-(2-tert-butoxycarbonylamino-5-trifluoromethylphenyl)-2,2-difluoro-3-hydroxypropanoate in the form of a light-coloured oil [$^1$H NMR spectrum in DMSO-$d_6$, T=300K, δ in ppm (250 MHz) 1.25 (3H, t, J=6 Hz, CH$_3$), 1.50 (9H, s, (CH$_3$)$_3$), 4.28 (2H, q, J=6 Hz, OCH$_2$), 5.65 (1H, m, OCH), 7.42 (1H, d, J=4 Hz, OH), 7.70 (1H, d, J=8 Hz, arom. CH), 7.76 (1H, s, arom. CH), 7.94 (1H, d, J=8 Hz, arom. CH), 9.18 (1H, s, NH)].

tert-Butyl 2-formyl-4-trifluoromethylphenylaminocarboxylate may be prepared by the method described in C.A 107: 39815x.

EXAMPLE 24

The procedure is carried out as in Example 23, but starting with 1.55 g of bromine in 2 ml of acetic acid, 2.8 g of potassium thiocyanate and 2.3 g of 3,3-difluoro-6-trifluoromethyl-1,2,3,4-tetrahydroquinoline in 30 ml of acetic acid. The crude product is chromatographed on a silica gel column, eluting with a mixture of cyclohexane and ethyl acetate (50-50 by volume) to give about 0.35 g of a whitish solid melting at around 85° C. The latter is redissolved in ethyl ether and supplemented with 0.1 ml of methanesulphonic acid. After trituration of the solid obtained in ethyl ether, 0.35 g of 5,5-difluoro-2-imino-8-trifluoromethyl-5,6-dihydro-2H,4H-thiazolo[5,4,3-ij]quinoline methanesulphonate is obtained in the form of a white solid melting above 235° C. with decomposition [$^1$H NMR spectrum in DMSO-$d_6$, T=300K, δ in ppm (300 MHz): 2.35 (3H, s, CH$_3$SO$_3$H), 3.80 (2H, t, J=-16 Hz, CH$_2$), 4.65 (2H, t, J=13 Hz, CH$_2$)$_1$ 7.90 (1H, s, arom. CH), 8.40 (1H, s, arom. CH), 10.70 (1H, s, NH)].

3,3-Difluoro-6-trifluoromethyl-1,2,3,4-tetrahydroquinoline may be prepared in the following manner: 1 ml of triethylsilane and 3 ml of trifluoroacetic acid are added, under argon and at a temperature close to 20° C., to a solution of 0.7 g of 3,3-difluoro-6-trifluoromethyl-1,2,3,4-tetrahydro-4-quinolinol in 15 ml of dichloromethane. The reaction medium is stirred for 4 hours at the same temperature, poured over ice, alkalinized with a solution of aqueous ammonia at 20% and extracted twice with a mixture of ethyl acetate and ethyl ether. The organic extracts are combined, washed with a dilute sodium chloride solution, dried over magnesium sulphate and concentrated to dryness under reduced pressure (4 kPa) at 40° C. The crude product is chromatographed on a silica gel column, eluting with a mixture of cyclohexane and ethyl acetate (80-20 by volume) to give 0.18 g of 3,3-difluoro-6-trifluoromethyl-1,2,3,4-tetrahydroquinoline in the form of a colourless oil [$^1$H NMR spectrum in DMSO-$d_6$, T=300K, δ in ppm (250 MHz): 3.30 (2H, t, J=15 Hz, CH$_2$), 3.55 (2H, t, J=12 Hz, NCH$_2$), 6.70 (1H, d, J=8 Hz, arom. CH), 6.83 (1H, s, NH), 7.30 (1H, d, J=8 Hz, arom. CH), 7.32 (1H, s, arom. CH)].

EXAMPLE 25

The procedure is carried out as in Example 23, but starting with 2.93 g of bromine in 5 ml of acetic acid, 5.3 g of potassium thiocyanate and 3.7 g of 6-trifluoromethyl-1,2,3,4-tetrahydroquinoxaline in 60 ml of acetic acid. The crude product is chromatographed on a silica gel column, eluting with a mixture of ethyl acetate and methanol (95-5 by volume) to give about 1.8 g of a yellow oil. The latter is dissolved in ethyl ether and supplemented with hydrochloric ether. After trituration of the solid obtained in ethyl ether, it is isolated by filtration, and then redissolved in water. The solution is alkalinized with aqueous ammonia at 20% and extracted with twice 100 ml of ethyl acetate. The organic extracts are combined, washed with distilled water, dried over magnesium sulphate and concentrated to dryness under reduced pressure (4 kPa) at 40° C. The oily residue obtained is chromatographed on a silica gel column, eluting with a mixture of tetrahydrofuran, cyclohexane and ethanol (59.7-40-0.3 by volume). 0.75 g of 2-imino-8-trifluoromethyl-5, 6-dihydro-2H,4H-thiazolo[3,4,5-de]quinoxaline is thus obtained in the form of a white solid melting at 112° C. [$^1$H NMR spectrum in DMSO-$d_6$, T=300K, δ in ppm (250 MHz) 3.40 (2H, d, J=5 Hz, $NCH_2$), 3.80 (2H, d, J=5 Hz, $NCH_2$), 6.43 (1H, s, NH), 6.78 (1H, s, arom. CH), 7.12 (1H, s, arom. CH), 8.35 (1H, s, NH)].

6-Trifluoromethyl-1,2,3,4-tetrahydroquinoxaline may be prepared by the method described by Rao et al., J. Heterocycl. Chem., (1973), 10(2), 213–5.

EXAMPLE 26

The procedure is carried out as in Example 23, but starting with 0.45 g of bromine in 2 ml of acetic acid, 0.7 g of 2-hydroxymethyl-7-trifluoromethyl-3,4-dihydro-2H-[1,4] benzothiazine and 0.6 g of potassium thiocyanate in 10 ml of acetic acid. The product obtained is suspended in isopropyl ether and ethyl ether, separated by filtration, washed with isopropyl ether and dried under reduced pressure. 0.188 g of the product thus obtained (out of 0.470 g obtained in total) is dissolved in 15 ml of ethanol to which 0.044 ml of methanesulphonic acid is added. After stirring for 1 hour at 20° C., the solution is concentrated to dryness under reduced pressure (2 kPa) and the product is taken up in 10 ml of acetone, separated by filtration, washed with twice 5 ml of acetone, dried for 16 hours under a ventilated fume cupboard. 0.215 g of 5-hydroxymethyl-2-imino-8-trifluoromethyl-4,5-dihydro-2H-thiazolo[3,4,5-de] [1,4] benzothiazine methanesulphonate is thus obtained in the form of a white solid melting at 216° C. [Analysis $C_{12}H_{13}F_3N_2O_4S_3$, % calculated C: 35.82,H: 3.26, F: 14.16, N: 6.96, O: 15.90, S: 23.90,% found C: 35.91,H: 3.13, F: 14.12, N: 6.73, S: 24.11].

2-Hydroxymethyl-7-trifluoromethyl-3,4-dihydro-2H-[1, 4]benzothiazine may be prepared in the following manner: 6 ml of an approximately 2 M solution of borane-dimethyl sulphide complex in tetrahydrofuran are rapidly added to a solution of 1.7 g of 2-methoxycarbonyl-7-trifluoromethyl-3,4-dihydro-2H-[1,4]benzothiazine in 50 ml of toluene and about 10 ml of tetrahydrofuran, kept under argon. The reaction mixture is heated for 1 hour under reflux, and then after returning to 20° C. is hydrolysed with 70 ml of a saturated aqueous sodium hydrogen carbonate solution and 40 ml of ethyl acetate. The insoluble matter is removed by filtration and the filtrate is separated after settling out, the organic phase is dried over magnesium sulphate and concentrated to dryness under reduced pressure (2 kPa). The yellow oil obtained is chromatographed on 35 g of 20–45 gm silica gel contained in a column 2 cm in diameter, eluting with an ethyl acetate and cyclohexane mixture (75-25 by volume). 0.72 g of 2-hydroxymethyl-7-trifluoromethyl- 3,4-dihydro-2H-[1,4]benzothiazine is thus obtained in the form of a yellow solid melting at 80° C.

2-Methoxycarbonyl-7-trifluoromethyl-3,4-dihydro-2H-[1,4]benzothiazine may be prepared in the following manner: a mixture of 2.55 g of 2-methoxycarbonyl-7-trifluoromethyl-4H-[1,4]benzothiazine, 9 g of magnesium turnings in 100 ml of methanol is heated to about 45° C. After starting the reaction, the temperature rises to the reflux temperature and stays there by itself. After returning to about 20° C., the reaction medium is diluted with 50 ml of methanol and stirred for 16 hours at about 20° C. The medium, cooled to around 0° C., is hydrolysed with 154 ml of 4 N hydrochloric acid, stirred for 1 hour and then filtered on a celite 545 bed. The celite is successively washed with 500 ml of dichloromethane and 40 ml of acetone. The organic phase is then washed with 200 ml of distilled water, dried over magnesium sulphate and concentrated to dryness under reduced pressure (2 kPa). 1.75 g of 2-methoxycarbonyl-7-trifluoromethyl-3,4-dihydro-2H-[1,4] benzothiazine are thus obtained in the form of a brown oil which is used as it is.

2-Methoxycarbonyl-7-trifluoromethyl-4H-[1,4] benzothiazine may be prepared in the following manner: a mixture of 7.8 g of methyl 2-(2-tert-butoxycarbonylamino-5-trifluoromethylphenylsulphanyl)-3-dimethylaminoacrylate, 10.3 g of trifluoroacetic acid and 80 ml of anhydrous dichloromethane is stirred for 24 hours at about 20° C. After concentrating to dryness under reduced pressure, the residue is taken up in 200 ml of a saturated aqueous sodium hydrogen carbonate solution and extracted with twice 200 ml of ethyl acetate. The combined organic extracts are dried over magnesium sulphate, concentrated to dryness under reduced pressure (2 kPa) and the product obtained is resuspended in isopropyl ether. The solid is separated by filtration, washed with isopropyl ether and dried under reduced pressure. 2.57 g of 2-methoxycarbonyl-7-trifluoromethyl-4H-[1,4]benzothiazine are obtained in the form of an orange-coloured solid melting at 238° C.

Methyl 2-(2-tert-butoxycarbonylamino-5-trifluoromethylphenylsulphanyl)-3-dimethylaminoacrylate may be prepared in the following manner: a mixture, kept under argon, of 10.95 g of methyl (5-trifluoromethyl-2-tert-butoxycarbonylaminophenyl)sulphanylacetate, 15.5 g of tert-butoxy-bis(dimethylamino)methane and 300 ml of anhydrous dichloromethane is heated under reflux for 7 hours. After returning to about 20° C. and stirring for 16 hours, the medium is concentrated to dryness under reduced pressure and the product obtained is resuspended in 20 ml of isopropyl ether. The solid is separated by filtration, washed three times with isopropyl ether and dried under reduced pressure. 3.4 g of methyl 2-(2-tert-butoxycarbonylamino-5-trifluoromethylphenylsulphanyl)- 3-dimethylaminoacrylate are thus obtained in the form of a cream-coloured solid melting at 139° C. The filtrate of the solid previously obtained is concentrated to dryness under reduced pressure (2 kPa) and the product obtained is chromatographed under nitrogen pressure (150 kPa) on 75 g of 20–45 gm silica gel contained in a column 2.5 cm in diameter, eluting with a mixture of cyclohexane and ethyl acetate (80-20 by volume). 4.45 g of methyl 2-(2-tert-butoxycarbonylamino-5-trifluoromethylphenylsulphanyl)-3-dimethylaminoacrylate are thus obtained in the form of a cream-coloured solid melting at 140° C.

EXAMPLE 27

The procedure is carried out as in Example 23, but starting with 6.55 g of bromine in 20 ml of acetic acid, 9.6 g of (R,S)-2-methyl-7-trifluoromethyl-3,4-dihydro-2H-[1,4] benzothiazine and 8.9 g of potassium thiocyanate in 100 ml of acetic acid. The product obtained is chromatographed under nitrogen pressure (150 kPa) on 120 g of 20–45 gm silica gel contained in a column 3 cm in diameter, eluting with a mixture of ethyl acetate and cyclohexane (50-50 by volume). The product obtained (9.9 g) is dissolved in 150 ml of absolute ethanol to which 2.7 ml of methanesulphonic acid are added. After stirring for 5 hours 30 min at about 20° C., the product is separated by filtration, washed with absolute ethanol and then isopropyl ether, and dried under reduced pressure. 10.7 g of (R,S)-2-imino-5-methyl-8-trifluoromethyl-4,5-dihydro-2H-thiazolo[3,4,5-de] [1,4] benzothiazine methanesulphonate are thus obtained in the form ofacru-ecru-coloured crystals melting at a temperature greater than 260° C. [Analysis $C_{12}H_{13}F_3N_2O_3S_3$, % calculated C: 37.30,H: 3.39, F: 14.75, N: 7.25, O: 12.42, S: 24.89, % found C: 37.66,H: 3.24, F: 14.55, N: 7.30, S: 25.30].

(R,S)-2-methyl-7-trifluoromethyl-3,4-dihydro-2H-[1,4] benzothiazine may be prepared in the following manner: 44 ml of an approximately 2 M solution of borane-dimethyl sulphide complex in tetrahydrofuran are added, over 10 minutes, to a mixture of 11.5 g of (R,S)-2-methyl-7-trifluoromethyl-2,4-dihydro[1,4]benzothiazin-3-one in 320 ml of toluene. The reaction medium is heated for 2 hours under reflux and then, after returning to about 20° C., is poured over 400 ml of a saturated aqueous sodium hydrogen carbonate solution and 200 ml of distilled water. The product is extracted twice with 150 ml of ethyl acetate. The combined organic extracts are dried over magnesium sulphate, concentrated to dryness under reduced pressure and the product thus obtained is resuspended in petroleum ether and then separated by filtration, washed with petroleum ether and dried under reduced pressure. 9.60 g of (R,S)-2-methyl-7-trifluoromethyl-3,4-dihydro-2H-[1,4]benzothiazine are thus obtained in the form of a cream-coloured solid melting at 112° C.

(R,S)-2-methyl-7-trifluoromethyl-2,4-dihydro[1,4] benzothiazin-3-one may be prepared in the following manner: a mixture of 30.1 g of ethyl (R,S)-2-(2-tert-butoxycarbonylamino-5-trifluoromethylphenylsulphanyl) propionate, 43 g of trifluoroacetic acid and 90 ml of dichloromethane is stirred at about 20° C. for 16 hours. The solvent is then removed by concentrating under reduced pressure and replaced with 150 ml of tetrahydrofuran. The mixture is heated for 24 hours under reflux and then concentrated to dryness under reduced pressure (2 kPa) and the product obtained is resuspended in isopropyl ether, separated by filtration, washed with isopropyl ether and dried under reduced pressure. 10.6 g of (R,S)-2-methyl-7-trifluoromethyl-2,4-dihydro-[1,4]benzothiazin-3-one are thus obtained in the form of a chestnut-coloured solid melting at 200° C.

Ethyl (R,S)-2-(2-tert-butoxycarbonylamino-5-trifluoromethylphenylsulphanyl)propionate may be prepared in the following manner: 100 ml of a solution (about 1.7 M) of tert-butyllithium in pentane are added dropwise to a solution of 20 g of tert-butyl 4-trifluoromethylphenylcarbamate in 260 ml of anhydrous tetrahydrofuran kept under an argon atmosphere at a temperature of less than −70° C. The mixture is stirred for 3 hours 30 minutes at a temperature kept at about −20° C., and then cooled to around −70° C. before adding 2.5 g of sulphur and allowing the temperature to rise to around −20° C., keeping the mixture at this temperature for 1 hour. The temperature is again brought to around −50° C. and 13.95 g of ethyl (R,S)-2-bromopropionate are added all at once. The temperature is brought to around 20° C. and thus stirred for 48 hours. After adding distilled water, the mixture is extracted twice with ethyl acetate. The organic extracts are combined, dried over magnesium sulphate and concentrated to dryness under reduced pressure (2 kPa). 30.1 g of ethyl (R,S)-2-(2-tert-butoxycarbonylamino-5-trifluoromethylphenylsulphanyl)propionate are thus obtained in the form of an amber-coloured oil which is used without further purification. [$^1$H NMR spectrum in DMSO-$d_6$, T=300K, δ in ppm (300 MHz): 1.08 (3H, t, J=6 Hz, $CH_3$), 1.39 (3H, d, J=6 Hz, $CH_3$), 1.50 (9H, s, $(CH_3)_3$), 4.00 (3H, m, SCH and $OCH_2$), 7.72 (1H, d, J=8 Hz, arom. CH), 7.67 (1H, s, arom. CH), 8.05 (1H, d, J=8 Hz, arom. CH), 8.52 (1H, s, NH)].

EXAMPLE 28

0.87 g of bromine diluted in 5 ml of acetic acid is added dropwise, at a temperature close to 20° C. and under argon, to a solution of 1.2 g of p thiocyanate and 1.4 g of (R,S)-dimethyl(6-trifluoromethyl-1,2,3,4-tetrahydroquinol-2-ylmethyl)amine in 16 ml of acetic acid. The reaction mixture is stirred for 18 hours at the same temperature, poured over ice, alkalinized with a solution of aqueous ammonia at 320 and extracted twice with a total of 75 ml of ethyl acetate. The organic extracts are combined, dried over magnesium sulphate and concentrated to dryness under reduced pressure (4 kPa) at 40° C. The crude product is chromatographed on silica gel, eluting with a mixture of dichloromethane and methanol (99-1 and then 98-2 by volume) to give a brown oil. The latter is redissolved in ethyl ether, decolorized by means of activated charcoal and then supplemented with a solution of hydrochloric isopropanol. 1 g of (R,S)-dimethyl(2-imino-8-trifluoromethyl-5,6-dihydro-2H,4H-thiazolo[5,4,3-ij]quinol-4-ylmethyl)amine dihydrochloride is obtained in the form of a cream-coloured solid melting at around 210° C. with decomposition [Analysis $C_{14}H_{18}ClF_3N_3S$, % calculated C: 43.31,H: 4.67, Cl: 18.26, F: 14.68, N: 10.82, S: 8.26, % found C: 43.0,H: 5.0, Cl: 18.0, F: 14.2, N: 10.5, S: 7.8]

(R,S)-dimethyl(6-trifluoromethyl-1,2,3,4-tetrahydroquinol-2-ylmethyl)amine may be prepared in the following manner: 0.84 g of sodium tetrahydroborate is added under argon and at a temperature close to 20° C., over 30 minutes, to a suspension of 1.4 g of dimethyl(6-trifluoromethylquinol-2-ylmethyl)amine and 0.23 g of nickel(II) chloride hexahydrate in 21 ml of methanol. After stirring for 18 hours and 21 hours at this temperature, there are added in 2 portions 0.12 g of nickel(II) chloride hexahydrate and 0.42 g of sodium tetrahydroborate. The reaction medium is again stirred for 18 hours after the last addition and then concentrated under reduced pressure (4 kPa) at 40° C. The residue is taken up in 30 ml of a 10% hydrochloric acid solution, then alkalinized by means of a solution of aqueous ammonia at 32% and extracted twice with a total of 150 ml of ethyl acetate. The organic extracts are combined, dried over magnesium sulphate and concentrated to dryness under reduced pressure (4 kPa) at 40° C. The crude product is chromatographed on a silica gel column, eluting with a mixture of dichloromethane and methanol (99-1 and then 98-2 by volume). 1.5 g of (R,S)-dimethyl(6-trifluoromethyl-1,2,3,4-tetrahydroquinol-2-ylmethyl)amine are thus obtained in the form of a brown oil [$^1$H NMR spectrum in $CDCl_3$, T=300K, δ in ppm (250 MHz): 1.50 and 1.90 (1H each, m, $CH_2$), between 2.20 and 2.50 (8H, m, $CH_2$ and $N(CH_3)_2$), 2.80 (2H, m, $NCH_2$), 3.40 (1H, m, NCH), 5.00 (1H, s, NH), 6.50 (1H, d, J=8 Hz, arom. CH), 7.20 (2H, m, 2 arom. CH)].

Dimethyl(6-trifluoromethylquinol-2-ylmethyl)amine may be prepared in the following manner: a solution, in 20 ml of ethanol, of 1.9 g of 2-chloromethyl-6-trifluoromethylquinoline and 27.8 ml of an ethanolic solution containing 36 g per liter of dimethylamine is stirred at a temperature close to 20° C. and for 72 hours. The reaction medium is concentrated under reduced pressure (4 kPa) at 40° C. The residue is taken up in 30 ml of a 0.25 N sodium hydroxide solution and then extracted twice with a total of 45 ml of ethyl acetate. The organic extracts are combined, dried over magnesium sulphate and concentrated to dryness under reduced pressure (4 kPa) at 40° C. The crude product is chromatographed on a silica gel column, eluting with a mixture of cyclohexane and ethyl acetate (50-50 by volume). 1.4 g of dimethyl(6-trifluoromethylquinol-2-ylmethyl)amine are thus obtained in the form of a brown oil [$^1$H NMR spectrum in CDCl$_3$, T=300K, δ in ppm ((250 MHz): 2.30 (6H, s, N(CH$_3$)$_2$), 3.70 (2H, s, NCH$_2$) 7.65 (1H, d, J=8 Hz, arom. CH), 7.80 (1H, dd, J=8 and 2 Hz, arom. CH), 8.05 (1H, s, arom. CH), 8.15 (2H, m, arom. CH)].

2-chloromethyl-6-trifluoromethylquinoline may be prepared in the following manner: a suspension of 52.75 g of 2-methyl-6-trifluoromethylquinoline, 33.2 g of N-chlorosuccinimide and 1.1 g of benzoyl peroxide in 500 ml of tetrachloromethane is heated to and kept for 24 hours at boiling temperature under argon. After cooling to around 20° C., the insoluble matter is removed by filtration, washed with 20 ml of tetrachloromethane and the combined filtrates are concentrated under reduced pressure (4 kPa) at 40° C. The crude product is chromatographed on a silica gel column, eluting with a mixture of cyclohexane and ethyl acetate (97.5-2.5 by volume). 24.1 g of 2-chloromethyl-6-trifluoromethylquinoline are thus obtained in the form of an orange-coloured solid melting at 66° C.

EXAMPLE 29

The procedure is carried out as in Example 28, but starting with 1.47 g of bromine in 4.7 ml of acetic acid, 2.05 g of potassium thiocyanate and 2.5 g of (R,S)-ethylmethyl(6-trifluoromethyl-1,2,3,4-tetrahydroquinol-2-ylmethyl)amine in 25 ml of acetic acid and allowing the reaction to proceed for 70 hours. The crude product is chromatographed on a silica gel column, eluting with a mixture of dichloromethane and methanol (98.75-1.25 by volume) to give an orange-coloured oil. The latter is redissolved in 30 ml of ethyl ether, decolorized by means of activated charcoal and then supplemented with a solution of hydrochloric isopropanol. 1.4 g of (R,S)-ethylmethyl(2-imino-8-trifluoromethyl-5,6-dihydro-2H,4H-thiazolo[5,4,3-ij]quinol-4-ylmethyl)amine dihydrochloric are obtained in the form of a cream-coloured solid melting at around 280° C. with decomposition [$^1$H NMR spectrum in DMSO-d$_6$, T=300K, δ in ppm (300 MHz): 1.30 (3H, t, J=6 Hz, CH$_3$) 2.20 and 2.75 (1H each, m, CH$_2$), 2.95 (3H, s, NCH$_3$), between 3.00 and 3.60 (6H, m, CH$_2$ and 2 NCH$_2$) 5.45 (1H, m, NCH), 7.85 (1H, s, arom. CH), 8.30 (1H, s, arom. CH)].

(R,S)-ethylmethyl(6-trifluoromethyl-1,2,3,4-tetrahydroquinol-2-ylmethyl)amine may be prepared by carrying out the procedure as in Example 28, but starting with 3.4 g of ethylmethyl(6-trifluoromethylquinol- 2-yl)amine, 3 times 0.52 g of nickel(II) chloride hexahydrate in 70 ml of methanol and 3 times 1.9 g of sodium tetrahydroborate, and then hydrolysing with 100 g of ice. The crude product is chromatographed on a silica gel column, eluting with a mixture of dichloromethane and methanol (97.5-2.5 by volume). 2.5 g of (R,S)-ethylmethyl(6-trifluoromethyl-1,2, 3,4-tetrahydroquinol-2-ylmethyl)amine are thus obtained in the form of an orange-coloured oil [$^1$H NMR spectrum in CDC13, T=300K, δ in ppm (300 MHz): 1.05 (3H, t, J=6 Hz, CH$_3$), 1.45 and 1.85 (1H each, m, CH$_2$), 2.25 (3H, s, NCH$_3$), between 2.25 and 2.90 (6H, m, CH$_2$ and 2 NCH$_2$), 3.40 (1H, m, NCH), 5.00 (1H, s, NH), 6.50 (1H, d, J=8 Hz, arom. CH), 7.15 (2H, m, 2 arom. CH)].

Ethylmethyl(6-trifluoromethylquinol-2-yl)amine may be prepared in the following manner: a solution of 3.5 g of 2-chloromethyl-6-trifluoromethylquinoline and 2.67 g of ethylmethylamine in 35 ml of ethanol is stirred for 24 hours under nitrogen and at a temperature close to 20° C. The reaction mixture is supplemented with 70 ml of distilled water, then extracted twice with a total of 105 ml of ethyl acetate and the combined organic extracts are dried over magnesium sulphate and concentrated to dryness under reduced pressure (4 kPa) at 40° C. The residue obtained is chromatographed on a silica gel column, eluting with a mixture of ethyl acetate and cyclohexane (75-25 by volume). 3.4 g of ethylmethyl (6-trifluoromethylquinol-2-yl)amine are thus obtained in the form of a brown oil [$^1$H NMR spectrum in CDCl$_3$, T=-300K, δ in ppm (250 MHz): 1.15 (3H, t, J=6 Hz, CH$_3$), 2.30 (3H, s, NCH$_3$), 2.55 (2H, q, J=6 Hz, NCH$_2$) 3.85 (2H, s, NCH$_2$), 7.75 (1H, d, J=8 Hz, arom. CH), 7.87 (1H, dd, J=8 and 2 Hz, arom. CH), 8.10 (1H, s, arom. OH), 8.20 (2H, m, 2 arom. CH)].

EXAMPLE 30

The process is carried out as in Example 28, but starting with 1.13 g of bromine in 3 ml of acetic acid, 1.6 g of potassium thiocyanate and 2.8 g of (R,S)-2-[4-(4-fluorophenyl)piperazin-1-ylmethyl]-6-trifluoromethyl-1,2, 3,4-tetrahydroquinoline in 13 ml of acetic acid. The crude product is chromatographed on a silica gel column, eluting with a mixture of dichloromethane and methanol (99-1 by volume). 1.4 g of (R,S)-4-[4-(4-fluorophenyl)piperazin-1-ylmethyl] -2-imino-8-trifluoromethyl-5,6-dihydro-2H,4H-thiazolo[5,4,3-ij]quinoline are obtained in the form of a yellow solid melting at 60° C. [Analysis C$_{22}$H$_{22}$F$_4$N$_4$S, % calculated C: 58.66,H: 4.92, F: 16.87, N: 12.44, S: 7.12, % found O: 58.70,H: 4.98, F: 16.61, N: 12.43, S: 6.88].

(R,S)-2-[4-(4-fluorophenyl)piperazin-1-ylmethyl]-6-trifluoromethyl-1,2,3,4-tetrahydroquinoline may be prepared by carrying out the procedure as in Example 28, but starting with 4.4 g of 2-[4-(4-fluorophenyl)piperazin-1-ylmethyl] -6-trifluoromethylquinoline, 9.4 g of nickel(II) chloride hexahydrate in 50 ml of methanol and 3.4 g of sodium tetrahydroborate. The crude product is chromatographed on a silica gel column, eluting with dichloromethane. 2.8 g of (R,S)-2-[4-(4-fluorophenyl)piperazin-1-ylmethyl]-6-trifluoromethyl-1,2,3,4-tetrahydroquinoline are thus obtained in the form of cream-coloured crystals melting at 157° C.

2-[4-(4-Fluorophenyl)piperazin-1-ylmethyl]-6-trifluoromethylquinoline may be prepared in the following manner: a solution of 3 g of 2-chloromethyl-6-trifluoromethylquinoline and 6.6 g of 1-(4-fluorophenyl) piperazine in 80 ml of ethanol is stirred for 70 hours at a temperature close to 20° C. The reaction mixture is concentrated to dryness under reduced pressure (4 kPa) at 40° C. The residue is treated with 50 ml of distilled water and 10 ml of aqueous ammonia at 32%, then extracted twice with a total of 150 ml of ethyl acetate. The combined organic extracts are dried over magnesium sulphate and concentrated to dryness under reduced pressure (4 kPa) at 40° C. The residue obtained is chromatographed on a silica gel column, eluting with a mixture of dichloromethane and methanol (98-2 by volume). 4.4 g of 2-[4-(4-fluorophenyl) piperazin-1-ylmethyl]-6-trifluoromethylquinoline are thus obtained in the form of a brown solid melting at 113° C.

EXAMPLE 31

The procedure is carried out as in Example 28, but starting with 0.85 g of bromine in 5 ml of acetic acid, 1.18 g of potassium thiocyanate and 1.5 g of (R,S)-2-(pyrrolidin-1-ylmethyl)-6-trifluoromethyl-1,2,3,4-tetrahydroquinoline in 16 ml of acetic acid. The crude product is chromatographed on a silica gel column, eluting with a mixture of dichloromethane and methanol (99-1 by volume) to give a yellow oil. The latter is redissolved in ethyl ether, decolorized by means of activated charcoal and then supplemented with a solution of hydrochloric isopropanol. 1.1 g of (R,S)-2-imino-4-(pyrrolidin-1-ylmethyl)-8-trifluoromethyl-5,6-dihydro-2H,4H-thiazolo[5,4,3-ij]quinoline dihydrochloride are obtained in the form of a cream-coloured solid melting at around 270° C. with decomposition [Analysis $C_{16}H_{20}Cl_2F_3N_3S$, % calculated C: 46.38, H: 4.87, Cl: 17.11, F: 13.76, N: 10.14, S: 7.74, % found C: 46.4, H: 4.6, Cl: 16.8, F: 13.6, N: 10.1, S: 8.1].

(R,S)-2-(pyrrolidin-1-ylmethyl)-6-trifluoromethyl-1,2,3,4-tetrahydroquinoline may be prepared by carrying out the procedure as in Example 28, but starting with 2.5 g of 2-(pyrrolidin-1-ylmethyl)-6-trifluoromethylquinoline, 3 times 0.74 g of nickel(II) chloride hexahydrate in 40 ml of methanol and 3 times 2.7 g of sodium tetrahydroborate. The crude product is chromatographed on a silica gel column, eluting with a mixture of dichloromethane and methanol (99-1 by volume). 1.6 g of (R,S)-2-(pyrrolidin-1-ylmethyl)-6-trifluoromethyl-1,2,3,4-tetrahydroquinoline are thus obtained in the form of a yellow oil [$^1$H NMR spectrum in DMSO-$d_6$, T=300K, δ in ppm (300 MHz): 1.50 and 1.95 (1H each, m, $CH_2$), 1.80 (4H, m, 2 $CH_2$), between 2.40 and 2.65 (6H, m, 3 $NCH_2$), 2.75 (2H, m, $CH_2$), 3.45 (1H, m, NCH), 6.20 (1H, s, NH), 6.70 (1H, d, J=8 Hz, arom. CH), 7.20 (2H, m, 2 arom. CH)].

2-(Pyrrolidin-1-ylmethyl)-6-trifluoromethylquinoline may be prepared by carrying out the procedure as in Example 29, but starting with 3 g of 2-chloromethyl-6-trifluoromethylquinoline and 2.6 g of pyrrolidine in 30 ml of ethanol. The crude product obtained is chromatographed on a silica gel column, eluting with a mixture of dichloromethane and methanol (99-1 by volume). 2.5 g of 2-(pyrrolidin-1-ylmethyl)-6-trifluoromethylquinoline are thus obtained in the form of an orange-coloured oil [$^1$H NMR spectrum in $CDCl_3$, T=300K, δ in ppm (300 MHz): 2.15 (4H, m, 2 $CH_2$), 3.30 (4H, m, 2 $NCH_2$), 4.50 (2H, s, $NCH_2$), 7.90 (1H, d, J=8 Hz, arom. CH), 8.15 (2H, m, 2 arom. CH), 8.25 (1H, d, J=8 Hz, arom. CH), 8.35 (1H, d, J=8 Hz, arom. CH)].

EXAMPLE 32

The procedure is carried out as in Example 28, but starting with 0.64 g of bromine in 3.7 ml of acetic acid, 0.89 g of potassium thiocyanate and 1.2 g of (R,S)-2-(morpholin-4-ylmethyl)-6-trifluoromethyl- 1,2,3,4-tetrahydroquinoline in 12 ml of acetic acid. The crude product is chromatographed on a silica gel column, eluting with a mixture of dichloromethane and methanol (99-1 by volume) to give a brown oil. The latter is redissolved in ethyl ether, decolorized by means of activated charcoal and then supplemented with a solution of hydrochloric isopropanol. 0.8 g of (R,S)-2-imino-4-(morpholin-4-ylmethyl)-8-trifluoromethyl-5,6-dihydro-2H,4H-thiazolo[5,4,3-ij]quinoline dihydrochloride is obtained in the form of a cream-coloured solid melting at around 263° C. with decomposition [Analysis $C_{16}H_{20}Cl_2F_3N_3OS$, % calculated C: 44.66, H: 4.68, Cl: 16.48, F: 13.24, N: 9.76, O: 3.72, S: 7.45, % found C: 45.1, H: 4.8, Cl: 15.9, F: 12.9, N: 9.7, S: 7.1].

(R,S)-2-Morpholin-4-ylmethyl)-6-trifluoromethyl-1,2,3,4-tetrahydroquinoline may be prepared by carrying out the procedure as in Example 28, but starting with 3.5 g of 2-(morpholin-4-ylmethyl)-6-trifluoromethylquinoline, 0.98 g of nickel(II) chloride hexahydrate in 50 ml of methanol and 3.6 g of sodium tetrahydroborate. The crude product is chromatographed on a silica gel column, eluting with a mixture of dichloromethane and methanol (99-1 by volume). 0.8 g of (R,S)-2-(morpholin-4-ylmethyl)-6-trifluoromethyl-1,2,3,4-tetrahydroquinoline is thus obtained in the form of a brown oil [$^1$H NMR spectrum in DMSO-$d_{61}$ T=300K, δ in ppm (300 MHz): 1.50 and 1.90 (1H each, m, $CH_2$), between 2.30 and 2.50 (6H, m, 3 $NCH_2$), 2.70 (2H, m, $CH_2$), 3.50 (1H, m, NCH), 3.65 (4H, m, 2 $OCH_2$), 6.10 (1H, s, NH), 6.65 (1H, d, J=8 Hz, arom. CH), 7.15 (2H, m, 2 arom. CH)].

2-(Morpholin-4-ylmethyl)-6-trifluoromethylquinoline may be prepared by carrying out the procedure as in Example 29, but starting with 3 g of 2-chloromethyl-6-trifluoromethylquinoline and 3.18 g of morpholine in 30 ml of ethanol. The crude product obtained is chromatographed on a silica gel column, eluting with a mixture of dichloromethane and methanol (97.5-2.5 by volume). 3.5 g of 2-(morpholin-4-yl-methyl)-6-trifluoromethylquinoline are thus obtained in the form of an orange-coloured oil [$^1$H NMR spectrum in $CDCl_3$, T=300K, δ in ppm (300 MHz): 2.55 (4H, m, 2 $NCH_2$) 3.75 (4H, m, 2 $OCH_2$), 3.85 (2H, s, $NCH_2$), 7.75 (1H, d, J=8 Hz, arom. CH), 7.85 (1H, dd, J=8 and 2 Hz, arom. CH), between 8.10 and 8.25 (3H, m, arom. CH)].

EXAMPLE 33

A solution of 0.3 g of (R,S)-2-ethylsulphonylmethyl-8-thiocyanato-6-trifluoromethyl-1,2,3,4-tetrahydroquinoline in 10 ml of ethanol is heated to and kept for 74 hours at boiling temperature. The reaction medium is concentrated under reduced pressure (4 kPa) at 40° C. The residue is chromatographed on a silica gel column, eluting with dichloromethane to give a yellow foam. The latter is redissolved in 20 ml of dichloromethane and the solution is decolorized by means of activated charcoal and then concentrated under vacuum. 0.2 g of (R,S)-4-ethylsulphonylmethyl-2-imino-8-trifluoromethyl-5,6-dihydro-2H,4H-thiazolo[5,4,3-ij]quinoline is obtained in the form of a yellowish foam melting at 140° C. [Analysis $C_{14}H_{15}F_3N_2O_2S_2$, % calculated C: 46.14, H: 4.15, F: 15.64, N: 7.69, O: 8.78, S: 17.60, % found C: 46.00, H: 3.84, F: 15.20, N: 7.51, S: 17.71].

(R,S)-2-ethylsulphonylmethyl-8-thiocyanato-6-trifluoromethyl-1,2,3,4-tetrahydroquinoline may be prepared in the following manner: 0.208 g of bromine diluted in 0.65 ml of acetic acid is added dropwise, at a temperature close to 20° C. and under argon, to a solution of 0.29 g of potassium thiocyanate and 0.4 g of (R,S)-2-ethylsulphonylmethyl-6-trifluoromethyl-1,2,3,4-tetrahydroquinoline in 4 ml of acetic acid. The reaction mixture is stirred for 18 hours at the same temperature, poured over ice and alkalinized with a solution of aqueous ammonia at 32%. The insoluble matter is removed by filtration, and the filtrate is extracted twice with a total of 75 ml of ethyl acetate. The organic extracts are combined, dried over magnesium sulphate and concentrated to dryness under reduced pressure (4 kPa) at 40° C. The crude product is chromatographed on a silica gel column, eluting with dichloromethane. 0.2 g of (R,S)-2-ethylsulphonylmethyl-8-thiocyanato-6-trifluoromethyl-1,2,3,4-tetrahydroquinoline is obtained in the form of pale yellow crystals melting at 137° C. (R,S)-2-ethylsulphonylmethyl-6-trifluoromethyl-1,2,3,4-tetrahydroquinoline may be prepared in the following manner: 1.3 g of 2-ethylsulphonylmethyl-6- trifluoromethylquinoline 1-oxide with 0.22 g of platinum oxide in 14 ml of a methanol-tetrahydrofuran mixture (50-50 by volume) are hydrogenated at a temperature close to 20° C. at a pressure of 5 bar for 1.5 hours. After filtration of the reaction medium, the organic phase is concentrated under reduced pressure (4 kPa) at 40° C. The crude product is first chromatographed on a silica gel column, eluting with a mixture of dichloromethane and methanol (98.75-1.25 by volume), and then on a silica gel column, eluting with dichloromethane. 0.7 g of (R,S)-2-ethylsulphonylmethyl-6-trifluoromethyl-1,2,3,4-tetrahydroquinoline is thus obtained in the form of yellow crystals melting at 85° C.

2-Ethylsulphonylmethyl-6-trifluoromethylquinoline 1-oxide may be prepared in the following manner: 6.2 g of 3-chloroperbenzoic acid (80% purity) are added in small portions to a solution, under argon and cooled to 5° C., of 2 g of 2-ethylsulphanylmethyl-6-trifluoromethylquinoline in 80 ml of dichloromethane, and the mixture is kept stirred for 16 hours at a temperature close to 20° C. 100 ml of a saturated aqueous sodium hydrogen carbonate solution as well as 30 ml of dichloromethane are then added and the stirring is continued until the evolution of gas ceases. After separation of the two phases, the aqueous phase is extracted with 50 ml of dichloromethane and the combined organic extracts are dried over magnesium sulphate and concentrated to dryness under reduced pressure (4 kPa) at 20° C. The solid obtained is chromatographed on a silica gel column, eluting with a mixture of dichloromethane and methanol (97.5-2.5 by volume). 1.3 g of 2-ethylsulphonylmethyl-6-trifluoromethylquinoline 1-oxide are thus obtained in the form of yellow crystals melting at 166° C.

2-Ethylsulphanylmethyl-6-trifluoromethylquinoline may be prepared in the following manner: a solution of 1.9 g of ethanethiol in 20 ml of dimethylformamide is added over 20 minutes to a suspension in 5 ml of dimethylformamide, under argon and cooled to 5° C., of 1.2 g of a 60% dispersion of sodium hydride in mineral oil. The reaction medium is then stirred for 1 hour at around 20° C. and then, after cooling to around 5° C., is supplemented over 1 hour with a solution of 6.7 g of 2-chloromethyl-6-trifluoromethylquinoline in 50 ml of dimethylformamide. The mixture is stirred for 16 hours at around 20° C. and then hydrolysed at around 5° C. with 100 ml of distilled water. It is then extracted twice with a total of 75 ml of ethyl acetate and the combined organic extracts are dried over magnesium sulphate and concentrated to dryness under reduced pressure (4 kPa) at 40° C. The residue obtained is chromatographed on a silica gel column, eluting with dichloromethane. 5.6 g of 2-ethylsulphanylmethyl-6-trifluoromethylquinoline are thus obtained in the form of a brown oil [$^1$H NMR spectrum in CDCl$_3$, T=300K, δ in ppm (250 MHz): 1.20 (3H, t, J=6 Hz, CH$_3$), 2.48 (2H, q, J=6 Hz, SCH$_2$), 4.00 (2H, s, SCH$_2$), 7.65 (1H, d, J=BHz, arom. CH), 7.85 (1H, dd, J=8 and 2 Hz, arom. CH), 8.10 (2H, m, 2 arom. CH), 8.20 (1H, d, J=8 Hz, arom. CH)].

EXAMPLE 34

A solution of 0.40 g of bromine in 1 ml of acetic acid is poured dropwise, over 2 minutes, over a suspension of 0.79 g of potassium selenocyanate in 10 ml of acetic acid. After stirring for 1 hour at about 20° C., a solution of 0.5 g of 6-trifluoromethyl-1,2,3,4-tetrahydroquinoline is poured into 1 ml of acetic acid and the mixture is stirred for 3 hours at about 20° C. The reaction medium is then poured over a mixture of 20 g of ice and 20 ml of distilled water. An insoluble matter is removed by filtration, the filtrate is alkalinized with 15 ml of an aqueous solution of aqueous ammonia at 280% and extracted three times with 50 ml of dichloromethane. The combined organic extracts are washed with 50 ml of distilled water, dried over magnesium sulphate, filtered and concentrated to dryness under reduced pressure (2 kPa). 0.25 g of the product obtained (out of 0.34 g) is suspended in a total of 7.5 ml of ethyl ether to which 1 ml of about 3.8 M hydrochloric ether is added dropwise. After stirring for 10 minutes at about 20° C., the product is separated by filtration, washed with twice 2.5 ml of ethyl ether and air-dried. 0.25 g of 2-imino-8-trifluoromethyl-5,6-dihydro-2H,4H-selenazolo[5,4,3-ij]quinoline hydrochloride is thus obtained in the form of a yellow solid melting at 172° C. [Analysis C$_{11}$H$_{10}$ClF$_3$N$_2$Se, % calculated C: 38.67, H: 2.95, Cl: 10.38, F: 16.68, N: 8.20, % found C: 37.82, H: 3.00, Cl: 10.47, F: 14.77, N: 7.72, H$_2$O: 3.6].

EXAMPLE 35

A mixture of 1 g of (R,S)-4-[4-(4-fluorophenyl)piperazin-1-ylmethyl]-2-trifluoromethylcarbonylimino-8-trifluoromethoxy-5,6-dihydro-4H-thiazolo[5,4,3-ij]quinoline, 10 ml of a 10 aqueous potassium carbonate solution, 10 ml of acetone and 10 ml of methanol is stirred for 7 hours at a temperature close to 20° C. The mixture is hydrolysed with 50 ml of distilled water and extracted twice with 50 ml and 25 ml of ethyl acetate. The combined organic extracts are dried over magnesium sulphate, filtered and concentrated to dryness under reduced pressure (2 kPa). The residue obtained is purified by chromatography on a silica gel column, eluting with a mixture of dichloromethane and methanol (98.75-1.25 by volume). 0.7 g of (R,S)-4-[4-(4-fluorophenyl)piperazin-1-ylmethyl]-2-imino-8-trifluoromethoxy-5,6-dihydro-2H,4H-thiazolo[5,4,3-ij] quinoline is thus obtained in the form of a cream-coloured solid melting at 52° C. [Analysis C$_{22}$H$_{22}$F$_4$N$_4$OS, % calculated C: 56.64, H: 4.75, F: 16.29, N: 12.01, O: 3.43, S: 6.87, % found C: 56.7, H: 4.8, F: 16.1, N: 11.9, S: 6.8].

(R,S)-4-[4-(4-Fluorophenyl)piperazin-1-ylmethyl]-2-trifluoromethylcarbonylimino-8-trifluoromethoxy-5,6-dihydro-4H-thiazolo[5,4,3-ij]quinoline may be prepared in the following manner: a solution of 0.36 g of 1-(4-fluorophenyl)piperazine in 3.6 ml of anhydrous dichloromethane is added dropwise to a solution of 0.54 g of (R,S)-2-trifluoromethylcarbonylimino-4-trifluoromethylsulphomethyl-8-trifluoromethoxy-5,6-dihydro-4H-thiazolo[5,4,3-ij]quinoline in 10 ml of dichloromethane, kept under argon and at about 0° C. The mixture is stirred for 15 minutes at a temperature close to 0° C. and then the temperature is allowed to gradually return to a temperature close to 20° C., keeping the mixture thus stirred for 16 hours. The medium is hydrolysed with 20 ml of distilled water, separated after settling out and the aqueous phase is extracted once with 15 ml of dichloromethane. The combined organic extracts are dried over magnesium sulphate, concentrated to dryness under reduced pressure (2 kPa). The residue obtained is purified by chromatography on a silica gel column, eluting with dichloromethane. 0.2 g of (R,S)-4-[4-(4-fluorophenyl)piperazin-1-ylmethyl]-2-trifluoromethylcarbonylimino-8-trifluoromethoxy-5,6-dihydro-4H-thiazolo[5,4,3-ij]quinoline is thus obtained in the form of a cream-coloured solid melting at 163° C.

(R,S)-2-Trifluoromethylcarbonylimino-4-trifluoromethylsulphomethyl-8-trifluoromethoxy-5,6-dihydro-4H-thiazolo[5,4,3-ij]quinoline may be prepared in the following manner: a suspension of 0.304 g of (R,S)-2-trifluoromethylcarbonylimino-8-trifluoromethoxy-5,6-dihydro-4H-thiazolo[5,4,3-ij]-quinoline-4-methanol in 2.5 ml of dichloromethane and then a solution of 0.35 g of triflic anhydride in 2 ml of dichloromethane is poured dropwise over a solution, kept at −15° C. under argon, of 2.5 ml of dichloromethane and 0.1 g of pyridine. The mixture is kept stirred at −15° C. for 15 minutes and then gradually brought to a temperature close to 0° C. where it is thus kept for 2 hours. The insoluble matter is removed by filtration on a bed of celite 545 and magnesium sulphate, washed with 2.5 ml of dichloromethane and the filtrate thus obtained of (R,S)-2-trifluoromethylcarbonylimino-4-trifluoromethylsulphomethyl-8-trifluoromethoxy-5,6-dihydro-4H-thiazolo[5,4,3-ij]quinoline is directly reacted in the next step.

(R,S)-2-Trifluoromethylcarbonylimino-8-trifluoromethoxy-5,6-dihydro-4H-thiazolo[5,4,3-ij]quinoline-4-methanol may be prepared in the following manner: 1.26 g of trifluoroacetic anhydride are poured dropwise over a suspension of 0.6 g of (R,S)-2-imino-8-trifluoromethoxy-5,6-dihydro-2H,4H-thiazolo[5,4,3-ij]quinoline-4-methanol in 12 ml of anhydrous dichloromethane, kept under argon and at a temperature close to 20° C., and the stirring is continued for 5 hours at the same temperature. The medium is then neutralized with 1.5 ml of triethylamine and then hydrolysed with 25 ml of distilled water at a temperature close to 20° C. The aqueous phase is extracted with 20 ml of dichloromethane and the combined organic extracts are dried over magnesium sulphate and concentrated to dryness under reduced pressure (2 kPa). The residue obtained is purified by chromatography on a silica gel column, eluting with a mixture of dichloromethane and methanol (99-1 by volume). 0.7 g of (R,S)-2-trifluoromethylcarbonylimino-8-trifluoromethoxy-5,6-dihydro-4H-thiazolo[5,4,3-ij]quinoline-4-methanol is thus obtained in the form of a cream-coloured solid melting at 156° C.

EXAMPLE 36

The procedure is carried out as in Example 23, but starting with 1.24 g of bromine diluted in 0.4 ml of acetic acid, 1.73 g of potassium thiocyanate and 1.8 g of (R,S)-6-trifluoromethyl-1,2,3,4-tetrahydroquinoline-3-methanol in 22 ml of acetic acid. The product obtained is purified by chromatography on a silica gel column, eluting with a mixture of dichloromethane and methanol (97.5-2.5 by volume). 0.8 g of (R,S)-2-imino-8-trifluoromethyl-5,6-dihydro-2H,4H-thiazolo[5,4,3-ij]quinoline-5-methanol is thus obtained in the form of a cream-coloured solid melting at 177° C. [Analysis $C_{12}H_{11}F_3N_2OS$, % calculated C: 50.0, H: 3.85, F: 19.77, N: 9.72, O: 5.55, S: 11.12, % found C: 49.67, H: 3.49].

(R,S)-6-Trifluoromethyl-1,2,3,4-tetrahydroquinoline-3-methanol may be prepared in the following manner: a solution of 2.73 g of ethyl 6-trifluoromethyl-1,2,3,4-tetrahydroquinoline-3-carboxylate in 27 ml of anhydrous tetrahydrofuran is poured dropwise over a suspension, kept under argon and at about 0° C., of 0.38 g of lithium tetrahydroaluminate in 3.8 ml of anhydrous tetrahydrofuran. The mixture is stirred for 1 hour 30 minutes at around 5° C. and then for 16 hours at a temperature close to 20° C. The reaction medium is then cooled to 5° C. and then slowly hydrolysed with 30 ml of distilled water, and the product is extracted twice with 50 ml and then 25 ml of ethyl acetate. The combined organic extracts are dried over magnesium sulphate, filtered and concentrated to dryness under reduced pressure (2 kPa). The product obtained (2.2 g) is purified by chromatography on a silica gel column, eluting with a mixture of dichloromethane and methanol (97.5-2.5 by volume). 1.8 g of (R,S)-6-trifluoromethyl-1,2,3,4-tetrahydroquinoline-3-methanol are thus obtained in the form of a yellow oil [$^1$H NMR spectrum in $CDCl_3$, T=300K, δ in ppm (250 MHz): 1.70 (1H, s, NH), 2.20 (1H, m, CH), 2.55 and 2.85 (1H each, respectively dd, J=16 and 8 Hz, and dd, J=16 and 4 Hz, $CH_2$ aryl), 3.18 and 3.50 (1H each, respectively dd, J=10 and 8 Hz, and dd, J=10 and 2 Hz, $NCH_2$), 3.65 (2H, m, $OCH_2$), 4.20 (1H, s, OH), 6.50 (1H, d, J=8 Hz, arom. CH), 7.20 (2H, m, 2 arom. CH)].

Ethyl 6-trifluoromethyl-1,2,3,4-tetrahydroquinoline-3-carboxylate may be prepared in the following manner: 30 g of ethyl 4-chloro-6-trifluoromethylquinoline-3-carboxylate with 2.1 g of 101 palladium on carbon in 300 ml of acetic acid are hydrogenated at a temperature close to 20° C. and at a pressure of 5 bar for 16 hours. The reaction medium is poured over 400 g of ice and alkalinized with an aqueous solution of aqueous ammonia at 28% up to a pH of 11. The product is extracted with 500 ml of ethyl acetate and the organic extract is filtered on a clarcel bed which is washed with water. The aqueous phase of the filtrate is extracted with 250 ml of ethyl acetate and the combined organic extracts are dried over magnesium sulphate, filtered and concentrated to dryness under reduced pressure (2 kPa). The residue obtained is purified by chromatography on a silica gel column, eluting with dichloromethane. 3.1 g of ethyl 6-trifluoromethyl-1,2,3,4-tetrahydroquinoline-3-carboxylate are thus obtained in the form of fluorescent yellow crystals melting at 69° C.

Ethyl 4-chloro-6-trifluoromethylquinoline-3-carboxylate may be prepared according to C. J. Matson et al., J. Med. Chem., 22, (7), 816–823 (1979).

EXAMPLE 37

The procedure is carried out as in Example 23, but starting with 1.1 g of bromine in 3.5 ml of acetic acid, 1.6 g of 7-trifluoromethoxy-3,4-dihydro-1H-quinoxalin-2-one and 1.54 g of potassium thiocyanate in 20 ml of acetic acid. The product obtained (1.8 g) is purified by chromatography on a silica gel column, eluting with a mixture of dichloromethane and methanol (99-1 by volume). 0.3 g of 2-imino-8-trifluoromethoxy-2H,4H-thiazolo[3,4,5-de]quinoxalin-5(6H)-one is thus obtained in the form of a yellow solid melting at 255° C. [Analysis $C_{10}H_6F_3N_3O_2S$, % calculated C: 41.53, H: 2.09, F: 19.71, N: 14.53, O: 11.06, S: 11.09, % found C: 41.00, H: 1.7, F: 19.2, N: 14.50, S: 11.6].

7-Trifluoromethoxy-3,4-dihydro-1H-quinoxalin-2-one may be prepared in the following manner: 3 ml of 36% hydrochloric acid are poured dropwise, at a temperature close to 20° C., over a suspension of 0.92 g of ethyl N-(2-nitro-4-trifluoromethoxyphenyl)glycinate, 1.36 g of granular tin in 2.3 ml of ethanol. The reaction medium is then heated for 2 hours under reflux and then, after returning to a temperature close to 20° C., diluted with 6 ml of distilled water and neutralized with solid sodium carbonate. The product is extracted with 40 ml of ethyl acetate and then the whole is filtered on a clarcel bed and washed with 10 ml of ethyl acetate. The aqueous phase of the filtrate is then extracted with 10 ml of ethyl acetate and the combined organic extracts are dried over magnesium sulphate, filtered and concentrated to dryness under reduced pressure (2 kPa). The product obtained (0.7 g) is purified by chromatography on a silica gel column, eluting with a mixture of cyclohexane and ethyl acetate (75-25 by volume). 0.3 g of 7-trifluoromethoxy-3,4-dihydro-1H-quinoxalin-2-one is thus obtained in the form of a light-yellow solid melting at 140° C.

Ethyl N-(2-nitro-4-trifluoromethoxyphenyl)glycinate may be prepared in the following manner: there are added to 17.3 g of 95-sulphuric acid, kept at 5° C., 4.7 g of ethyl N-(4-trifluoromethoxyphenyl)-N-tosylglycinate over which a solution of 1.12 g of 9406 nitric acid in 2 ml of 95% sulphuric acid is poured dropwise while the temperature is kept between 50 and 10° C. The mixture is stirred for 1 hour at 10° C. and then stirred for 16 hours at a temperature close to 20° C. The reaction medium is hydrolysed with 50 g of ice and extracted twice with 50 ml and 25 ml of ethyl acetate. The combined organic extracts are dried over magnesium sulphate, filtered and concentrated to dryness under reduced pressure (2 kPa). The product obtained is purified by chromatography on a silica gel column, eluting with a mixture of cyclohexane and ethyl acetate (95-5 by volume). 0.9 g of ethyl N-(2-nitro-4-trifluoromethoxyphenyl) glycinate is thus obtained in the form of an orange-coloured solid melting at 94° C.

Ethyl N-(4-trifluoromethoxyphenyl)-N-tosylglycinate may be prepared in the following manner: a solution of 3.31 g of N-tosyl-4-trifluoromethoxyaniline in 33 ml of anhydrous tetrahydrofuran is poured dropwise over a suspension of 0.44 g of sodium hydride (at 60% in liquid paraffin) in 5 ml of anhydrous tetrahydrofuran, kept under argon, and then the medium is diluted with 30 ml of anhydrous tetrahydrofuran. After stirring for 1 hour at a temperature close to 20° C., a solution of 1.84 g of ethyl bromoacetate in 12 ml of anhydrous tetrahydrofuran is poured in and the mixture is stirred for 16 hours at a temperature close to 20° C. The medium is hydrolysed with 50 ml of distilled water and extracted twice with 50 ml and 25 ml of ethyl acetate. The combined organic extracts are dried over magnesium sulphate, filtered and concentrated to dryness under reduced pressure (2 kPa). The product obtained is purified by chromatography on a silica gel column, eluting with a mixture of cyclohexane and ethyl acetate (87.5-12.5 by volume). 3.7 g of ethyl N-(4-trifluoromethoxyphenyl)-N-tosylglycinate are thus obtained in the form of a yellow oil [$^1$H NMR spectrum in CDCl$_3$, T=300K, δ in ppm (300 MHz): 1.15 (3H, t, J=6 Hz, CH$_3$), 2.35 (3H, s, CH$_3$Ph), 4.10 (2H, q, J=6 Hz, OCH$_2$) 4.30 (2H, s, NCH$_2$CO), 7.08 (2H, d, J=7 Hz, arom. CH), 7.20 (4H, m, 4 arom. CH), 7.50 (2H, d, J=7 Hz, arom. CH)].

N-Tosyl-4-trifluoromethoxyaniline may be prepared in the following manner: 32.2 g of p-toluenesulphonyl chloride are added in small fractions to a solution of 30 g of 4-trifluoromethoxyaniline in 170 ml of pyridine, kept under argon at a temperature close to 20° C., and the mixture thus obtained is stirred for 16 hours at the same temperature. The reaction medium is hydrolysed with 250 ml of distilled water and extracted twice with 250 ml and 125 ml of ethyl acetate. The combined organic extracts are dried over magnesium sulphate, filtered and concentrated to dryness under reduced pressure (2 kPa). The residue obtained is taken up twice in 200 ml of toluene and concentrated each time under reduced pressure and then taken up in 100 ml of isopropyl ether. The solid is separated by filtration, washed with twice 50 ml of isopropyl ether and dried under reduced pressure. 45 g of N-tosyl-4-trifluoromethoxyaniline are thus obtained in the form of a white solid melting at 115° C.

EXAMPLE 38

A solution of 0.25 g of bromine in 2 ml of acetic acid is poured dropwise into a solution, kept under argon and at around 17° C., of 0.42 g of potassium thiocyanate in 5 ml of acetic acid and the suspension obtained is stirred for 10 minutes before adding thereto a solution of 0.4 g of 4-ethylsulphinyl-6-trifluoromethyl-1,2,3,4-tetrahydroquinoline in 1 ml of acetic acid. The reaction mixture is stirred for 16 hours at a temperature close to 20° C. and then poured over a cold aqueous solution of aqueous ammonia and ethyl acetate. The organic extract separated is washed with distilled water, then with a saturated aqueous sodium chloride solution, dried over magnesium sulphate, filtered and concentrated to dryness under reduced pressure (2 kPa). The product obtained (0.35 g) is dissolved in ethyl acetate and then 0.55 ml of about 1.94 M methanesulphonic acid in isopropanol is added. The precipitate is separated by filtration, washed with ethyl acetate and dried under reduced pressure at a temperature of 50° C. 0.3 g of 2-imino-6-ethylsulphinyl-8-trifluoromethyl-5,6-dihydro-2H,4H-thiazolo[5,4,3-ij]quinoline methanesulphonate is thus obtained in the form of a cream-coloured solid melting at 220° C. with decomposition [Analysis C$_{14}$H$_{17}$F$_3$N$_2$O$_4$S$_3$, % calculated C: 39.06,H: 3.98, F: 13.24, N: 6.51, O: 14.87, S: 22.34,% found C: 38.37,H: 4.21, F: 12.27, N: 6.48, S: 22.22].

4-Ethylsulphinyl-6-trifluoromethyl-1,2,3,4-tetrahydroquinoline may be prepared in the following manner: 25 g of silica, previously dried at 50° C. under reduced pressure for 2 hours, are added to a solution of 2 g of tert-butyl 4-ethylsulphinyl-6-trifluoromethyl-1,2,3,4-tetrahydroquinoline-1-carboxylate in 25 ml of dichloromethane. The mixture is concentrated to dryness under reduced pressure and the residue obtained is kept at 50° C. under reduced pressure for 72 hours. After returning to a temperature close to 20° C., the silica is taken up in tetrahydrofuran and separated by filtration. The filtrate is concentrated to dryness under reduced pressure and the residue obtained is purified by chromatography on a silica gel column, eluting with ethyl acetate. 0.45 g of 4-ethylsulphinyl-6-trifluoromethyl-1,2,3,4-tetrahydroquinoline is obtained in the form of a yellow oil which is used as it is.

tert-Butyl 4-ethylsulphinyl-6-trifluoromethyl-1,2,3,4-tetrahydroquinoline-1-carboxylate may be prepared in the following manner: 3.2 g of 3-chloroperbenzoic acid (80% purity) are added in several portions to a solution, kept at around 5° C., of 4.9 g of tert-butyl 4-ethylthio-6-trifluoromethyl-1,2,3,4-tetrahydroquinoline-1-carboxylate in 50 ml of dichloromethane. The reaction medium is stirred for 20 hours at a temperature close to 20° C. and then the insoluble matter is removed by filtration and washed with dichloromethane. The organic filtrate is washed with a saturated aqueous sodium hydrogen carbonate solution, then distilled water and dried over magnesium sulphate before being concentrated to dryness under reduced pressure (2 kPa). The residue obtained (5.11 g) is purified by chromatography on a silica gel column, eluting with dichloromethane and then a mixture of dichloromethane and ethyl acetate (80-20 by volume). 2.9 g of tert-butyl 4-ethylsulphinyl-6-trifluoromethyl- 1,2,3,4-tetrahydroquinoline-1-carboxylate are thus obtained in the form of a yellow oil [$^1$H NMR spectrum of the 60/40 mixture of the diastereoisomers: Predominant isomer: spectrum in DMSO-d$_6$, T=300K, δ in ppm (400 MHz): 1.25 (3H, t, J=6 Hz, CH$_3$), 1.52 (9H, s, (CH$_3$)$_3$), between 2.15 and 2.90 (4H, m, SCH$_2$ and CH$_2$), 3.60 and 4.00 (1H each, m, NCH$_2$), 4.40 (1H, t, J=5 Hz, SCH), between 7.60 and 8.00 (3H, m, 3 arom. CH). Minor isomer: spectrum in DMSO-d$_6$, T=300K, δ in ppm (400 MHz): 1.27 (3H, t, J=6 Hz, CH$_3$), 1.52 (9H, s, (CH$_3$)$_3$), between 2.20 and 3.05 (4H, m, SCH$_2$ and CH$_2$), 3.70 and 3.85 (1H each, m, NCH$_2$), 4.33 (1H, t, J=5 Hz, SCH), between 7.55 and 8.00 (3H, m, 3 arom. CH)].

tert-Butyl 4-ethylthio-6-trifluoromethyl-1,2,3,4-tetrahydroquinoline-1-carboxylate may be prepared in the following manner: a solution of 1 g of ethanethiol in 5 ml of dimethylformamide is poured dropwise over a suspension, kept under argon and at a temperature close to 0° C., of 0.64 g of sodium hydride (60% purity in liquid paraffin) in 35 ml of anhydrous dimethylformamide. After stirring for 10 minutes at around 0° C., a solution of 6 g of tert-butyl 4-bromo-6-trifluoromethyl-1,2,3,4-tetrahydroquinoline-1-carboxylate in 10 ml of dimethylformamide is poured in and the mixture is kept stirred for 16 hours at a temperature close to 20° C. The medium is hydrolysed with 100 ml of distilled water and extracted with 100 ml of ethyl acetate. The organic extract is washed three times with 50 ml of distilled water and then with a saturated aqueous sodium hydrogen carbonate solution, dried over magnesium sulphate, filtered and concentrated to dryness under reduced pressure (2 kPa). 5.65 g of tert-butyl 4-ethylthio-6-trifluoromethyl-1,2,3,4-tetrahydroquinoline-1-carboxylate are obtained in the form of a colourless oil [$^1$H NMR spectrum in DMSO-d$_6$, T=300K, δ in ppm (250 MHz): 1.25 (3H, t, J=6 Hz, CH$_3$), 1.52 (9H, s, (CH$_3$)$_3$), 2.15 (2H, m, CH$_2$), 2.65 (2H, m, SCH$_2$), 3.75 and 3.95 (1H each, m, NCH$_2$), 4.37 (1H, t, J=5 Hz, SCH), 7.55 (1H, d, J=8 Hz, arom. CH), 7.70 (1H, s, arom. CH), 7.95 (1H, d, J=8 Hz, arom. CH)].

EXAMPLE 39

A solution of 0.59 g of bromine in 2 ml of acetic acid is poured dropwise into a solution, kept under argon and at around 17° C., of 0.525 g of potassium thiocyanate in 5 ml of acetic acid and the suspension obtained is stirred for 10 minutes before adding thereto a solution of 0.55 g of (R,S)-4-ethylsulphonyl-6-trifluoromethyl-1,2,3,4-tetrahydroquinoline in 1 ml of acetic acid. The reaction mixture is stirred for 16 hours at a temperature close to 20° C. and then poured over a cold aqueous solution of aqueous ammonia. The mixture is extracted with ethyl acetate and dichloromethane. The organic extracts are washed with distilled water, dried over magnesium sulphate, filtered and concentrated to dryness under reduced pressure (2 kPa). The residue obtained is purified by chromatography on a silica gel column, eluting with a mixture of ethyl acetate and petroleum ether (60-40 by volume). 0.32 g of (R,S)-2-imino-6-ethylsulphonyl-8-trifluoromethyl-5,6-dihydro-2H,4H-thiazolo[5,4,3-ij]quinoline is thus obtained in the form of a beige solid melting at 186° C. [Analysis C$_{13}$H$_{13}$F$_3$N$_2$O$_2$S$_2$, % calculated C: 44.56,H: 3.74, F: 16.27, N: 8.00, O: 9.13, S: 18.3, % found C: 45.01,H: 4.05, N: 7.58, S: 17.21].

(R,S)-4-Ethylsulphonyl-6-trifluoromethyl-1,2,3,4-tetrahydroquinoline may be prepared in the following manner: a solution of 1.9 g of tert-butyl (R,S)-4-ethylsulphonyl-6-trifluoromethyl-1,2,3,4-tetrahydroquinoline-1-carboxylate in 20 ml of dichloromethane, and 7.4 g of trifluoroacetic acid is stirred, at a temperature close to 20° C., for 4 hours. The mixture is concentrated to dryness under reduced pressure and the residue obtained is taken up in ethyl acetate. The organic phase is washed with a saturated aqueous sodium hydrogen carbonate solution, three times with 20 ml of distilled water and then with a saturated sodium chloride solution, dried over magnesium sulphate, filtered and concentrated to dryness under reduced pressure (2 kPa). The residue obtained is purified by chromatography on a silica gel column, eluting with a mixture of dichloromethane and ethyl acetate (95-5 by volume). 0.57 g of (R,S)-4-ethylsulphonyl-6-trifluoromethyl-1,2,3,4-tetrahydroquinoline is obtained in the form of a white solid melting at 150° C.

tert-Butyl (R,S)-4-ethylsulphonyl-6-trifluoromethyl-1,2,3,4-tetrahydroquinoline-1-carboxylate may be prepared in the following manner: 7.8 g of 3-chloroperbenzoic acid (80% purity) are added in several portions to a solution, kept at around 5° C., of 3.3 g of tert-butyl (R,S)-4-ethylthio-6-trifluoromethyl-1,2,3,4-tetrahydroquinoline-1-carboxylate in 40 ml of dichloromethane. The reaction medium is stirred for 20 hours at a temperature close to 20° C. and then neutralized with 45 ml of a saturated aqueous sodium hydrogen carbonate solution. The organic extract is washed with distilled water and dried over magnesium sulphate before being concentrated to dryness under reduced pressure (2 kPa). The residue obtained (4.83 g) is taken up in ethyl ether, left for 16 hours at a temperature close to 0° C. and the product is separated by filtration, washed with ethyl ether and dried under reduced pressure. 1.8 g of tert-butyl (R,S)-4-ethylsulphonyl-6-trifluoromethyl-1,2,3,4-tetrahydroquinoline-1-carboxylate are thus obtained in the form of a white solid melting at 110° C.

EXAMPLE 40

The procedure is carried out as in Example 1, but starting with 0.98 g of bromine diluted in 4 ml of acetic acid, 1.8 g of potassium thiocyanate and 1.5 g of (R,S)-4-dimethylamino-6-trifluoromethyl-1,2,3,4-tetrahydroquinoline in 18 ml of acetic acid. 2 g of a yellow oil are thus obtained, which oil is chromatographed on a silica gel column, eluting with a mixture of ethyl acetate and petroleum ether (80-20 by volume) and then with pure ethyl acetate. The yellow oil obtained (0.5 g) is taken up in 5 ml of ethyl acetate, to which 1.5 ml of a 1.94 N solution of methanesulphonic acid in isopropanol are added. The precipitate obtained, triturated in 5 ml of ethyl acetate, gives 0.4 g of (R,S)-6-dimethylamino-2-imino-8-trifluoromethyl-5,6-dihydro-2H,4H-thiazolo[5,4,3-ij]quinoline dimethanesulphonate in the form of a white powder melting at 176° C.

(R,S)-4-Dimethylamino-6-trifluoromethyl-1,2,3,4-tetrahydroquinoline may be prepared in the following manner: 5 ml of trifluoroacetic acid are added to a solution of 2.5 g of tert-butyl (R,S)-4-dimethylamino-6-trifluoromethyl-1,2,3,4-tetrahydroquinoline-1-carboxylate in 25 ml of dichloromethane. After 18 hours at a temperature close to 20° C., the yellow solution obtained is concentrated to dryness under reduced pressure. The residue is treated with a dilute sodium hydrogen carbonate solution and extracted with ethyl ether. The organic phase is washed with distilled water and then with a saturated sodium chloride solution, dried over magnesium sulphate and concentrated to dryness under reduced pressure (2 kPa) at 50° C. 1.6 g of (R,S)-4-dimethylamino-6-trifluoromethyl-1,2,3,4-tetrahydroquinoline are thus obtained in the form of an orange-coloured oil which is used as it is in the next step [$^1$H NMR spectrum in CDCl$_3$, T=300K, δ in ppm (400 MHz): 1.90 and 2.05 (1H each, m, CH$_2$), 2.32 (6H, s, N(CHI)$_2$), 3.35 and 3.50 (1H each, m, NCH$_2$), 3.55 (1H, m, NCH), 6.48 (1H, d, J=8 Hz, arom. CH), 7.23 (1H, d, J=8 Hz, arom. CH), 7.50 (1H, s, arom. CH)].

tert-Butyl (R,S)-4-dimethylamino-6-trifluoromethyl-1,2,3,4-tetrahydroquinoline-1--carboxylate may be prepared in the following manner: 3.5 ml of a 5.6 N solution of dimethylamine in ethanol are added to a solution of 2.5 g of tert-butyl (R,S)-4-bromo-6-trifluoromethyl-1,2,3,4-tetrahydroquinoline-1-carboxylate in 25 ml of ethanol. After 18 hours at a temperature close to 20° C., the reaction mixture is concentrated to dryness under reduced pressure. The beige solid obtained is taken up in ethyl acetate and the organic phase is washed with distilled water and then with a saturated sodium chloride solution, dried over magnesium sulphate and concentrated to dryness under reduced pressure (2 kPa) at 50° C. 1.5 g of a fluid yellow oil are thus obtained, which oil is chromatographed on a silica gel column, eluting with a mixture of petroleum ether and ethyl acetate (95-5 by volume). 1 g of tert-butyl (R,S)-4-dimethylamino-6-trifluoromethyl-1,2,3,4-tetrahydroquinoline-1-carboxylate is thus obtained in the form of a white solid melting at 62° C.

tert-Butyl (R,S)-4-bromo-6-trifluoromethyl-1,2,3,4-tetrahydroquinoline-1-carboxylate may be prepared in the following manner: a solution of 24.7 g of tert-butyl 6-trifluoromethyl-1,2,3,4-tetrahydroquinoline-1-carboxylate in 250 ml of carbon tetrachloride is irradiated with a 100 W lamp for 5 hours, under reflux, in the presence of 14.5 g of N-bromosuccinimide and 1 g of benzoyl peroxide. The reaction mixture is filtered and then concentrated to dryness under reduced pressure, the orange-coloured oil obtained is concreted in 30 ml of pentane by trituration at a temperature of −15° C. 16.5 g of tert-butyl (R,S)-4-bromo-6-trifluoromethyl-1,2,3,4-tetrahydroquinoline-1-carboxylate are thus obtained in the form of a white solid melting at 72° C.

EXAMPLE 41

The procedure is carried out as in Example 1, but starting with 0.976 g of bromine diluted in 2 ml of acetic acid, 1.81 g of potassium thiocyanate and 1.7 g of (R,S)-4-diethylamino-6-trifluoromethyl-1,2,3,4-tetrahydroquinoline in 20 ml of acetic acid. 1.7 g of an orange-coloured oil are thus obtained, which oil is chromatographed on a silica gel column, eluting with a mixture of ethyl acetate and petroleum ether (80-20 by volume). The orange-coloured oil obtained (0.74 g) is taken up in 15 ml of ethyl ether, to which 1.1 ml of a 4 N solution of hydrochloric acid in isopropanol are added. 0.8 g of (R,S)-6-diethylamino-2-imino-8-trifluoromethyl-5,6-dihydro-2H,4H-thiazolo[5,4,3-ij]quinoline hydrochloride is thus obtained in the form of a cream-coloured powder melting at 225° C. (with decomposition).

(R,S)-4-Diethylamino-6-trifluoromethyl-1,2,3,4-tetrahydroquinoline may be prepared as in Example 40, but starting with 2.2 g of tert-butyl (R,S)-4-diethylamino-6-trifluoromethyl-1,2,3,4-tetrahydroquinoline-1-carboxylate in 20 ml of dichloromethane and 10 ml of trifluoroacetic acid. 1.53 g of (R,S)-4-diethylamino-6-trifluoromethyl-1,2,3,4-tetrahydroquinoline are thus obtained in the form of a brown oil which is used as it is in the next step.

tert-Butyl (R,S)-4-diethylamino-6-trifluoromethyl-1,2,3,4-tetrahydroquinoline-1-carboxylate may be prepared as in Example 40 but starting with 6 g of tert-butyl (R,S)-4-bromo-6-trifluoromethyl-1,2,3,4-tetrahydroquinoline-1-carboxylate in 60 ml of ethanol and 5.76 g of diethylamine. 2.3 g of a brown oil are thus obtained, which oil is used as it is in the next step [$^1$H NMR spectrum in DMSO-$d_6$, T=300K, δ in ppm (300 MHz): 1.03 (6H, t, J=6 Hz, 2 CH$_3$), 1.65 and 1.95 (1H each, m, CH$_2$) 2.45 (4H, m, 2 NCH$_2$), 3.30 (2H, m, NCH$_2$), 3.95 (1H, m, NCH), 6.45 (1H, s, NH), 6.55 (1H, d, J=8 Hz, arom. CH), 7.20 (1H, d, J=8 Hz, arom. CH), 7.65 (1H, s, arom. CH)].

EXAMPLE 42

1.52 g of bromine diluted in 5 ml of acetic acid are added dropwise over 10 minutes, at a temperature close to 20° C., to a solution of 2.8 g of potassium thiocyanate in 25 ml of acetic acid and the mixture is kept stirred for 1 hour, then a solution of 2.5 g of (R,S)-4-ethylmethylamino-6-trifluoromethyl-1,2,3,4-tetrahydroquinoline in 5 ml of acetic acid is poured in. The reaction mixture is stirred for 20 hours at the same temperature, poured over ice, alkalinized with a solution of aqueous ammonia at 20% and extracted with three times 100 ml of ethyl acetate. The organic phases are combined, washed with 100 ml of distilled water, dried over magnesium sulphate and concentrated to dryness under reduced pressure (2 kPa) at 40° C. The crude product is chromatographed on a silica gel column, eluting with a mixture of petroleum ether and tetrahydrofuran (70-30 by volume) and gives 1.2 g of a yellow oil. The latter is redissolved in 25 ml of ethyl ether, and then supplemented with 1.6 ml of hydrochloric isopropanol (about 4 N). 1 g of (R,S)-2-imino-6-ethylmethylamino-8-trifluoromethyl-5,6-dihydro-2H,4H-thiazolo[5,4,3-ij]quinoline dihydrochloride is thus obtained in the form of a white solid melting at 230° C. with decomposition.

(R,S)-4-Ethylmethylamino-6-trifluoromethyl-1,2,3,4-tetrahydroquinoline may be prepared as in Example 40 but starting with 3.5 g of tert-butyl (R,S)- 4-ethylmethylamino-6-trifluoromethyl-1,2,3,4-tetrahydroquinoline-1-carboxylate, 10 ml of dichloromethane and 10 ml of trifluoroacetic acid. 2.5 g of (R,S)-4-ethylmethylamino-6-trifluoromethyl-1,2,3,4-tetrahydroquinoline are thus obtained in the form of a brown oil which is used as it is in the next step [$^1$H NMR spectrum in DMSO-$d_6$, T=300K, δ in ppm (300 MHz): 1.05 (3H, t, J=6 Hz, CH$_3$), 1.70 and 1.90 (1H each, m, CH$_2$), 2.22 (3H, s, NCH$_3$), 2.45 (2H, m, NCH$_2$)I 3.30 (2H, m, NCH$_2$), 3.80 (1H, m, NCH), 6.45 (1H, s, NH), 6.55 (1H, d, J=8 Hz, arom. CH), 7.20 (1H, d, arom. CH), 7.55 (1H, s, arom. CH)].

tert-Butyl (R,S)-4-ethylmethylamino-6-trifluoromethyl-1,2,3,4-tetrahydroquinoline-1-carboxylate may be prepared as in Example 40, but starting with 7.5 g of tert-butyl (R,S)-4-bromo-6-trifluoromethyl-1,2,3,4-tetrahydroquinoline-1-carboxylate, 80 ml of ethanol and 5.8 g of ethylmethylamine. 3.2 g of a viscous orange-coloured oil are thus obtained, which oil is used as it is in the next step [$^1$H NMR spectrum in DMSO-$d_6$, T=300K, δ in ppm (400 MHz): 1.01 (3H, t, J=6 Hz, CH$_3$), 1.51 (9H, s, (CH$_3$)$_3$), 1.80 and 1.95 (1H each, m, CH$_2$), 2.16 (3H, s, NCH$_3$), 2.42 (2H, q, J=6 Hz, NCH$_2$), 3.55 and 3.88 (1H each, m, NCH$_2$), 3.91 (1H, m, NCH), 7.50 (1H, d, J=8 Hz, arom. CH), 7.78 (1H, s, arom. CH), 7.86 (1H, d, J=8 Hz, arom. CH)].

EXAMPLE 43

The procedure is carried out as in Example 42, but starting with 0.83 g of bromine diluted in 20 ml of acetic acid, 1.52 g of potassium thiocyanate and 1.6 g of (R,S)-4-thiomorpholino-6-trifluoromethyl-1,2,3,4-tetrahydroquinoline in 15 ml of acetic acid. 1.6 g of an orange-coloured foam are thus obtained, which foam is chromatographed on a silica gel column, eluting with a mixture of ethyl acetate and petroleum ether (55-45 by volume). The yellow oil obtained (0.7 g) is taken up in 10 ml of ethyl acetate and 2 ml of a 1.94 N solution of methanesulphonic acid in isopropanol are added. 0.76 g of (R,S)-2-imino-6-thiomorpholino-8-trifluoromethyl-5,6-dihydro-2H,4H-thiazolo[5,4,3-ij]quinoline dimethanesulphonate is thus obtained in the form of a pink solid melting at about 180° C. (with decomposition).

(R,S)-4-Thiomorpholino-6-trifluoromethyl-1,2,3,4-tetrahydroquinoline may be prepared as in Example 40, but starting with 2.3 g of tert-butyl (R,S)-4-thiomorpholino-6-trifluoromethyl-1,2,3,4-tetrahydroquinoline-1-carboxylate in 25 ml of dichloromethane and 5 ml of trifluoroacetic acid. 1.6 g of (R,S)-4-thiomorpholino-6-trifluoromethyl-1,2,3,4- tetrahydroquinoline are thus obtained in the form of crystals melting at 90° C.

tert-Butyl (R,S)-4-thiomorpholino-6-trifluoromethyl-1,2,3,4-tetrahydroquinoline-1-carboxylate may be prepared as in Example 40, but starting with 6 g of tert-butyl (R,S)-4-bromo-6-trifluoromethyl-1,2,3,4-tetrahydroquinoline-1-carboxylate, 60 ml of ethanol and 3.3 g of thiomorpholine. 5.5 g of a viscous brown oil are thus obtained, which oil partially crystallizes. After trituration in 120 ml of boiling pentane, the insoluble matter is filtered off and the mother liquors cooled to −15° C. allow white crystals to be deposited. 1.5 g of tert-butyl (R,S)-4-thiomorpholino-6-trifluoromethyl-1,2,3,4-tetrahydroquinoline-1-carboxylate are thus obtained in the form of white crystals melting at 116° C.

EXAMPLE 44

The procedure is carried out as in Example 42, but starting with a solution of 0.512 g of potassium thiocyanate in 5 ml of acetic acid, 1 ml of a solution of 0.55 g of bromine in 2 ml of acetic acid and a solution of 0.55 g of (R,S)-4-trifluoroacetamido-6-trifluoromethyl-1,2,3,4-tetrahydroquinoline in 6 ml of acetic acid. 0.48 g of (R,S)-2-imino-6-trifluoroacetamido-8-trifluoromethyl-5,6-dihydro-2H,4H-thiazolo[5,4,3-ij]quinoline is thus obtained in the form of a beige solid melting at 236° C.

(R,S)-4-Trifluoroacetamido-6-trifluoromethyl-1,2,3,4-tetrahydroquinoline may be prepared in the following manner: 1.28 ml of trifluoroacetic anhydride are added dropwise to a solution of 2 g of (R,S)-4-amino-6-trifluoromethyl-1,2,3,4-tetrahydroquinoline in 20 ml in pyridine cooled to about −30° C. After 30 minutes, the reaction mixture is taken up in 150 ml of distilled water and extracted with 30 ml of dichloromethane. The organic phase is washed 3 times with 50 ml of distilled water and then with 20 ml of a solution of hydrochloric acid (1 N), and then again twice with 50 ml of distilled water and finally with 20 ml of a saturated sodium chloride solution. The organic phase, dried over magnesium sulphate and concentrated to dryness under reduced pressure (2 kPa) at 50° C., gives 1.2 g of a beige solid which is chromatographed on a silica gel, eluting with a mixture of petroleum ether and ethyl acetate (80-20 by volume). 0.4 g of (R,S)-4-trifluoroacetamido-6-trifluoromethyl-1,2,3,4-tetrahydroquinoline is thus obtained in the form of a white solid melting at 150° C.

(R,S)-4-Amino-6-trifluoromethyl-1,2,3,4-tetrahydroquinoline may be prepared in the following manner: 5 g of (R,S)-4-phthalimido-6-trifluoromethyl-1,2,3,4-tetrahydroquinoline in solution in 50 ml of methanol are heated under reflux for 5 hours in the presence of 1.4 ml of hydrazine hydrate. The reaction mixture is then taken up in water and the methanol is evaporated under reduced pressure. The solution is extracted with ethyl acetate, washed with sodium hydroxide, then with a saturated sodium chloride solution and then extracted 3 times with a total of 35 ml of hydrochloric acid (1 N). The aqueous phase is then alkalinized with 20 ml of sodium hydroxide (10 N), then extracted with ethyl acetate, washed with distilled water, dried over magnesium sulphate and concentrated to dryness under reduced pressure (2 kPa) at 60° C. 2.4 g of (R,S)-4-amino-6-trifluoromethyl-1,2,3,4-tetrahydroquinoline are thus obtained in the form of an orange-coloured oil which is used as it is in the next step [$^1$H NMR spectrum in DMSO-$d_6$, T=300K, δ in ppm (300 MHz): 1.65 and 1.80 (1H each, m, $CH_2$), 3.25 (2H, m, $NCH_2$), 3.80 (1H, m, NCH), 6.50 (1H, s, NH), 6.55 (1H, d, J=8 Hz, arom. CH), 7.15 (1H, d, J=8 Hz, arom. CH), 7.50 (1H, s, arom. CH)].

(R,S)-4-Phthalimido-6-trifluoromethyl-1,2,3,4-tetrahydroquinoline may be prepared as in Example 15, but starting with 16.25 g of tin tetrachloride, 8.25 g of N-para-toluenesulphonylmethyl-4-trifluoromethylaniline in 125 ml of dichloromethane, 4.35 g of N-vinylphthalimide in 60 ml of dichloromethane. 8.1 g of (R,S)-4-phthalimido-6-trifluoromethyl-1,2,3,4-tetrahydroquinoline are thus obtained in the form of a cream-coloured solid melting at 177° C.

The medicaments according to the invention consist of a compound of formula (I) or a salt of such a compound, in the pure state or in the form of a composition in which it is combined with any other pharmaceutically compatible product which may be inert or physiologically active. The medicaments according to the invention may be used by the oral, parenteral, rectal or topical route.

Tablets, pills, powders (gelatin capsules, cachets) or granules may be used as solid compositions for oral administration. In these compositions, the active ingredient according to the invention is mixed with one or more inert diluents such as starch, cellulose, sucrose, lactose or silica under an argon stream. These compositions may also comprise substances other than diluents, for example one or more lubricants such as magnesium stearate or talc, a colourant, a coating (sugar-coated tablets) or a glaze.

Pharmaceutically acceptable solutions, suspensions, emulsions, syrups and elixirs containing inert diluents such as water, ethanol, glycerol, vegetable oils or paraffin oil may be used as liquid compositions for oral administration. These compositions may comprise substances other than diluents, for example wetting, sweetening, thickening, flavouring or stabilizing products.

Sterile compositions for parenteral administration may be preferably aqueous or nonaqueous solutions, suspensions or emulsions. Water, propylene glycol, polyethylene glycol, vegetable oils, in particular olive oil, organic esters for injection, for example ethyl oleate, or other suitable organic solvents may be used as solvent or vehicle. These compositions may also contain adjuvants, in particular wetting, isotonizing, emulsifying, dispersing and stabilizing agents. Sterilization may be performed in a number of ways, for example by aseptizing filtration, by incorporating sterilizing agents into the composition, by irradiation or by heating. They may also be prepared in the form of sterile solid compositions which may be dissolved at the time of use in sterile water or any other sterile medium for injection.

Compositions for rectal administration are suppositories or rectal capsules which contain, in addition to the active product, excipients such as cocoa butter, semisynthetic glycerides or polyethylene glycols.

Compositions for topical administration may be for example creams, lotions, collyria, collutoria, nasal drops or aerosols.

In human therapy, the compounds according to the invention are particularly useful for the treatment and/or prevention of conditions which require the administration of an antagonist of the AMPA receptor or of an antagonist of the NMDA receptor. These compounds are in particular useful for treating and/or preventing all ischaemias and in particular cerebral ischaemia, the effects caused by anoxia, the development of neurodegenerative diseases, of HUNTINGDON's chorea, of ALZHEIMER's disease and other dementias, of amyotrophic lateral sclerosis or of other motor neuron diseases, of olivopontocerebellar atrophy and of PARKINSON's disease, against epileptogenic and/or convulsive manifestations, cerebral or spinal traumas, of traumas linked to degeneration of the inner ear or of the retina, of tinnitus, of anxiety, of depression, of schizophrenia, of TOURETTE's syndrome, of hepatic encephalopathies, of sleep disorders, of attention deficit disorders, of disorders of hormonal conditions (excess secretion of GH or LH, secretion of corticosterone), as analgesics, anti-inflammatory agents, antianoretics, antimigraine drugs, antiemetics and to treat poisoning by neurotoxins or other substances which are NMDA or AMPA receptor agonists, as well as neurological disorders associated with viral diseases such as viral meningitis and encephalitis, AIDS, rabies, measles and tetanus, for the prevention of, tolerance to and dependency on the symptoms of withdrawal from drugs and alcohol, and of inhibition of addiction to and of dependency on opiates, barbiturates, amphetamine and benzodiazepines, in the treatment of deficiencies linked to mitochrondrial abnormalities such as mitochondrial myopathy, LEBER's syndrome, WERNICKE's encephalopathy, RETT's syndrome, homocysteinaemia, hyperprolinaemia, hydroxybutyric-aminoaciduria, saturnine encephalopathy (chronic lead poisoning) and sulphite oxidase deficiency.

The doses depend on the desired effect, on the duration of treatment and on the route of administration used; they are generally between 10 mg and 300 mg per day by the oral route for an adult with unit doses ranging from 5 mg to 50 mg of active substance.

In general, the doctor will determine the appropriate dosage according to the age, weight and all the other factors which are specific to the subject to be treated.

The following examples illustrate compositions according to the invention:

Example A

Gelatin capsules containing 50-mg doses of active product having the following composition are prepared according to the usual technique:

| | |
|---|---|
| Compound of formula (I) | 50 mg |
| Cellulose | 18 mg |
| Lactose | 55 mg |
| Colloidal silica | 1 mg |
| Sodium carboxymethylstarch | 10 mg |
| Talc | 10 mg |
| Magnesium stearate | 1 mg |

Example B

Tablets containing 50-mg doses of active product having the following composition are prepared according to the usual technique:

| | |
|---|---|
| Compound of formula (I) | 50 mg |
| Lactose | 104 mg |
| Cellulose | 40 mg |
| Polyvidone | 10 mg |
| Sodium carboxymethylstarch | 22 mg |
| Talc | 10 mg |
| Magnesium stearate | 2 mg |
| Colloidal silica | 2 mg |
| Mixture of hydroxymethylcellulose, glycerin, titanium oxide (72–3.5–24.5) qs 1 finished film coated tablet of 245 mg | |

Example C

An injectable solution containing 10 mg of active product having the following composition is prepared:

| | |
|---|---|
| Compound of formula (I) | 10 mg |
| Benzoic acid | 80 mg |
| Benzyl alcohol | 0.06 ml |
| Sodium benzoate | 80 mg |
| Ethanol, 95% | 0.4 ml |
| Sodium hydroxide | 24 mg |
| Propylene glycol | 16 ml |
| Water qs | 4 ml |

What is claimed is:

1. A compound of formula (I):

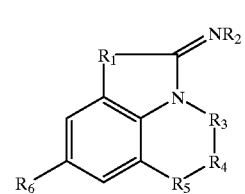

(I)

or a racemate, an enantiomer, a diastereoisomer or an inorganic or organic acid salt thereof,
in which:

$R_1$ is a sulphur atom;

$R_2$ is a hydrogen atom or an alkyl radical;

—$R_3$—$R_4$—$R_5$— is a chain having formula —$CH_2$—$CH_2$—$CH_2$—, —$CH(R_7)$—$CH_2$—$CH_2$—, —$CH_2$—$CH_2$—$CH(R_8)$—, —$CH_2$—$CH(R_9)$—$CH_2$—, —$CH_2$—$CH_2$—$CO$—, —$CH_2$—$CF_2$—$CH_2$—, or —$CH_2$—$CF_2$—$CH(OH)$—;

$R_6$ is a polyfluoroalkyl, polyfluoroalkoxy or polyfluoroalkylthio radical;

$R_7$ is an alkyl, —$CH_2OH$, —$CH_2$—$SO_2$-alk or —$CH_2$—$NR_{11}R_{12}$ radical;

$R_8$ is an alkyl radical, a hydroxyl, an —$CH_2OH$, —$NR_{11}R_{12}$, —$CH_2$—$NR_{11}R_{12}$, —S-alk, —SO-alk, —$SO_2$-alk, thienyl, furyl, or phenyl radical or a phenyl radical substituted with a substituent chosen from: halogen atoms, alkyl radicals and alkoxy radicals;

$R_9$ is an alkyl or —$CH_2OH$ radical;

$R_{11}$ is a hydrogen atom, an alkyl, a —CO-alk or —CO—$CF_3$ radical;

$R_{12}$ is a hydrogen atom or an alkyl radical;

or $R_{11}$ and $R_{12}$ form, with the nitrogen atom to which they are attached, a saturated or unsaturated 5- or 6-membered heterocycle which may or may not contain another heteroatom chosen from: nitrogen, oxygen and sulphur; wherein said heterocycle is unsubstituted or substituted with at least one substituent chosen from: alkyl radicals, phenyl radicals, halophenyl radicals and phenylalkyl radicals;

alk is an alkyl radical;

wherein, unless otherwise indicated, said alkyl and alkoxy radicals and portions thereof have from 1 to 6 straight- or branched-chain carbon atoms.

2. The compound according to claim 1, wherein $R_6$ is a polyfluoroalkyl radical chosen from: trifluoromethyl, 2,2,2-trifluoroethyl, 1,1,2,2-tetrafluoroethyl, perfluoroethyl, perfluoropropyl and perfluorobutyl radicals.

3. The compound according to claim 1, wherein $R_6$ is a polyfluoroalkoxy radical chosen from: trifluoromethoxy, perfluoroethoxy, 2,2,2-trifluoroethoxy, 1,1,2,2- tetrafluoroethoxy, 2,2,3,3,3-pentafluoropropoxy, perfluoropropoxy and perfluorobutoxy radicals.

4. The compound according to claim 1, wherein $R_6$ is a polyfluoroalkylthio radical chosen from: trifluoromethylthio, perfluoroethylthio and perfluoropropylthio radicals.

5. The compound according to claim 1, wherein $R_{11}$ and $R_{12}$ form, with the nitrogen atom to which they are attached, a saturated or unsaturated 5- or 6-membered heterocycle which may or may not contain another heteroatom chosen from: nitrogen, oxygen and sulphur; and further wherein said heterocycle is unsubstituted or substituted with an alkyl, a phenyl, a halophenyl or a phenylalkyl radical.

6. The compound according to claim 5, wherein said heterocycle is chosen from: pyrrolidine, piperidine, piperazine, morpholine and thiomorpholine.

7. The compound according to claim 1, wherein
$R_1$ is a sulphur atom;
$R_2$ is a hydrogen atom or an alkyl radical;
—$R_3$—$R_4$—$R_5$— is a chain having formula —$CH_2$—$CH_2$—$CH_2$—, —$CH(R_7)$—$CH_2$—$CH_2$—, —$CH_2$—$CF_2$—$CH(OH)$—, —$CH_2$—$CH_2$—$CH(R_8)$—, or —$CH_2$—$CH_2$—CO;
$R_6$ is a polyfluoroalkyl, polyfluoroalkoxy or polyfluoroalkylthio radical;
$R_7$ is an alkyl radical, or a —$CH_2OH$ or —$CH_2NR_{11}R_{12}$ radical;
$R_8$ is an —$NR_{11}R_{12}$ radical, or a —$SO_2$-alk-, —SO-alk- or phenyl radical;
$R_{11}$ is a hydrogen atom or an alkyl or —CO-alk radical;
$R_{12}$ is a hydrogen atom or an alkyl radical,
or $R_{11}$ and $R_{12}$ form, with the nitrogen atom to which they are attached, a saturated or unsaturated 5- or 6-membered heterocycle which may or may not contain another heteroatom chosen from: nitrogen, oxygen or sulphur;
wherein, unless otherwise indicated, the alkyl and alkoxy radicals and portions thereof have from 1 to 6 straight- or branched-chain carbon atoms.

8. The compound according to claim 1, wherein said compound is chosen from:
2-imino-8-trifluoromethoxy-5,6-dihydro-2H,4H-thiazolo[5,4,3-ij]quinoline,
2-imino-8-trifluoromethyl-5,6-dihydro-2H,4H-thiazolo[5,4,3-ij]quinoline,
(R,S)-2-imino-4-methyl-8-trifluoromethyl-5,6-dihydro-2H,4H-thiazolo[5,4,3-ij]quinoline and enantiomers thereof,
2-imino-8-trifluoromethoxy-2H,4H-thiazolo[5,4,3-ij]-quinolin-6-one,
(R,S)-2-imino-6-phenyl-8-trifluoromethyl-5,6-dihydro-2H,4H-thiazolo[5,4,3-ij]quinoline and enantiomers thereof,
(R,S)-2-imino-8-trifluoromethyl-5,6-dihydro-2H,4H-thiazolo[5,4,3-ij]quinoline-4-methanol and enantiomers thereof,
(R,S)-5,5-Difluoro-6-hydroxy-2-imino-8-trifluoromethyl-5,6-dihydro-2H,4H-thiazolo[5,4,3-ij]quinoline and enantiomers thereof,
(R,S)-Ethylmethyl(2-imino-8-trifluoromethyl-5,6-dihydro-2H,4H-thiazolo[5,4,3-ij]quinol-4-ylmethyl)-amine and enantiomers thereof,
(R,S)-2-imino-6-ethylsulphinyl-8-trifluoromethyl-5,6-dihydro-2H,4H-thiazolo[5,4,3-ij]quinoline and enantiomers thereof,
(R,S)-2-imino-6-ethylsulphonyl-8-trifluoromethyl-5,6-dihydro-2H,4H-thiazolo[5,4,3-ij]quinoline and enantiomers thereof, and inorganic or organic acid salts thereof.

9. A process for the preparation of a compound of formula (I):

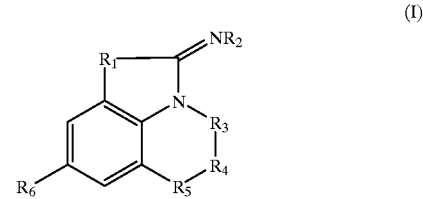

or a racemate, an enantiomer, a diastereoisomer or an inorganic or organic acid salt thereof,
wherein:
$R_1$ is a sulphur atom;
$R_2$ is a hydrogen atom;
—$R_3$—$R_4$—$R_5$— is a chain having formula —$CH_2$—$CH_2$—$CH_2$—, —$CH(R_7)$—$CH_2$—$CH_2$—, —$CH_2$—$CH_2$—$CH(R_8)$—, —$CH_2$—$CH(R_9)$—$CH_2$—, —$CH_2$—$CH_2$—CO—, —$CH_2$—$CF_2$—$CH_2$—, or —$CH_2$—$CF_2$—$CH(OH)$—;
$R_6$ is a polyfluoroalkyl, polyfluoroalkoxy or polyfluoroalkylthio radical;
$R_7$ is an alkyl, —$CH_2OH$, —$CH_2$—$SO_2$-alk or —$CH_2$—$NR_{11}R_{12}$ radical;
$R_8$ is an alkyl radical, —$CH_2OH$, —$NR_{11}R_{12}$, —$CH_2$—$NR_{11}R_{12}$, —S-alk, —SO-alk, —$SO_2$-alk, thienyl, furyl, or phenyl radical or a phenyl radical substituted with a substituent chosen from: halogen atoms, alkyl radicals and alkoxy radicals;
$R_9$ is an alkyl or —$CH_2OH$ radical;
$R_{11}$ is a hydrogen atom, an alkyl, a —CO-alk or —CO—$CF_3$ radical;
$R_{12}$ is a hydrogen atom or an alkyl radical;
or $R_{11}$ and $R_{12}$ form, with the nitrogen atom to which they are attached, a saturated or unsaturated 5- or 6-membered heterocycle which may or may not contain another heteroatom chosen from: nitrogen, oxygen and sulphur; wherein said heterocycle is unsubstituted or substituted with at least one substituent chosen from: alkyl radicals, phenyl radicals, halophenyl radicals and phenylalkyl radicals;
alk is an alkyl radical;
wherein, unless otherwise indicated, said alkyl and alkoxy radicals and portions thereof have from 1 to 6 straight- or branched-chain carbon atoms;
said process comprising:
reacting an alkali metal thiocyanate with a compound of formula (II):

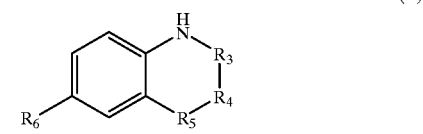

wherein:
—$R_3$—$R_4$—$R_5$— is a chain having formula —$CH_2$—$CH_2$—$CH_2$—, —$CH(R_7)$—$CH_2$—$CH_2$—, —$CH_2$—

$CH_2-CH(R_8)-$, $-CH_2-CH(R_9)-CH_2-$, $-CH_2-CH_2-CO-$, $-CH_2-CF_2-CH_2-$, or $-CH_2-CF_2-CH(OH)-$;

$R_6$ is a polyfluoroalkyl, polyfluoroalkoxy or polyfluoroalkylthio radical;

$R_7$ is an alkyl, $-CH_2OH$, $-CH_2-SO_2$-alk or $-CH_2-NR_{11}R_{12}$ radical;

$R_8$ is a $-CH_2-OH$, $-NR_{11}R_{12}$, $-CH_2-NR_{11}R_{12}$, $-S$-alk, $SO$-alk, $SO_2$-alk, thienyl, or furyl, or phenyl radical or a phenyl substituted with a substituent chosen from: halogen atoms, and alkyl and alkoxy radicals;

$R_9$ is an alkyl or $-CH_2OH$ radical;

$R_{11}$ is a hydrogen atom, an alkyl, a $-CO$-alk or $-CO-CF_3$ radical;

$R_{12}$ is a hydrogen atom or an alkyl radical;

or $R_{11}$ and $R_{12}$ form, with the nitrogen atom to which they are attached, a saturated or unsaturated 5- or 6-membered heterocycle which may or may not contain another heteroatom chosen from: nitrogen, oxygen and sulphur; wherein said heterocycle is unsubstituted or substituted with at least one substituent chosen from: alkyl radicals, phenyl radicals, halophenyl radicals and phenylalkyl radicals;

alk is an alkyl radical;

wherein, unless otherwise indicated, said alkyl and alkoxy radicals and portions thereof have from 1 to 6 straight- or branched-cha carbon atoms.

10. The process of claim 9, further comprising isolating said compound of formula (I), or a diastereoisomer, racemate or enantiomer thereof.

11. The process of claim 10, further comprising converting said compound of formula (I), or a diastereoisomer, racemate or enantiomer thereof to an inorganic or organic acid salt.

12. A process for the preparation of a compound of formula (I):

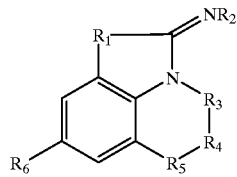

(I)

or a racemate, an enantiomer, a diastereoisomer or an inorganic or organic acid salt thereof, wherein:

$R_1$ is a sulphur atom;

$R_2$ is an alkyl radical;

$-R_3-R_4-R_5-$ is a chain having formula $-CH_2-CH_2-CH_2-$, $-CH(R_7)-CH_2-CH_2-$, $-CH_2-CH_2-CH(R_8)-$, $-CH_2-CH(R_9)-CH_2-$, $-CH_2-CH_2-CO-$, $-CH_2-CF_2-CH_2-$, or $-CH_2-CF_2-CH(OH)-$;

$R_6$ is a polyfluoroalkyl, polyfluoroalkoxy or polyfluoroalkylthio radical;

$R_7$ is an alkyl, $-CH_2OH$, $-CH_2-SO_2$-alk or $-CH_2-NR_{11}R_{12}$ radical;

$R_8$ is an alkyl radical, a hydroxyl, or a $-CH_2OH$, $-NR_{11}R_{12}$, $-CH_2-NR_{11}R_{12}$, $-S$-alk, $-SO$-alk, $-SO_2$-alk, thienyl, furyl, or phenyl radical or a phenyl radical substituted with a substituent chosen from: halogen atoms, alkyl radicals and alkoxy radicals;

$R_9$ is an alkyl or $-CH_2OH$ radical;

$R_{11}$ is a hydrogen atom, an alkyl, a $-CO$-alk or $-CO-CF_3$ radical;

$R_{12}$ is a hydrogen atom or an alkyl radical;

or $R_1$, and $R_{12}$ form, with the nitrogen atom to which they are attached, a saturated or unsaturated 5- or 6-membered heterocycle which may or may not contain another heteroatom chosen from: nitrogen, oxygen and sulphur; wherein said heterocycle is unsubstituted or substituted with at least one substituent chosen from: alkyl radicals, phenyl radicals, halophenyl radicals and phenylalkyl radicals;

alk is an alkyl radical;

wherein, unless otherwise indicated, said alkyl and alkoxy radicals and portions thereof have from 1 to 6 straight- or branched-chain carbon atoms;

said process comprising:

alkylating a compound of formula (I)

wherein:

$R_1$ is a sulphur atom;

$R_2$ is a hydrogen atom;

$-R_3-R_4-R_5-$ is a chain having formula $-CH_2-CH_2-CH_2-$, $-CH(R_7)-CH_2-CH_2-$, $-CH_2-CH_2-CH(R_8)-$, $-CH_2-CH(R_1)-CH_2-$, $-CH_2-CH_2-CO-$, $-CH_2-CF_2-CH_2-$, or $-CH_2-CF_2-CH(OH)-$;

$R_6$ is a polyfluoroalkyl, polyfluoroalkoxy or polyfluoroalkylthio radical;

$R_7$ is an alkyl, $-CH_2OH$, $-CH_2-SO_2$-alk or $-CH_2-NR_{11}R_{12}$ radical;

$R_8$ is an alkyl radical, a hydroxyl, or a $-CH_2OH$, $-NR_{11}R_{12}$, $-CH_2-NR_1,R_{12}$, $-S$-alk, $-SO$-alk, $-SO_2$-alk, thienyl, furyl, or phenyl radical or a phenyl radical substituted with a substituent chosen from: halogen atoms, alkyl radicals and alkoxy radicals;

$R_9$ is an alkyl or $-CH_2OH$ radical;

$R_{11}$ is a hydrogen atom, an alkyl, a $-CO$-alk or $-CO-CF_3$ radical;

$R_{12}$ is a hydrogen atom or an alkyl radical;

or $R_{11}$ and $R_{12}$ form, with the nitrogen atom to which they are attached, a saturated or unsaturated 5- or 6-membered heterocycle which may or may not contain another heteroatom chosen from: nitrogen, oxygen and sulphur; wherein said heterocycle is unsubstituted or substituted with at least one substituent chosen from: alkyl radicals, phenyl radicals, halophenyl radicals and phenylalkyl radicals;

alk is an alkyl radical;

wherein, unless otherwise indicated, said alkyl and alkoxy radicals and portions thereof have from 1 to 6 straight- or branched-chain carbon atoms.

13. The process of claim 12, further comprising isolating said compound of formula (I), or a diastereoisomer, racemate, or enantiomer thereof.

14. The process of claim 13, further comprising converting said compound of formula (I), or a diastereoisomer, racemate or enantiomer thereof to an inorganic or organic acid salt.

15. A process for the preparation of a compound of formula (I):

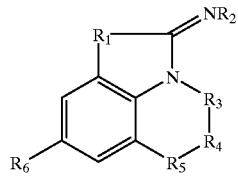
(I)

or a racemate, an enantiomer, a diastereoisomer or an inorganic or organic acid salt thereof,
wherein:
$R_1$ is a sulphur atom;
$R_2$ is a hydrogen atom or an alkyl radical;
—$R_3$—$R_4$—$R_5$— below is a chain having formula —$CH_2$—$CH_2$—$CH(R_8)$—;
$R_6$ is a polyfluoroalkyl, polyfluoroalkoxy or polyfluoroalkylthio radical; and
$R_8$ is a hydroxyl radical;
wherein, unless otherwise indicated, said alkyl and alkoxy radicals and portions thereof have from 1 to 6 straight- or branched-chain carbon atoms;
said process comprising:
reducing a compound of formula (I) in which:
$R_1$ is a sulphur atom;
$R_2$ is a hydrogen atom or an alkyl radical;
—$R_3$—$R_4$—$R_5$— is a chain having formula —$CH_2$—$CH_2$—CO—;
$R_6$ is a polyfluoroalkyl, polyfluoroalkoxy or polyfluoroalkylthio radical; and
wherein, unless otherwise indicated, said alkyl and alkoxy radicals and portions thereof have from 1 to 6 straight- or branched-chain carbon atoms.

16. The process of claim 15, further comprising isolating said compound of formula (I), or a diastereoisomer, racemate, or enantiomer thereof.

17. The process of claim 16, further comprising converting said compound of formula (I), or a diastereoisomer, racemate or enantiomer thereof to an inorganic or organic acid salt.

18. A process for the preparation of a compound of formula (I):

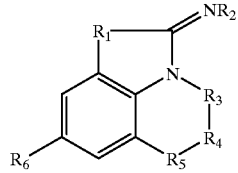
(I)

or an isomer, a racemate, an enantiomer or an inorganic or organic acid salt thereof, wherein:
$R_1$ is a sulphur or selenium atom;
$R_2$ is a hydrogen atom or an alkyl radical;
—$R_3$—$R_4$—$R_5$— is a chain having formula —$CH_2$—$CH_2$—SO—, —$CH_2$—$CH_2$—$SO_2$—, —$CH_2$—$CH(R_{13})$—SO— or —$CH_2$—$CH(R_{13})$—$SO_2$—;
$R_6$ is a polyfluoroalkyl, polyfluoroalkoxy or polyfluoroalkylthio radical;
$R_{13}$ is an alkyl or —$CH_2OH$ radical; and wherein, unless otherwise indicated, said alkyl and alkoxy radicals and portions thereof have from 1 to 6 straight- or branched-chain carbon atoms;
said process comprising:
oxidizing a compound of general formula (I) in which
$R_1$ is a sulphur or selenium atom;
$R_2$ is a hydrogen atom or an alkyl radical;
—$R_3$—$R_4$—$R_5$— is a chain having formula —$CH_2$—$CH_2$—S—, or —$CH_2$—$CH(R_{13})$—S—;
$R_6$ is a polyfluoroalkyl, polyfluoroalkoxy or polyfluoroalkylthio radical;
$R_{13}$ is an alkyl or —$CH_2OH$ radical; and
wherein, unless otherwise indicated, said alkyl and alkoxy radicals and portions thereof have from 1 to 6 straight- or branched-chain carbon atoms.

19. The process of claim 18, further comprising isolating said compound of formula (I), or an isomer, racemate, or enantiomer thereof.

20. The process of claim 19, further comprising converting said compound of formula (I), or an isomer, racemate or enantiomer thereof to an inorganic or organic acid salt.

21. A process for the preparation of a compound of formula (I):

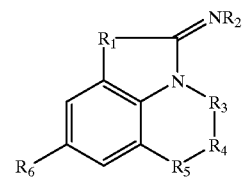
(I)

or a racemate, an enantiomer, a diastereoisomer or an inorganic or organic acid salt thereof,
wherein:
$R_1$ is a sulphur atom;
$R_2$ is a hydrogen atom;
—$R_3$—$R_4$—$R_5$— is a chain having formula —$CH(R_7)$—$CH_2$—$CH_2$—;
$R_6$ is a polyfluoroalkyl, polyfluoroalkoxy or polyfluoroalkylthio radical;
$R_7$ is a —$CH_2$—$NR_{11}R_{12}$ radical;
$R_{11}$ is a hydrogen atom, an alkyl, a —CO-alk or —CO—$CF_3$ radical;
$R_{12}$ is a hydrogen atom or an alkyl radical;
or $R_{11}$ and $R_{12}$ form, with the nitrogen atom to which they are attached, a saturated or unsaturated 5- or 6-membered heterocycle which may or may not contain another heteroatom chosen from: nitrogen, oxygen and sulphur; wherein said heterocycle is unsubstituted or substituted with at least one substituent chosen from: alkyl radicals, phenyl radicals, halophenyl radicals and phenylalkyl radicals;
alk is an alkyl radical;
wherein, unless otherwise indicated, said alkyl and alkoxy radicals and portions thereof have from 1 to 6 straight- or branched-chain carbon atoms; and
said process comprising:
reacting an amine $HNR_{11}R_{12}$ wherein:
$R_{11}$ is a hydrogen atom, an alkyl, a —CO-alk or —CO—$CF_3$ radical;
$R_{12}$ is a hydrogen atom or an alkyl radical;

or $R_{11}$ and $R_{12}$ form, with the nitrogen atom to which they are attached, a saturated or unsaturated 5- or 6-membered heterocycle which may or may not contain another heteroatom chosen from: nitrogen, oxygen and sulphur; wherein said heterocycle is unsubstituted or substituted with at least one substituent chosen from: alkyl radicals, phenyl radicals, halophenyl radicals and phenylalkyl radicals;

alk is an alkyl radical;

wherein, unless otherwise indicated, said alkyl and alkoxy radicals and portions thereof have from 1 to 6 straight- or branched-chain carbon atoms; with a compound of formula (Ill) to form an intermediate;

wherein said compound of formula (III) has the formula:

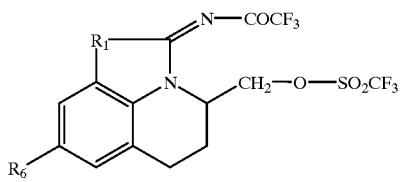

(III)

in which:

$R_1$ is a sulphur atom; and $R_6$ is a polyfluoroalkyl, polyfluoroalkoxy or polyfluoroalkylthio radical; and hydrolyzing said intermediate to release an imine.

22. The process of claim 21, further comprising isolating said compound of formula (I), or a diastereoisomer, racemate, or enantiomer thereof.

23. The process of claim 22, further comprising converting said compound of formula (I), or a diastereoisomer, racemate or enantiomer thereof to an inorganic or organic acid salt.

24. A pharmaceutical composition, said composition comprising a pharmaceutically effective amount of a compound of formula (I):

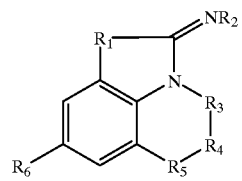

(I)

or a racemate, an enantiomer, a diastereoisomer or pharmaceutically acceptable inorganic or organic acid salt thereof, in which:

$R_1$ is a sulphur atom;

$R_2$ is a hydrogen atom or an alkyl radical;

—$R_3$—$R_4$—$R_5$— is a chain having formula —$CH_2$—$CH_2$—$CH_2$—, —$CH(R_7)$—$CH_2$—$CH_2$—, —$CH_2$—$CH_2$—$CH(R_8)$—, —$CH_2$—$CH(R_9)$—$CH_2$—, —$CH_2$—$CH_2$—$CO$—, —$CH_2$—$CF_2$—$CH_2$—, or —$CH_2$—$CF_2$—$CH(OH)$;

$R_6$ is a polyfluoroalkyl, polyfluoroalkoxy or polyfluoroalkylthio radical;

$R_7$ is an alkyl, —$CH_2OH$, —$CH_2$—$SO_2$-alk or —$CH_2$—$NR_{11}R_{12}$ radical;

$R_8$ is an alkyl radical, a hydroxyl atom, an —$CH_2OH$, —$NR_1,R_{12}$, —$CH_2$—$NR_{11}R_{12}$, —S-alk, —SO-alk, —$SO_2$-alk, thienyl, furyl, or phenyl radical or a phenyl radical substituted with a substituent chosen from: halogen atoms, alkyl radicals and alkoxy radicals;

$R_9$ is an alkyl or —$CH_2OH$ radical;

$R_{11}$ is a hydrogen atom, an alkyl, a —CO-alk or —CO—$CF_3$ radical;

$R_{12}$ is a hydrogen atom or an alkyl radical;

or $R_{11}$ and $R_{12}$ form, with the nitrogen atom to which they are attached, a saturated or unsaturated 5- or 6-membered heterocycle which may or may not contain another heteroatom chosen from: nitrogen, oxygen and sulphur; wherein said heterocycle is unsubstituted or substituted with at least one substituent chosen from: alkyl radicals, phenyl radicals, halophenyl radicals and phenylalkyl radicals;

alk is an alkyl radical;

wherein, unless otherwise indicated, said alkyl and alkoxy radicals and portions thereof have from 1 to 6 straight- or branched-chain carbon atoms; and a pharmaceutically compatible diluent.

* * * * *

UNITED STATES PATENT AND TRADEMARK OFFICE
CERTIFICATE OF CORRECTION

PATENT NO. : 6,288,075 B1  
DATED : September 11, 2001  
INVENTOR(S) : Jean-Claude Hardy et al.

Page 1 of 1

It is certified that error appears in the above-identified patent and that said Letters Patent is hereby corrected as shown below:

Column 60,  
Line 31, "—$CH_2$—$CH(R,)$—$CH_2$—" should read -- —$CH_2$—$CH(R_9)$—$CH_2$— --.  
Column 61,  
Line 60, after "2H" delete the space.

Column 62,  
Line 24, "—$CH_2$—$CH(R,)$—$CH_2$—" should read -- —$CH_2$—$CH(R_9)$—$CH_2$— --.

Column 63,  
Line 28, "branched-cha" should read -- branched-chain --.

Column 64,  
Line 5, "$R_1$," should read -- $R_{11}$ --.  
Line 28, "—$CH_2$—$CH(R,)$—$CH_2$—" should read -- —$CH_2$—$CH(R_9)$—$CH_2$— --.  
Line 37, "—$CH_2$—$NR_1,R_{12}$" should read -- —$CH_2$—$NR_{11}R_{12}$ --.

Column 67,  
Line 15, "formula (Ill)" should read -- formula (III) --.

Column 68,  
Line 25, "—$NR_1,R_{12}$" should read -- —$NR_{11}R_{12}$ --.

Signed and Sealed this

Tenth Day of December, 2002

JAMES E. ROGAN  
*Director of the United States Patent and Trademark Office*